United States Patent [19]
Webster et al.

[11] Patent Number: 5,834,306
[45] Date of Patent: Nov. 10, 1998

[54] TISSUE SPECIFIC HYPOXIA REGULATED THERAPEUTIC CONSTRUCTS

[75] Inventors: Keith A. Webster; Nanette H. Bishopric, both of Palo Alto, Calif.

[73] Assignee: SRI International, Menlo Park, Calif.

[21] Appl. No.: 365,486

[22] Filed: Dec. 23, 1994

[51] Int. Cl.$^6$ .......................... C12N 15/00; C07H 21/04
[52] U.S. Cl. .................................. 435/320.1; 435/172.3; 536/24.1; 935/22; 935/36
[58] Field of Search ......................... 514/44; 435/172.1, 435/172.2, 172.3, 172.4, 320.1, 240.1, 240.2, 91.1, 91.31; 424/93.1, 93.21; 536/22.1; 530/450, 350; 511/44; 935/22, 36

[56] References Cited

FOREIGN PATENT DOCUMENTS

PCT/US91/01228  2/1990  WIPO.

OTHER PUBLICATIONS

Berr, E., et al., "Stable Delivery of Physiologic Levels of Recombinant Erythropoietin to the Systemic Circulation by Intramuscular Injection of Replication–Defective Adenovirus," *Basic Science* 90(4):1–3 (1994).

Blanchard, K.L., et al., "Hypoxic Induction of the Human Erythropoietin Gene: Cooperation between the Promoter and Enhancer, Each of Which Contains Steroid Receptor Response Elements," *Molecular and Cellular Biology* 12(12):5373 (1992).

Bredt, D.S., et al., "Cloned and expressed nitric oxide synthase structurally resembles cytochrome P–450 reductase," *Nature 351*:714 (1991).

Doria–Medina, C.L., et al., "Immunolocalization of GLUT–1 glucose transporter in rat skeletal muscle and in normal and hypoxic cardiac tissue,"*American Journal of Physiology* 265:E454 (1993).

Franz, W.–M., et al., "Heat–Specific Targeting of Firefly Luciferase by the Myosin Light Chain–2 Promoter and Developmental Regulation in Transgenic Mice," *Circulation Research* 73:629 (1993).

Gordon, L., et al., "Expression of Neural Cell Adhesion Molecule Immunoreactivity in Hypertrophic Myocardium," *Life Sciences* 47:601 (1990).

Kourembanas, S., et al., "Nitric Oxide Regulates the Expression of Vasoconstrictors and Growth Factors by Vascular Endothelium under both Normoxia and Hypoxia," *J. Clin. Invest.* 92:99 (1993).

Ladoux, A., et al., "Hypoxia is a Strong Inducer of Vascular Endothelial Growth Factor mRNA expression in the Heart," *Acedemic Press* 195(2):1005 (1993).

Madan, A., et al., "A 24–base–pair sequence 3' t the human erythropoietin gene contains a hypoxia–responsive transcriptional enhancer," *Proc. Natl. Acad. Sci. USA* 90:3928 (1993).

Maxwell, P.H., et al., "Inducible operation of the erythropoietin 3' enhancer in multiple cell lines: Evidence for a widespread oxygen–sensing mechanism," *Proc. Natl. Acad. Sci. USA* 90:2423 (1993).

Metzger, J.M., et al., "Skeletal troponin C reduces contractile sensitivity to acidosis in cardiac myocytes from transgenic mice," *Proc. Natl. Acad. Sci. USA* 90:9036 (1993).

Milano, C.A., et al., "Enhanced Myocardial Function in Transgenic Mice Overexpressing the $\beta_2$–Adrenergic Receptor," *Science* 264:582 (1994).

Semenza, G.L., et al., "A Nuclear Factor Induced by Hypoxia via De Nova Protein Synthesis Binds to the Human Erythropoietin Gene Enhancer at a Site Required for Transcriptional Activation," *Molecular and Cellular Biology* 12(12):5447 (1992).

Semenza, G.L., et al., "Hypoxia–inducible nuclear factors bind to an enhancer element located 3' to the human erythropoietin gene," *Proc. Natl. Acad. Sci. USA* 88:5680 (1991).

Subramaniam, A., et al., "Transgenic Analysis of the Thyroid–responsive Elements in the $\alpha$–Cardiac Myosin Heavy Chain Gene Promoter," *The Journal of Biological Chemistry* 268(6):4331 (1993).

Tsuchiya, T., et al., "Erythropoietin 5'–Flanking Sequence— Binding Protein Induced during Hypoxia and Cobalt Exposure," *J. Biochem.* 113(3):395 (1993).

Webster, K.A., et al., "Induction and Nuclear Accumulation of Fos and Jun Proto–oncogenes in Hypoxic Cardiac Myocytes," *The Journal of Biologica Chemistry* 268(22):16852 (1993).

Beck, I., et al., "Characterization of Hypoxia–Responsive Enhancer in the Human Erythropoietin Gene Shows Presence of Hypoxia–Inducible 120–Kd Nuclear DNA–Binding Protein in Erythropoietin–Producing and Nonproducing Cells," *Blood 82(3)*: 704–711 (1993).

Firth, J.D., et al., "Oxygen–regulated control elements in the phosphoglycerate kinase 1 and lactate dehydronase A genes: Similarities with the erythropoietin 3' enhancer," *Proc. Natl. Acad. Sci. USA 91*: 6496–6500 (1994).

Minchenko, A., et al., "Hypoxia–Regulatory Elements of the Human Vascular Endothelial Growth Factor Gene," *Cellular and Molecular Biology Research 40(1)*: 35–39 (1994).

Murphy, B.J., et al., "Metallothionein IIA Is Up–Regulated by Hypoxia in Human A431 Squamous Carcinoma Cells," *Cancer Research 54*: 5808–5810 (1994).

Murphy, B.J., et al., "Metallothionein IIA Is Up–Regulated by Hypoxia in Human Squamous Carcinoma Cells," *FASEB Journal 8(4–5)*: A128 (1994).

Wang, G.L., and G.L. Semenza, "General involvement of hypoxia–inducible factor 1 in transcriptional response to hypoxia," *Proc. Natl. Acad. Sci. USA 90*: 4304–4308 (1993).

(List continued on next page.)

*Primary Examiner*—Bruce R. Campbell
*Attorney, Agent, or Firm*—Bozicevic & Reed LLP

[57] ABSTRACT

Methods and compositions relating to chimeric genes containing (i) a tissue-specific promoter and (ii) a hypoxia response enhancer element, both of which are operably linked to a selected gene, such as a reporter gene, therapeutic gene (e.g., bcl-2, NOS, catalase and SOD), or deleterious gene are disclosed. Expression of the selected gene is enhanced in the target tissue under hypoxic conditions, such as conditions encountered during episodes of ischemia and reperfusion. The methods and compositions may be used as therapeutics and/or diagnostics.

18 Claims, 9 Drawing Sheets

OTHER PUBLICATIONS

Marshall, Science 269:1050–1055, 1995.
Miller et al., FASEB J., 9:190–199, 1995.
Culver et al., TIG, 10(5):174–178, 1994.
Hodgson, Exp. Opin. Ther. Pat., 5(5):459–468, 1995.
Maden et al., Proc. Nat. Acad. Sci. 90:3928–3932, 1993.
Prentice et al., Circulation, 88:(4 part 2), I475, 1993.
Franz et al., Circ. Res, 73:629–638, 1993.
Maxwell et al., Proc. Nat. Acad. Sci., 90:2423–2427, 1993.
Lafant et al., Lancet, 346: 1442–1443, 1995.
NIH "Report and Recommendations . . . ", Dec. 7, 1995, 1–40.

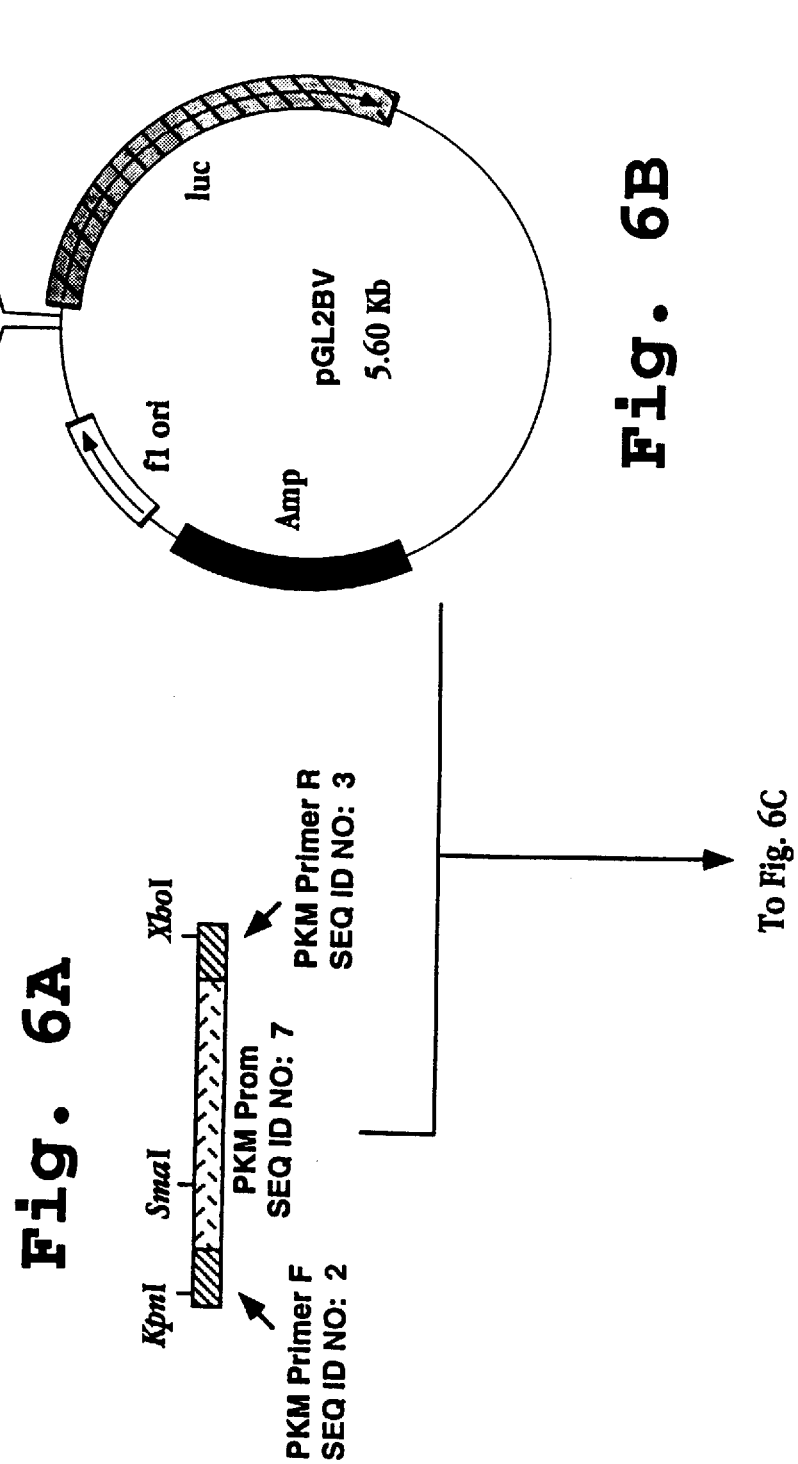

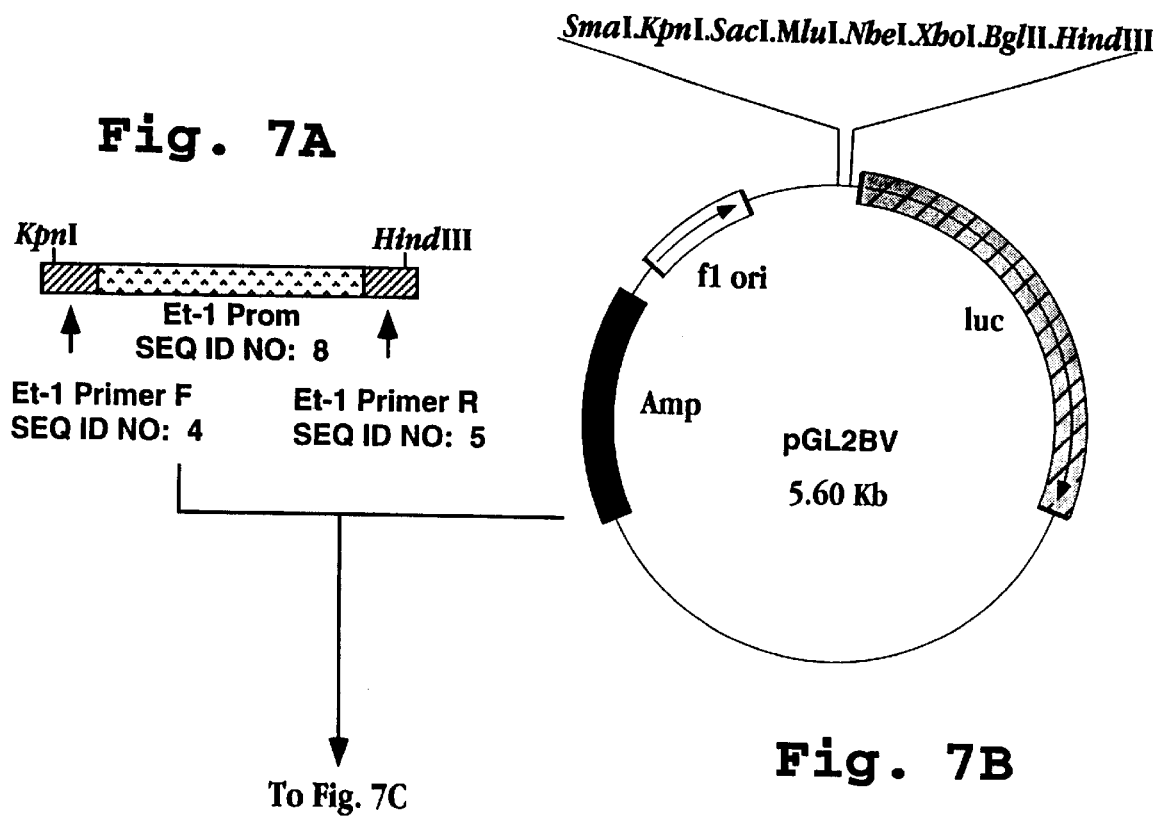
Fig. 7A
Fig. 7B
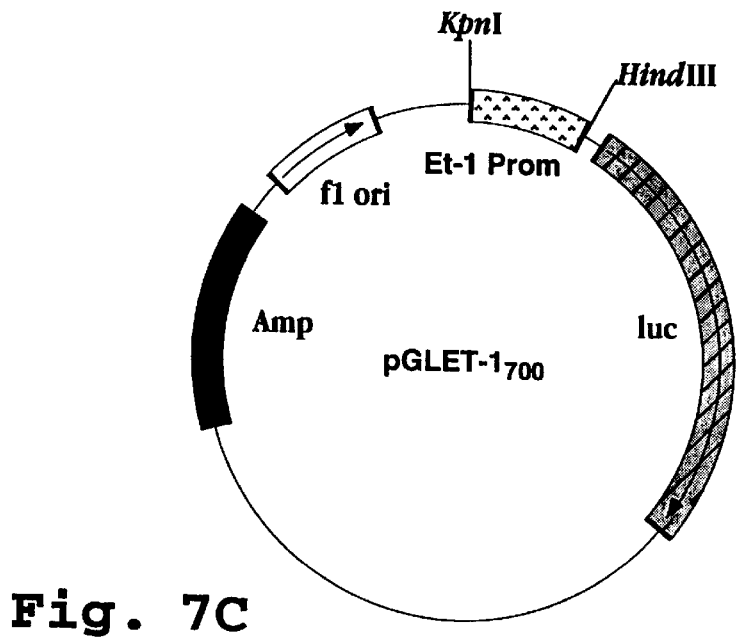
Fig. 7C

TISSUE SPECIFIC HYPOXIA REGULATED THERAPEUTIC CONSTRUCTS

This work was supported in part by NIH Grant # 5R29HL44578-04. Accordingly, the United States Government has certain rights in this invention.

FIELD OF THE INVENTION

This invention relates to chimeric genes (e.g., carried on expression vectors) containing therapeutic genes whose expression is under the control of tissue specific and hypoxia response enhancer elements.

REFERENCES

Ascadi, G., et al., *Nature* 352:815 (1991b).
Ascadi, G., et al., *New Biology* 3:71 (1991a).
Atkins, C. E., et al., *J. Am. Vet. Med. Assoc.* 201:613–618 (1992).
Ausubel, F. M., et al., *CURRENT PROTOCOLS IN MOLECULAR BIOLOGY*, John Wiley and Sons, Inc., Media Pa.
Berkner, K. L., *BioTechniques* 6:616 (1988).
Bisphopric, et al., *J. Clin. Invest.* 80:1194 (1987).
Breakefield, X. O., and DeLuca, N. A., *New Biol.* 3:230 (1992).
Bredt, D. S., et al., *Nature* 351:714–718 (1991).
Buttrick, P. M., et al., *Circ. Res.* 70:193–198 (1992).
Buttrick, P. M., et al., *Circ. Res.* 72:1211–1217 (1993).
Chatterjee, J., et al., *Science* 258:1485 (1992).
Chomczynski, P., and Sacchi, N., *Anal. Biochem.* 162:156–159 (1987).
Christiano, R. J., et al., *Proc. Natl. Acad. Sci. U.S.A.* 90:212 (1993).
Clair, D. K. S., et al., *Cancer Res.*, 51:939 (1991).
Dabareiner, R. M., et al., *Am. J. Vet. Res.* 54:1683–1692 (1993).
Dayhoff, M. O., *ATLAS OF PROTEIN SEQUENCE AND STRUCTURE*, suppl. 3, National Biomedical Research Foundation, Washington, D.C. (1978).
Doolittle, R. F., *OF URFs AND ORFs*, University Science Books (1986).
Flugelman, et al., *Circulation* 82:2217 (1990).
Fox, P. R., et al., *Am. J. Vet. Res.* 54:563–569 (1993).
Franz, W-M, et al., *Circ. Res.* 73:629 (1993).
Freese, A., et al., *Biochem. Pharm.* 40:2189 (1990).
Frei, B., *Am. J. Med.* 97 suppl 3A:5s-13s (1993)
Friedman, J. M., et al., *Mol. Cell Biol.* 6:3791–3797 (1986).
Fujisawa, H., et al., *J. Neurochem.* 63:140 (1994).
Fukamizu, A., et al., *Biochem. Biophys. Res. Commun.* 199:183 (1994).
Giallongo, A., et al., *Eur. J. Biochem.* 214:367 (1993).
Gorechi, et al., *Free Radic. Res. Commun.* 12–13:401 (1991).
Gottlieb, R. A., et al., *J. Clin. Invest.*, 94:1612–1628 (1994).
Graham, F. L., and Prevea, L., in *METHODS IN MOLECULAR BIOLOGY*, Vol. 7 (Murray, E. J., Ed.) (Humana, Clifton, N.J.) pp. 109–127 (1991).
Grunhaus, A. and Horowitz, M. S., *Semin. Virol.*, 3:237–252 (1992).
Gulick, J., et al., *J. Biol. Chem.* 266:9180–85 (1991).
Gustafson, T. A., et al., *Proc. Natl. Acad. Sci. U.S.A.* 84:3122–3126 (1987).
Hansen, P. R. and Stawaski, G., *Cardiovasc. Res.*, 28:565–569 (1994).
Heakock, C. S. and Sutherland, R. M. *Br. J. Cancer* 62:217–228 (1990).
Hertz, J., and Gerard, R. D., *Proc. Natl. Acad. Sci. U.S.A.*, 90:2812–2816 (1993).
Hockenbery, D. M., et al., *Nature* 348:334–336 (1990).
Hockenbery, D. M., et al., *Cell* 75:241 (1993).
Hope, T. J., et al., *J. Virol.* 66:1849 (1992).
Inoue, A., et al., *J. Biol. Chem.* 264:14954–14959 (1989).
Jaffe, H. A., et al., *Nat. Genet.* 1:374 (1992).
Jahrondi, N., and D. C. Lynch, *Mol. Cell. Biol.* 14:999–1008 (1994).
Jones, N., and Shenk, T., *Cell* 16:683 (1979).
Kasahara, N., et al., *Science* 266:1373 (1994).
Kass-Eisler, et al., *Proc. Natl. Acad. Sci.* 90:11498–11502 (1993).
Kennedy, P. G. and Steiner, I. *Q.J. Med.* 86:697–702 (1993).
Kirshenbaum, L. A., et al., *J. Clin. Invest.* 92:381 (1993).
Kitsis, R., et al., *Proc. Natl. Acad. Sci. U.S.A.* 88:4138 (1991).
Kourembanas, S., et al., *J. Clin. Invest.* 92:99 (1993).
Lantz, G. C., et al., *Am. J. Vet. Res.* 53:1594–1598 (1992).
Leclere, G., et al., *J. Clin. Invest.* 90:936 (1992).
Lefer, et al., *Circulation* 88:1779–1787 (1994).
Lin, H., et al., *Circulation* 82:2217 (1990).
Luke, M. C., et al., *J. Androl* 15:41 (1994).
Madan, A., et al., *Proc. Natl. Acad. Sci.* 90:3928 (1993).
Mahdavi, V., et al., *Proc. Natl. Acad. Sci.* 81:2626 (1984).
Malim, M. H., et al., *J. Exp. Med.* 176:1197 (1992).
Malin, M. H., et al., *Cell* 58:205 (1989).
Marci, P., et al., *Hum. Gene Ther.* 5:175 (1994).
Miller, A. D., *Hum. Gene Ther.* 1:5 (1990).
Miller, et al., *Vet. Clin. North Am. Anim. Pract.* 19:87–102 (1989).
Minty, A., and Kedes, L., *Mol. Cell Biol.* 6:2125–2136 (1986).
Molkentin, J. D., et al., *Mol. Cell Biol.* 144:947–4957 (1994).
Morishita, R., et al., *J. Clin. Invest.* 91:2580 (1993).
Mullis, K. B., et al., U.S. Pat. No. 4,683,195, issued 28 Jul. 1987.
Mullis, K. B., U.S. Pat. No. 4,683,202, issued Jul. 28, 1987.
Murtha, P., et al., *Biochem.* 32:6459 (1993).
Muscat, G. E. O, and Kedes, L., *Mol. Cell Biol.* 7:4089–4099 (1987).
Nabel, E. G., et al., *Science* 249:1285 (1990).
Nakane, M., et al., *FEBS Lett.* 316:175 (1993).
Peshavaria, M., and Day, I. N. M., *Biochem. J.* 275:427–433 (1991).
Quantin, B., et al., *Proc. Natl. Acad. Sci. U.S.A.* 89:2581 (1992).
Reimer, D. L., et al., *Genomics*, 21:325 (1994).
Rosenberg, M. E. and Paller, M. S. *Kidney International*, 39:1156–1161 (1991).

Rosenfeld, M. A., et al., *Science* 252:431 (1991).

Rosenfeld, M. A., et al., *Cell*, 68:143–155 (1992).

Rossi, J. J., and Sarver, N., *Adv. Exp. Med. Biol.* 312:95 (1992).

Sambrook, J., et al., *MOLECULAR CLONING: A LABORATORY MANUAL*, Second Edition, Cold Spring Harbor Laboratory (Cold Spring Harbor, N.Y.) (1989).

Sasaoka, T., et al., *Brain Res. Mol. Brain Res.* 16:274 (1992).

Schulz, G. E., et al., *PRINCIPLES OF PROTEIN STRUCTURE*, Springer-Verlag New York Inc. (1979).

Scott-Moncrieff, J. C., et al., *J. Am. Vet. Med. Assoc.* 201:1553–1558 (1992).

Semenza, G. L., and Wang, G. L., *Mol. Cell Biol.* 12:5447–5454 (1992).

Seto, M., et al., *EMBO J.* 7:123 (1988).

Smith, E. F., et al., *Am. J. Physiol.* 255:H1060-H1068 (1988).

Stratford-Perricaudet, L. D., et al., *J. Clin. Invest.* 90:626 (1992a).

Stratford-Perricaudet, L. D., et al., *Bone Marrow Transplant* 9(suppl. 1):151 (1992b).

Subramaniam, A., et al., *J. Biol. Chem.* 268:4331–4336 (1993).

Sullenger, B. A., et al., *J. Virol.* 65:6811 (1991).

Sullivan, K. E., et al., *Vet. Surg.* 22:343–350 (1993).

Takenaka, M., et al., *J. Biol. Chem.* 264:2363–2367 (1989).

Takiguchi, M., et al., *J. Biol. Chem.* 266:9186 (1991).

Thornton, J. D., et al., *J. Mol. Cell Cardiol.* 25:311 (1993).

Titus, D. E., ed., *PROMEGA PROTOCOLS AND APPLICATIONS GUIDE*, Second Edition, Promega Corporation (Madison, Wis.) (1991).

Tsujimoto, Y., et al., *Proc. Natl. Acad. Sci.* 83:5214–18 (1986).

Vibert, M., et al., *Eur. J. Biochem.* 181:33 (1989).

Wagner, E., et al., *Proc. Natl. Acad. Sci. U.S.A.* 89:6099 (1992a).

Wagner, E., et al., *Proc. Natl. Acad. Sci. U.S.A.* 89:7934 (1992b).

Webster, K. A., and Bishopric, N. H., *J. Mol. Cell Cardiol.* 24:741–751 (1992).

Webster, K. A. and Kedes, L., *Mol. Cell Biol.* 10:2402–2406 (1990).

Webster, K. A., et al., *J. Biol. chem.* 268:16852–16858 (1993).

Williams, G. T. and Smith C. A. *Cell*, 74:777–778 (1993).

Wilson, D. V., and Stick, J. A., *Am. J. Vet. Res.* 54:442–448 (1993).

Wolf, A., et al., *Science* 247:1465 (1990).

Wu, G. Y., *J. Biol. Chem.* 266:14338 (1991).

Youker, et al., *J. Clin. Invest.* 89:602–609 (1992).

Yung, W. K., *Curr. Opin. Oncol.* 6:235–239 (1994).

Zhang, L. X., et al., *Neuroreport*, 3:700 (1992).

BACKGROUND OF THE INVENTION

Each year, over a half-million Americans die from heart attacks. Even more—close to 700,000—have non-fatal heart attacks. For these surviving victims, a portion of the heart is usually damaged irreparably. Such cell death of cardiac tissue, called myocardial infarction, is due in large part to tissue damage caused by ischemia and/or ischemia followed by reperfusion.

Similar ischemic damage may occur in many other tissues when the blood supply to the tissue is reduced or cut off. Stroke, deep vein thrombosis, pulmonary embolus, and renal failure are examples.

Surviving victims of ischemic episodes, such as heart attacks, are at substantially greater risk for subsequent episodes of ischemia, which in many cases prove debilitating or fatal. Thus, it would be desirable to have therapeutic methods and compositions by which survivors of heart attacks and other types of ischemic insults could lower the risk of tissue damage due to recurrent ischemic/reperfusion episodes.

SUMMARY OF THE INVENTION

In one aspect, the invention includes a method for reducing ischemic injury to a cell exposed to hypoxic conditions. The method includes introducing into the cell a chimeric gene containing a hypoxia response element, a therapeutic gene, and a tissue-specific promoter operably linked to the therapeutic gene to control transcription of the therapeutic gene in the cell, where the element is effective to modulate expression of the therapeutic gene. Exposing the cell to hypoxic conditions enhances expression of the gene and expression of the gene is effective in reducing ischemic injury to the cell. The method may be applied to, for example, cardiac cells using a cardiac-specific promoter, kidney cells using a kidney-specific promoter, brain cells using a brain-specific promoter, and vascular endothelium cells using a vascular endothelium-specific promoter. The hypoxia response element may be selected from, for example, the erythropoietin HRE element (HREE1), muscle pyruvate kinase (PKM) HRE element, β-enolase (enolase 3; ENO3) HRE element and endothelin-1 (ET-1) HRE element. The therapeutic gene may be selected from, for example, nitric oxide synthase (NOS), B-cell leukemia/lymphoma 2 (bcl-2), superoxide dismutase (SOD) and catalase.

In a related aspect, the invention includes a chimeric gene, containing a hypoxia response element, a tissue-specific promoter heterologous to the element, and a therapeutic gene. The promoter is operably linked to the therapeutic gene and the element is effective to modulate expression of the therapeutic gene. The method may be used with a variety of cell types and corresponding promoters, for example, as identified above. Suitable cardiac-specific promoters include the $\alpha$-MHC$_{5.5}$ promoter, $\alpha$-MHC$_{86}$ promoter, and human cardiac actin promoter. Suitable kidney-specific promoters include the renin promoter. Suitable brain-specific promoters include the aldolase C promoter and the tyrosine hydroxylase promoter. Suitable vascular endothelium-specific promoters include the Et-1 promoter and vonWillebrand factor promoter. Hypoxia response enhancer element useful with the method include HREE1, PKM HRE element, ENO3 HRE element and ET-1 HRE element. Therapeutic genes useful with the method include NOS, Bcl-2, SOD and catalase. The chimeric gene may also be contained in an expression vector.

Another aspect of the present invention includes the above-described chimeric gene carried in an expression vector. The expression vector may be a plasmid, adenovirus vector, retrovirus vector, or the like.

In still another aspect, the invention includes a chimeric gene which contains a hypoxia response element, a tissue-specific promoter heterologous to the element, and a deleterious gene. The promoter is operably linked to the deleterious gene, and the element is effective to modulate expression of the deleterious gene. Suitable promoters include tumor-specific promoters, such as alpha fetoprotein (AFP) promoter. Suitable hypoxia response elements are as articulated above. Deleterious genes useful in this aspect include a viral thymidine kinase gene (tk), such as the herpes simplex virus (HSV) tk.

In a related aspect, the invention includes a method of causing injury to a cell exposed to hypoxic conditions. The method includes introducing into the cell a vector containing a hypoxia response element, a deleterious gene, and a tissue-specific promoter operably linked to the gene and capable of controlling transcription of the gene in the cell. Exposing the cell to hypoxic conditions enhances expression of the gene, and expression of the gene is effective to cause injury to the cell. Promoters useful with this method include tumor-specific promoters such as the AFP promoter. Specific hypoxia response elements and deleterious genes useful with the method are also as identified above.

The invention further includes a substantially isolated polynucleotide having a sequence corresponding to hypoxia response enhancer element(s) (HREE(s)) present in a control region of the muscle pyruvate kinase gene. The element may be derived from the promoter region, 5' untranslated region, or 3' untranslated region. In a related aspect, the invention includes an HRE element derived from a muscle pyruvate kinase gene.

Also included in the invention is a substantially isolated polynucleotide having a sequence corresponding to hypoxia response element(s) present in a control region of the endothelin-1 gene. The element may be derived from the promoter region, 5' untranslated region, or 3' untranslated region. In a related aspect, the invention includes an HRE element derived from an endothelin-1 gene.

Another aspect of the invention includes a substantially isolated polynucleotide having a sequence corresponding to hypoxia response element(s) present in a control region of the enolase 3 (ENO3) gene. The element may be derived from the promoter region, 5' untranslated region, or 3' untranslated region. In a related aspect, the invention includes an HRE element derived from an ENO3 gene.

These and other objects and features of the invention will become more fully apparent when the following detailed description is read in conjunction with the accompanying drawings.

BRIEF DESCRIPTION OF THE FIGURES

FIGS. 6A, 6B, 6C, 6D and 6E show a schematic diagram of the construction of plasmids pGLPKM$_{460}$ (FIG. 6C), pGLPKMD (FIG. 6D), and pGLPKM$_{285}$ (FIG. 6E) from plasmid pGL2BV (FIG. 6B) and a fragment of the PKM promoter (FIG. 6A; SEQ ID NO:7).

FIGS. 7A, 7B and 7C show a schematic diagram of the construction of plasmid pGLET-1$_{700}$ (FIG. 7C) from plasmid pGL2BV (FIG. 7B) and a fragment of the ET-1 promoter (FIG. 7A; SEQ ID NO:8).

BRIEF DESCRIPTION OF THE SEQUENCES

Figure 1A:
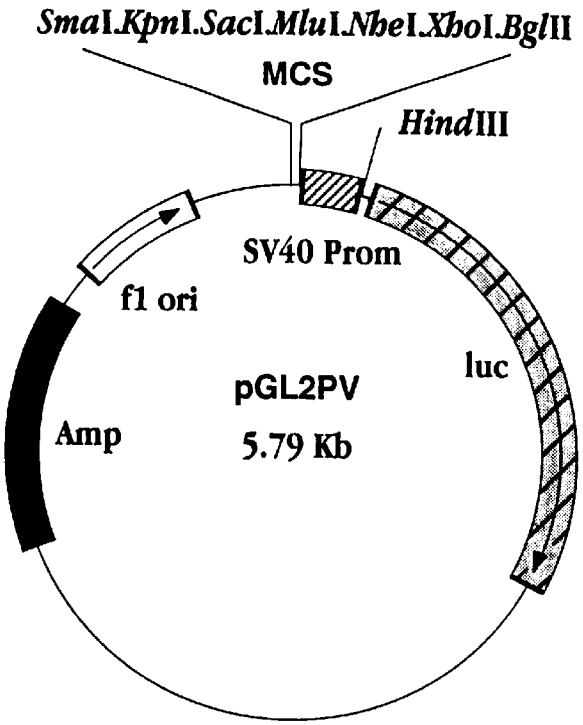
FIGS. 1A and 1B show a schematic diagram of the construction of plasmid pGLHRE (FIG. 1B) from plasmid pGL2PV (FIG. 1A).

SEQ ID NO:1 is the sense strand nucleotide sequence of a GATA4 enhancer element (Molkentin, et al., 1984).

SEQ ID NO:2 is the nucleotide sequence of muscle pyruvate kinase (PKM) sense strand primer F.

SEQ ID NO:3 is the nucleotide sequence of PKM reverse strand primer R.

SEQ ID NO:4 is the nucleotide sequence of endothelin-1 (Et-1) sense strand primer F.

SEQ ID NO:5 is the nucleotide sequence of Et-1 reverse strand primer R.

SEQ ID NO:6 is the nucleotide sequence of hypoxia response enhancer element 1 (HREE1), derived from the erythropoietin (EPO) gene (Semenza and Wang), and containing 4 tandem copies of a hypoxia response enhancer (HRE) sequence and cloning linkers.

SEQ ID NO:7 is the nucleotide sequence of a rat muscle pyruvate kinase (PKM) promoter region (Takenaka, et al.).

SEQ ID NO:8 is the nucleotide sequence of a human Et-1 promoter region (Inoue, et al.).

SEQ ID NO:9 is the nucleotide sequence of a human cardiac actin promoter region (Minty and Kedes).

SEQ ID NO:10 is a nucleotide sequence containing a portion of the rat cardiac α-myosin heavy chain promoter region (Mahdavi, et al.; GenBank Accession # K01464).

SEQ ID NO:11 is a nucleotide sequence containing a portion of the mouse cardiac α-myosin heavy chain promoter region (Gulick, J., et al.; GenBank Accession # M62404).

SEQ ID NO:12 is the nucleotide sequence of a human B-cell leukemia/lymphoma 2 (bcl-2) gene (Tsujimoto, et al.; GenBank Accession # M13994).

SEQ ID NO:13 is the predicted amino acid sequence from SEQ ID NO:12.

SEQ ID NO:14 is the nucleotide sequence of a rat nitric oxide synthase (bNOS) gene (Bredt et al.; EMBL Accession # X59949).

SEQ ID NO:15 is the predicted amino acid sequence from SEQ ID NO:14.

SEQ ID NO:16 is the nucleotide sequence of a human bcl-2 fusion gene (Seto, et al.; EMBL Accession # X06487).

SEQ ID NO:17 is the predicted amino acid sequence from SEQ ID NO:16.

SEQ ID NO:18 is the nucleotide sequence of a human NOS-1 gene (Fujisawa, et al.); DDBJ Accession # D16408; NCBI Seq ID 506339)

SEQ ID NO:19 is the predicted amino acid sequence from SEQ ID NO:18.

SEQ ID NO:20 is the nucleotide sequence of a human NOS-SN gene (Nakane, et al.; GenBank Accession # L02881)

SEQ ID NO:21 is the predicted amino acid sequence from SEQ ID NO:20.

SEQ ID NO:22 is the nucleotide sequence of a 256 base pair (bp) 3' EPO-1 hypoxia response enhancer element (Semenza and Wang).

SEQ ID NO:23 is the nucleotide sequence of a 42 bp 3' EPO-1 hypoxia response enhancer element (Madan, et al.).

SEQ ID NO:24 is the nucleotide sequence of an 86 bp rat αMHC promoter region.

SEQ ID NO:25 is the nucleotide sequence of a mouse catalase gene (Reimer, et al.; GenBank # L25069).

SEQ ID NO:26 is the predicted amino acid sequence from SEQ ID NO:25.

SEQ ID NO:27 is the nucleotide sequence of a human manganese superoxide dismutase (SOD) gene (Clair, et al.; EMBL # X59445).

SEQ ID NO:28 is the predicted amino acid sequence from SEQ ID NO:27.

SEQ ID NO:29 is the nucleotide sequence of a human β-enolase (ENO3) gene (Giallongo, et al.; EMBL # X56832) between nucleotides −628 to +63.

SEQ ID NO:30 is the predicted amino acid sequence from SEQ ID NO:29.

SEQ ID NO:31 is a consensus sequence of a region present in both the PKM and ENO3 promoters.

DETAILED DESCRIPTION OF THE INVENTION

Definitions

"Ischemia" is defined as an insufficient supply of blood to a specific organ or tissue. A consequence of decreased blood supply is an inadequate supply of oxygen to the organ or tissue (hypoxia). Prolonged hypoxia may result in injury to the affected organ or tissue. "Anoxia" refers to a virtually complete absence of oxygen in the organ or tissue, which, if prolonged, may result in death of the organ or tissue.

"Hypoxic condition" is defined as a condition under which a particular organ or tissue receives an inadequate supply of oxygen.

"Anoxic condition" refers to a condition under which the supply of oxygen to a particular organ or tissue is cut off.

"Reperfusion" refers to the resumption of blood flow in a tissue following a period of ischemia.

"Ischemic injury" refers to cellular and/or molecular damage to an organ or tissue as a result of a period of ischemia and/or ischemia followed by reperfusion.

An "element", when used in the context of nucleic acid constructs, refers to a region of the construct or a nucleic acid fragment having a defined function. For example, a hypoxia response enhancer element is a region of DNA that, when associated with a gene operably linked to a promoter, enhances the transcription of that gene under hypoxic conditions.

The term "operably linked", as used herein, denotes a relationship between a regulatory region (typically a promoter element, but may include an enhancer element) and the coding region of a gene, whereby the transcription of the coding region is under the control of the regulatory region.

Two nucleic acid elements are said to be "heterologous" if the elements are derived from two different genes, or alternatively, two different species. For example, a hypoxia response enhancer element from a human erythropoietin gene is heterologous to a promoter from a human myosin gene. Similarly, a hypoxia response enhancer element from a human erythropoietin gene, for example, is heterologous to a promoter from a mouse erythropoietin gene.

"Control region" refers to specific sequences at the 5' and 3' ends of eukaryotic genes which may be involved in the control of either transcription or translation. For example, most eukaryotic genes have an AT-rich region located approximately 25 to 30 bases upstream from the site where transcription initiation site. Similarly, most eukaryotic genes have a CXCAAT region (X may be any nucleotide) 70 to 80 bases upstream from the start of transcription. At the 3' end of most eukaryotic genes is an AATAAA sequence, which may be the signal for addition of the polyadenylation tail to the 3' end of the transcribed mRNA.

"Chimeric gene" also termed "chimeric DNA construct" refers to a polynucleotide containing heterologous DNA sequences, such as promoter and enhancer elements operably linked to a therapeutic gene. For example, a construct containing a human α-myosin heavy chain (α-MHC) promoter fragment operably linked to a human bcl-2 gene and containing a human erythropoietin gene hypoxia response element comprises an exemplary chimeric gene.

I. Overview of the Invention

The present invention relates to chimeric genes having at least three functional elements: (i) a therapeutic gene, (ii) a tissue-specific promoter, and (iii) a hypoxia response enhancer (HRE) element. The tissue-specific promoter in combination with the HRE element directs expression of the therapeutic gene in a selected tissue under hypoxic conditions.

The gene is preferably introduced into a target tissue as part of a complete expression vector in a pharmaceutically-acceptable vehicle, either by direct administration to the target tissue (e.g., injection into the target tissue), or by systemic administration (e.g., intravenous injection). In the latter case, the gene may be targeted to a selected tissue, for example, by incorporating it in a virion expressing a modified envelope protein designed to bind to receptors preferentially expressed on cells from the selected, or targeted, tissue. Regardless of the delivery means, expression of the gene in tissues other than the target tissue, and under conditions other than hypoxic or anoxic is preferably minimal.

As described below, a variety of therapeutic genes, promoters, HRE elements and gene delivery means may be employed in the practice of the present invention.

II. Tissue Specific Promoters

A promoter, in the context of the present specification, refers to a polynucleotide element capable of regulating the transcription of a gene adjacent and downstream (3') of the promoter. The promoter may contain all of, or only a portion of, the complete 5' regulatory sequences of the gene from which it is derived. A sequence in the promoter region is typically recognized by RNA polymerase molecules that start RNA synthesis.

A promoter may be functional in a variety of tissue types and in several different species of organisms, or its function may be restricted to a particular species and/or a particular tissue. Further, a promoter may be constitutively active, or it may be selectively activated by certain substances (e.g., a tissue-specific factor), under certain conditions (e.g., hypoxia, or the presence of an enhancer element in the chimeric gene containing the promoter), or during certain developmental stages of the organism (e.g., active in fetus, silent in adult).

Promoters useful in the practice of the present invention are preferably tissue-specific—that is, they are capable of driving transcription of a gene in one tissue while remaining largely "silent" in other tissue types. It will be understood, however, that tissue-specific promoters may have a detectable amount of "background" or "base" activity in those tissues where they are silent. The degree to which a promoter is selectively activated in a target tissue can be expressed as a selectivity ratio (activity in a target tissue/activity in a control tissue). In this regard, a tissue specific promoter useful in the practice of the present invention typically has a selectivity ratio of greater than about 5. Preferably, the selectivity ratio is greater than about 15.

It will be further understood that certain promoters, while not restricted in activity to a single tissue type, may nevertheless show selectivity in that they may be active in one group of tissues, and less active or silent in another group. Such promoters are also termed "tissue specific", and are contemplated for use with the present invention. For example, promoters that are active in a variety of central nervous system (CNS) neurons may be therapeutically useful in protecting against damage due to stroke, which may effect any of a number of different regions of the brain.

Tissue-specific promoters may be derived, for example, from promoter regions of genes that are differentially expressed in different tissues. For example, a variety of promoters have been identified which are suitable for upregulating expression in cardiac tissue. Included are the cardiac α-myosin heavy chain (AMHC) promoter and the cardiac α-actin promoter.

A further desirable characteristic of promoters useful in the present invention is that they possess a relatively low activity in the absence of activated hypoxia-regulated enhancer elements, even in the target tissues. One means of achieving this is to select promoters of genes encoding proteins that have a relatively low turnover rate in adult tissue, such as the actin and α-MHC promoters described herein. Another means is to use "silencer" elements, which suppress the activity of a selected promoter in the absence of hypoxia.

The level of expression of a gene under the control of a particular promoter can be modulated by manipulating the promoter region. For example, different domains within a promoter region may possess different gene-regulatory activities. The roles of these different regions are typically assessed using vector constructs having different variants of the promoter with specific regions deleted (i.e., deletion analysis). Vectors used for such experiments typically contains a reporter gene, which is used to determine the activity of each promoter variant under different conditions. Application of such a deletion analysis enables the identification of promoter sequences containing desirable activities.

This approach may be used to identify, for example, the smallest region capable of conferring tissue specificity, or the smallest region conferring hypoxia sensitivity.

A number of tissue specific promoters, described below, may be particularly advantageous in practicing the present invention. In most instances, these promoters may be isolated as convenient restriction digest fragments suitable for cloning into a selected vector.

Alternatively, promoter fragments may be isolated using the polymerase chain reaction (PCR; Mullis, Mullis, et al.). Cloning of amplified fragments may be facilitated by incorporating restriction sites at the 5' ends of the primers.

Promoters suitable for cardiac-specific expression include the promoter from the murine cardiac α-myosin heavy chain gene. The gene contains a 5.5 kbp promoter region which may be obtained as a 5.5 kbp SacI/SalI fragment from the murine αMHC gene (Subramaniam, et al., 1991). Reporter gene constructs utilizing this 5.5 kbp αMHC promoter are expressed at relatively high levels selectively in cardiac tissue (whether or not an HREE is present) and, when present in transgenic animals, are regulated in a similar fashion to the endogenous gene (Subramaniam, et al., 1991).

A smaller fragment of the rat α-MHC promoter may be obtained as a 1.2 kbp EcoRI/HindIII fragment (Gustafson, et al.). As shown in Example 1 and Table 1, below, constructs utilizing the 1.2 kbp rat αMHC promoter are expressed at a low level in the absence of an HREE, and at an intermediate level in the presence of an HREE. These results indicate that the $\alpha MHC_{1.2}$ promoter is an exemplary promoter to target expression of chimeric genes of the present invention to cardiac tissue. Expression of genes under the control of this promoter fragment is very low in cardiac cells under normal oxygenation conditions, but is increased by about a factor of four under hypoxic conditions when the construct contains HREE1. Expression in cells other than cardiac cells is at background levels.

An 86 bp fragment of the rat αMHC promoter, presented herein as SEQ ID NO:24, restricts expression of reporter genes to cardiac and skeletal muscle (i.e., it has lost some tissue selectivity). Additional cardiac specificity may be conferred to the fragment by ligating (e.g., blunt end ligating) a 36-mer oligonucleotide (SEQ ID NO:1) containing cardiac-specific GATA4 enhancer elements just upstream of base pair −86 (Molkentin, et al., 1984). This promoter fragment also results in low levels of expression in the absence of additional enhancers such as HRE elements. The low level of basal expression induced by the 86 bp fragment, and the ability to upregulate this basal level of expression with a hypoxia response enhancer element are useful properties for a promoter for use with the present invention.

The sequences of exemplary cardiac-specific promoter regions from the rat and mouse AMHC genes are presented herein as SEQ ID NO:10 and SEQ ID NO:11, respectively. Both sequences end just upstream of the ATG initiation codons of their respective genes. Other cardiac-specific promoters include the cardiac α-actin promoter and the myosin light chain-2 (MLC-2) promoter. Constructs described herein utilizing a 118 bp fragment (SEQ ID NO:9) from the human cardiac α-actin (HCA) promoter result in a relatively low level of cardiac-specific expression, which may be increased by the inclusion of an HREE in the expression construct (Example 1, Table 1). The cardiac-specific myosin light chain-2 promoter may be obtained as a 2.1 kbp KpnI/EcoRI fragment from the rat cardiac myosin light chain-2 (MLC-2) gene (Franz, et al.).

Prostate-specific promoters include the 5'-flanking regions of the human glandular kallikrein-1 (hKLK2) gene and the prostate-specific antigen (hKLK3; PSA) gene (Murtha, et al.; Luke, et al.). The renin promoter is suitable for directing kidney-specific expression (Fukamizu, et al.), while the aldolase-C promoter (Vibert, et al.) or the tyrosine hydroxylase promoter (Sasaoka, et al.) may be used to direct expression in the brain. Promoters specific for vascular endothelium cells include the Et-1 promoter (Inoue, et al.) and vonWillebrand factor (Jahrondi and Lynch) promoter.

Tumor-specific promoters include the α-fetoprotein (AFP) promoter, contained in a 7.6 kbp fragment of 5'-flanking DNA from the mouse AFP gene (Marci, et al.). This promoter normally directs expression of the AFP gene in fetal liver and is transcriptionally silent in adult tissues. However, it can be abnormally reactivated in hepatocellular carcinoma (HCC), conferring tumor-specific expression in adult tissue (Marci, et al.).

The above promoters are exemplary promoters for use with the present invention. Other promoters suitable for use with the present invention may be selected by one of ordinary skill in the art following the guidance of the present specification.

III. Hypoxia Response Enhancer Elements

Therapeutic genes contained in constructs of the present invention are preferably expressed at low levels, if at all, under conditions of normal oxygenation (minimizing any side effects). Under conditions of hypoxia, however, expression of the genes is increased, affording protection to the target tissue. The elevated expression under hypoxic conditions is conferred by the presence of one or more hypoxia response enhancer (HRE) elements.

HRE elements contain polynucleotide sequences that may be located either upstream (5') or downstream (3') of the promoter and/or therapeutic gene. The HRE element (HREE) is typically a cis-acting element, usually about 10–300 bp in length, that acts on a promoter to increase the transcription of a gene under the control of the promoter. Preferably, the promoter and enhancer elements are selected such that expression of a gene regulated by those elements is minimal in the presence of a healthy supply of oxygen, and is upregulated under hypoxic or anoxic conditions.

Hypoxia response enhancer elements are found in association with a number of genes, including the erythropoietin (EPO) gene. Exemplary HRE elements from the EPO gene are presented herein as SEQ ID NO:6, SEQ ID NO:22 and SEQ ID NO:23. The element having the sequence represented as SEQ ID NO:22 results in approximately a five-fold induction of reporter gene expression under hypoxic conditions (Semenza and Wang), while, the element having the sequence represented as SEQ ID NO:23 results in approximately a 17-fold increase in activity under hypoxic conditions (Madan, et al.)

Experiments performed in support of the present invention (e.g., Example 1) demonstrate that expression of constructs containing HREE1 (SEQ ID NO:6) is increased by approximately 5- to 7-fold in response to hypoxic conditions. These results indicate that the HREE1 element is fully functional when fused to muscle and cardiac specific promoters and that muscle and cardiac cells are fully responsive to hypoxia in terms of the regulation of these promoters.

Expression of constructs containing a fragment (SEQ ID NO:29) from the control region of the enolase 3 (ENO3) gene was induced approximately 5 to 8 fold by hypoxia in C2C12 cells and cardiac myocytes respectively (see Table 1). These results suggest that the HREE in the ENO3 promoter fragment may be a particularly effective HREE for hypoxia induction in constructs containing a tissue-specific promoter, such as a cardiac or skeletal muscle promoter.

According to the present invention, exemplary hypoxia response enhancer elements may also be isolated from regulatory regions of both the muscle glycolytic enzyme pyruvate kinase (PKM) gene (Takenaka, et al.), the human muscle-specific β-enolase gene (ENO3; Peshavaria and Day), and the endothelin-1 (ET-1) gene (Inoue, et al.). The HRE regions from the PKM gene and the ET-1 gene, identified in experiments performed in support of the present invention (see Materials and Methods, Examples 4 and 5), are presented herein as SEQ ID NO:7 and SEQ ID NO:8, respectively.

Example 4 demonstrates that the expression of pGLPKM, a plasmid containing the HRE element from the PKM gene, in transfected C2C12 myotubes and neonatal cardiac myocytes was increased by 6±2 (n=4) fold in both cell types by incubation of the cells in a hypoxic atmosphere. A portion of this HRE element, obtained by digesting with SmaI to cut at an internal SmaI site, localized the hypoxia response sequence to a 200 bp fragment. This fragment, termed $HREPKM_{285}$, confers hypoxia-induced expression in C2C12 myotubes and cardiac myocytes that is at least equivalent to that obtained using HREE1 (SEQ ID NO:6).

Both PKM and ENO3 promoters contain a common sequence element (SEQ ID NO:31) located at 5' −88 and −70 bp respectively from the transcription start sites. An oligonucleotide containing this sequence may be sufficient to confer hypoxia response characteristics to constructs of the present invention.

Data presented in Example 5 show that expression of $pGLET-1_{700}$, containing 700 bp of the human ET-1 gene promoter (SEQ ID NO:8), in transfected human arterial endothelial cells was increased approximately 5 -fold by incubation of the cells in a hypoxic atmosphere. No hypoxia-induced increase in $pGLET-1_{700}$ expression was seen in other cell types, including HeLa cells, C2C12 cells, and cardiac myocytes. Accordingly, the 700 bp fragment may be used to target hypoxia regulated genes specifically to cells of the vascular endothelium, since the fragment contains element(s) conferring tissue specificity (i.e., elements effective to target expression exclusively to the vascular endothelium), as well as HRE element(s) effective to upregulate transcription of a gene under control of the fragment during hypoxic conditions.

It will be appreciated that the present invention includes the use of HRE elements not explicitly identified above. Additional HRE elements may be identified, for example, as detailed in Examples 4 and 5. Further, promoter deletion and mutation analyses (e.g., as described above and in Webster and Kedes) may be used to identify such elements in other hypoxia responsive genes. A number of such responsive target genes have been shown to be induced when cells are exposed to hypoxia in vitro (e.g., Heakock and Sutherland).

It will also be appreciated that, in certain circumstances, the tissue-specific promoter and the hypoxia response enhancer element(s) of the present invention may be derived from a contiguous polynucleotide sequence from a single gene (e.g., as shown above for the ET-1 promoter region, which contains HRE element(s) and also imparts endothelial cell-specific expression).

IV. Therapeutic Genes

The present invention may be used to alleviate a number of disease conditions resulting from hypoxic and/or anoxic conditions due to ischemia where cell and tissue damage results from ischemia and ischemia followed by reperfusion. The invention is particularly suitable in cases where the subject is diagnosed to be at risk for an ischemic episode in a particular tissue.

For example, it is recognized that virtually all surviving heart attack victims are at significantly increased risk for recurrent episodes of myocardial ischemia. Such subjects would benefit from the introduction of constructs capable of expressing therapeutic genes into their cardiac tissue in order to decrease the risk of injury to the tissue during any subsequent ischemic episodes. Such constructs may serve to protect, for example, cardiac and vascular endothelial tissues from ischemic damage and thereby prevent the progression of the heart disease.

Recurrent ischemia and reperfusion typically results in oxidative damage to cells from reactive oxygen species (free radicals), such as peroxides, that are generated during redox switching (Frei). Contact of fresh blood with damaged or dead cells induces the influx of neutrophils, or pus cells, which kill heart cells which would otherwise have recovered. Much of the damage caused by neutrophils has been attributed to superoxide ions. The superoxide anion can damage tissue in several ways. The interaction of the superoxide anion with hydrogen peroxide leads to the production of hydroxyl radicals which are potentially toxic and react rapidly with most organic molecules. Lipids, proteins, and nucleic acids may all be primary targets for such oxidative damage. The extent and type of damage depend on the severity and nature of the hypoxic stress. For example, the stress may cause cellular damage, initiating an inflammatory response with neutrophil attack and subsequent tissue necrosis. Alternatively, the stress may initiate apoptosis (programmed cell death) to eliminate the damaged cells.

Regardless of the mechanism by which tissue death occurs (necrosis or apoptosis), the damage caused by ischemia-reperfusion episodes is typically the result of redox reactions and is quantitatively related to the severity and duration of the ischemia. For example, in the case of the myocardium, a severe heart attack may result in extensive damage (e.g., infarction of 30% to 40% of the left ventricle), whereas moderate angina and silent repetitive ischemia may result in relatively minor damage during each episode.

While the pathology of ischemia in tissues is complex, resulting in multiple potential targets for therapeutic intervention, several classes of targets are particularly suitable for therapeutic intervention in accordance with the teachings of the present invention. These include antioxidant systems, that may intervene immediately at the sites of intracellular redox reactions to minimize damage, and vasodilator systems, that may minimize the severity of the ischemia by increasing blood flow to vulnerable tissues. Antioxidant proteins amenable for use with the present invention include gene products of Bcl-2, catalase and superoxide dismutase (SOD) genes, while proteins with vasodilative properties include nitric oxide synthase (NOS), which produces the vasodilator nitric oxide (NO).

Bcl-2, an integral inner mitochondrial membrane protein of relative molecular mass ~25 kDa, has been shown to protect certain cells against apoptosis (Hockenbery, et al., 1990) by acting as an antioxidant (Hockenbery, et al., 1993). Bcl-2 may be an effective therapeutic gene for reducing damage to tissues during ischemic episodes because apoptosis may be a common response of many tissues, including the heart, to oxidative stress (Williams and Smith; Gottlieb, et al.

The enzyme superoxide dismutase (SOD) catalyzes the decomposition of the superoxide anion to peroxide. Enzymes such as superoxide dismutase, free radical scavengers or agents which prevent the influx on neutrophils are able to increase the salvage of heart muscle cells. The enzyme catalase in turn catalyzes the conversion of peroxides to water. Exemplary sequences of a SOD gene and a catalase gene are presented herein as SEQ ID NO:27 and SEQ ID NO:25, respectively. The sequence presented herein as SEQ ID NO:27 encodes a manganese SOD, which has a relatively long half-life. A related sequence, of a human Cu/Zn SOD, may be found in Gorechi, et al. The Cu/Zn SOD has a shorter half-life than the manganese SOD.

Endothelial-derived nitric oxide (NO) regulates the expression of vasoconstrictors and growth factors by the vascular endothelium (Kourembanas, et al.). Under hypoxia, endothelial cells typically increase expression and secretion of endothelin-1 (ET-1), a potent vasoconstrictor. This increase in expression can be reduced or prevented by exposure to NO (Kourembanas, et al.). One of the effects of ET-1 induced vasoconstriction is decreased blood flow to the affected organ or tissue, which can exasperate hypoxic damage due to ischemia. According to the present invention, such damage may be reduced by providing NO to the affected tissue through the expression of a NOS gene under the control of a vascular epithelium or cardiac-specific promoter and hypoxia response enhancer element.

Therapeutic genes of the present invention may be preferably derived from the same or related species as the one to which the methods and compositions of the present invention are applied. For example, for therapeutic treatment of a dog, it may be desirable to utilize a construct containing a therapeutic gene cloned from a dog. Similarly, for treatment of human conditions, it may be desirable to utilize therapeutic genes cloned from human-derived nucleic acids.

The genes encoding the proteins discussed above represent exemplary therapeutic genes useful in the practice of the present invention. It will be appreciated, however, that following the teachings and guidance of the present specification, one of skill in the art may select other therapeutic genes effective to reduce cellular damage due to hypoxia or ischemia, and that the use of such genes is considered to be within the scope of the present invention.

V. Deleterious Genes

In another aspect, the present invention includes constructs containing deleterious genes, rather than therapeutic genes. Expression of the deleterious genes is targeted to tissues which are harmful (e.g., malignant tumors) or otherwise undesirable. Promoters and hypoxia response elements may be selected as described above. Promoters useful in this aspect of the invention preferably restrict expression only to the undesirable tissue. For example, as discussed above, the AFP promoter can be activated in hepatocellular carcinoma (HCC), conferring tumor-specific expression in adult tissues (Marci, et al.).

Deleterious genes include a viral thymidine kinase gene (tk), such as the herpes simplex virus (HSV) tk. This gene is not deleterious by itself, but when expressed, viral TK can phosphorylate ganciclovir (GCV), turning GCV into a cytotoxic compound. Since tumor cells are typically hypoxic, constructs having a tumor-specific promoter operably linked to a viral tk and an HREE may be used in conjunction with GCV to selectively kill tumor cells.

VI. Expression Vectors

Chimeric genes of the present invention are preferably incorporated into expression vectors capable of expressing a therapeutic gene product in a selected eukaryotic host cell (i.e., a target tissue). Such expression vectors may contain, in addition to the chimeric gene, various other sequences useful for effective expression of the therapeutic gene in selected tissues. Such sequences may include, for example, sequences necessary for the termination of transcription. These sequences are transcribed as polyadenylated segments in the untranslated portion of the MRNA encoding the desired therapeutic protein. The 3' untranslated regions may also include transcription termination sites.

Molecular techniques and methods useful in the construction of expression vectors are well known in the art (e.g., Ausubel, et al., Sambrook, et al.). Vector constructs made in support of the present invention are designed to express either a reporter gene (e.g., luciferase), or therapeutic genes (e.g., Bcl-2 or NOS). Therapeutic gene expression is under the control of either a ubiquitous promoter (e.g., SV40), or a tissue-specific promoter (e.g., striated muscle or cardiac-specific promoter). Further regulation of expression by hypoxia or anoxia is provided by inclusion of hypoxia response enhancer (HRE) elements (e.g., from the erythropoietin (EPO) gene, muscle specific pyruvate kinase (PKM) gene, enolase 3 (ENO3) gene or the endothelial cell endothelin-1 (Et-1) gene).

The generation of exemplary constructs is described in the Materials and Methods section, below. The results of in vitro experiments to assess the performance of constructs having HREE1 and tissue specific promoters are presented in Example 1 and Table 1. The relative amount of gene expression was measured using a reporter gene (luciferase) in place of a therapeutic gene.

The data shown in Table 1 demonstrate that cells containing constructs having a hypoxia response enhancer element, such as HREE1, in combination with a compatible promoter, express the reporter at levels that are 5 to 7 times greater under hypoxic conditions than under aerobic conditions, and that HREE1 is equally active in different cells and independent of the promoter. The data also demonstrate that expression of constructs containing α-MHC promoters is cardiac specific, and that the basal (aerobic) expression from α-$MHC_{1.2}$ and HCA promoters is relatively low. Further, the data indicate that muscle and cardiac cells are fully responsive to hypoxia in terms of the regulation of these promoters.

In vivo experiments conducted with plasmids pGLHRE and pGLHCA$_{118}$HRE (Example 2, Table 2) demonstrate that gene expression in hearts of rats injected with the plasmids and subjected to ischemia was approximately 2-fold higher than expression in hearts from control animals (not subjected to ischemia). These results indicate that the direct injection of therapeutic constructs of the present invention into cardiac tissue in vivo is effective to result in the expression of genes carried on those plasmids. Further, these results indicate that expression vectors carrying chimeric genes of the present invention are effective to result in significantly increased levels of expression in response to hypoxia caused by ischemia in vivo.

Since expression was measured at 20 hours after a brief (20 minute) episode of ischemia, it will be appreciated that (i) hypoxia-induced expression may peak significantly earlier than 20 hours, and (ii) repeat ischemic episodes may upregulate expression more the single experimental episode used herein. Accordingly, the 2-fold induction may be an underestimate of the level of enhancement of transcription/expression caused by ischemia.

While the experiments described above were performed with cardiac tissue, it will be appreciated that one of ordinary skill in the art having the benefit of the present specification may perform similar manipulations with other tissues subject to ischemic and or ischemic/reperfusion injury, and that such procedures are within the scope of the present invention.

In vitro experiments (Example 3) demonstrate that cells transfected with reporter (pGLHRE, pGLHCA$_{118}$HRE, pGLαMHC$_{1.2}$HRE) and therapeutic (pSFFV-Bcl-2 and pNOS-HRE) constructs appear normal and respond to stimuli as expected. Reporter-transfected cells differentiate normally and respond to hypoxia with the predicted induction of reporter, while NOS and bcl-2-transfected cells appear normal both during the hypoxia and during subsequent reoxygenation. These results suggest that inclusion of HRE elements, Bcl-2 over-expression, and hypoxia-induced over-expression of NOS is not toxic or deleterious to muscle cells in vitro.

These results also suggest that expression vectors carrying therapeutic genes of the present invention may be effective to protect tissues from ischemic damage. Such protective effects may be assayed in an animal model by, for example, infecting myocardial tissue with an expression vector containing a chimeric gene of the present invention, such as an adenoviral vector expressing a therapeutic gene (e.g., Bcl-2 or SOD), a cardiac-specific promoter, and an HRE element, as described, for instance, in Example 2.

Following infection, the animals may be subjected to repeat ischemic episodes (e.g., 30 minutes to 1 hour) followed by reperfusion (e.g., 1 to 8 hours). Following the last reperfusion, the animals may be sacrificed and the ischemic regions of the myocardium may be tested for the presence and extent of infarction as described, for example, by Thornton, et al., and for the presence of apoptosis as described, for example, in Gottlieb, et al. Sample biopsies may also be assayed for expression of the therapeutic gene by Northern blots.

Similar experiments may be performed using constructs direct (e.g., via an appropriate promoter) to other tissues, such as brain, kidney and vascular endothelium.

VII. Delivery of Constructs to Cells and Tissues

Any of a variety of methods known to those skilled in the art may be used to introduce chimeric genes of the present invention into selected target tissue cells. For example, gene therapy of cardiac tissue has included lipofection, retrovirus and adenovirus-mediated gene transfer, and injection of naked DNA directly into the vascular endothelium or cardiac tissue (Nabel, et al.; Lin, et al.; Leclere, et al.; Flugelman, et al.). These and other methods are discussed more fully in the sections below.

Viral-Mediated Gene Transfer.

Host cells may be transfected with chimeric genes of the present invention by infection with mature virions containing hybrid vectors (the chimeric genes along with selected viral sequences). The virions used to transfect host cells are preferably replication-defective, such that the virus is not able to replicate in the host cells.

The virions may be produced by co-infection of cultured host cells with a helper virus. Following coinfection, the virions are isolated (e.g., by cesium chloride centrifugation) and any remaining helper virus is inactivated (e.g., by heating). The resulting mature virions contain a chimeric gene of the present invention and may be used to infect host cells in the absence of helper virus. Alternatively, high titers of replication-defective recombinant virus, free of helper virus, may be produced in packaging cell lines containing those components for which the virus is defective (Miller).

Several types of viruses, including retroviruses, adeno-associated virus (AAV), herpes virus, vaccinia virus, and several RNA viruses may be amenable for use as vectors with chimeric gene constructs of the present invention. Each type of virus has specific advantages and disadvantages, which are appreciated by those of skill in the art. Methods for manipulating viral vectors are also known in the art (e.g., Grunhaus and Horowitz; Hertz and Gerard; and Rosenfeld, et al.)

Retroviruses, like adeno-associated viruses, stably integrate their DNA into the chromosomal DNA of the target cell. Unlike adeno-associated viruses, however, retroviruses typically require replication of the target cells in order for proviral integration to occur. Accordingly, successful gene transfer with retroviral vectors depends on the ability to at least transiently induce proliferation of the target cells.

Retroviral vectors are attractive in part due to the efficiency of transfection—some vectors can stably transduce close to 100% of target cells. The use of retroviral vectors for in vivo gene therapy has been limited, in part, by the requirement of appropriate viral receptors on the target cell. Because the identities of most retroviral receptors are unknown, it has not been possible to determine the distribution of receptors in different cell types. Accordingly, the targeting of specific cell types by retroviral vectors has in many cases proven problematic.

This difficulty may be circumvented by modifying the envelope protein of the retrovirus to contain a ligand for a known endogenous (not necessarily viral) receptor expressed on the target cells. An application of this technique is described in detail by Kasahara. Preferably, the virus also contains an unmodified envelope protein to facilitate cell entry. A number of receptors, such as desmin, E-selectin, and A-CAM, are expressed preferentially on cardiac cells and may be amenable to this approach (e.g., Hansen and Stawaski; Lefer, et al.; Youker, et al.).

Adeno-associated viruses are capable of efficiently infecting nondividing cells and expressing large amounts of gene product. Furthermore, the virus particle is relatively stable and amenable to purification and concentration. Replication-defective adenoviruses lacking portions of the E1 region of the viral genome may be propagated by growth in cells engineered to express the E1 genes (Jones and Shenk; Berkner; Graham and Prevea). Most of the currently-used adenovirus vectors carry deletions in the E1A-E1B and E3 regions of the viral genome. A number of preclinical studies using adenoviral vectors have demonstrated that the vectors are efficient at transforming significant fractions of cells in vivo, and that vector-mediated gene expression can persist for significant periods of time (Rosenfeld, et al.; Quantin, et al.; Stratford-Perricaudet, et al., 1992a; Rosenfeld, et al.; L. D. Stratford-Perricaudet, et al., 1992b; Jaffe, et al.). Several studies describe the effectiveness of adenovirus-mediated gene transfer to cardiac myocytes (Kass-Eisler, et al.; Kirshenbaum, et al.).

Herpes virus vectors (Breakefield and DeLuca; Freese, et al.) are particularly well suited for the delivery and expression of foreign DNA in cells of the central nervous system (CNS), since they can efficiently infect mature, postmitotic neurons. Methods for manipulating the vectors and transfecting CNS cells are well known (see, e.g., Kennedy and Steiner; Yung). A number of studies describe methods for transplanting genetically modified cells into different regions of the brain (Malim, et al.; Rossi and Sarver; Sullenger, et al.; Morgan, et al.; Chatterjee, et al.; Malin, et al.; Hope, et al.). Studies utilizing direct injection of vectors into CNS tissue have also been performed (e.g., Zhang, et al.).

Naked DNA Injection

Plasmids bearing chimeric genes of the present invention may be purified and injected directly into a target tissue, as exemplified in Example 2 for rat cardiac tissue. The data discussed in Example 2 demonstrate that cardiac injection of plasmid suspended in saline buffer is effective to result in expression of the plasmid in the cardiac cells. Similar approaches have been used successfully by others to express, for example, exogenous genes in rodent cardiac and skeletal muscle (Wolf, et al.; Ascadi, et al., 1991a; Ascadi, et al., 1991b; Lin, et al.; Kitsis, et al..

Liposome-Mediated Gene Transfer

Liposomes may be employed to deliver genes to target tissues using methods known in the art. The liposomes may be constructed to contain a targeting moiety or ligand, such as an antigen, an antibody, or a virus on their surface to facilitate delivery to the appropriate tissue. For example, liposomes prepared with ultraviolet (UV) inactivated Hemagglutinating Virus of Japan (HVJ) may be used to deliver DNA to selected tissues (Morishita, et al.).

The liposomes may also be surface-coated, e.g., by incorporation of phospholipid—polyethyleneglycol conjugates, to extend blood circulation time and allow for greater targeting via the bloodstream. Liposomes of this type are well known.

Receptor-Mediated Gene Transfer

Receptor-mediated endocytic pathways for the uptake of DNA may permit the targeted delivery of genes to specific cell types in vivo. Receptor-mediated methods of gene transfer involve the generation of complexes between plasmid DNA and specific polypeptide ligands (Wu) that can be recognized by receptors on the cell surface. One of the problems with receptor-mediated uptake for gene delivery is that the endocytic vesicles formed during this process may be transported to the lysosome, where the contents of the endosome are degraded. Methods have been developed to facilitate escape of the DNA from the endosome during the course of its transport. For example, either whole adenovirus (Wagner, et al., 1992a; Christiano, et al.) or fusogenic peptides of the influenza HA gene product (Wagner, et al., 1992b) may be used to induce efficient disruption of DNA-containing endosomes.

Administration of Constructs

In cases such as those outlined above, where a vector may be targeted to selectively transfect a specific population of cells, it will be understood that in addition to local administration (such as may be achieved by injection into the target tissue), the vector may be administered systemically (e.g., intravenously) in a biologically-compatible solution or pharmaceutically acceptable delivery vehicle. Vector constructs administered in this way may selectively infect the target tissue. According to the present invention, the presence of a target tissue-specific promoter on the construct provides an independent means of restricting expression of the therapeutic gene.

VIII. Applications

A. Therapeutic Applications

Compositions and methods of the present invention may be useful to prevent tissue damage and/or death, due to ischemia and/or subsequent reperfusion, in a variety of tissues. As stated above, an exemplary application is in the reduction of damage due to recurrent myocardial ischemia following a heart attack. The expression of therapeutic genes in the cardiac tissue of heart attack victims may decrease the risk of injury to the tissue during any subsequent ischemic episodes.

Similarly, subjects who have been diagnosed with transient cerebral ischemia, blood clots or other risk factors for stroke may benefit from the use of hypoxia-inducible brain-specific constructs. Subjects diagnosed with acute or chronic renal failure are at greater risk for further ischemic damage to the kidneys (e.g., Rosenberg and Paller). Such subjects may benefit from a therapeutic gene under the control of a kidney-specific promoter, expression of which is enhanced by hypoxic conditions. A variety of other tissues diagnosed as "at risk" for ischemia may be similarly protected, as will be appreciated by one of skill in the art having the benefit of the present specification.

In addition to the utilities discussed above, compositions (e.g., expression vectors containing chimeric genes of the present invention) and methods of the present invention also have a number of applications in animal medicine. Although animals do not usually develop classical atherosclerosis, cardiomyopathies are very common. A number of species develop ischemia-related syndromes, including arteritis, vasculitis, and related vasculopathies, that result in direct redox damage to cells and tissues, particularly to vascular walls and myocardial tissues. Such conditions may be alleviated by administration of chimeric genes of the present invention.

A common and serious condition in horses and ponies involves ascending colonic ischemia, usually caused by strangulation obstruction (Dabareiner, et al.; Sullivan, et al.; Wilson and Stick). A related disease in dogs is called gastric dilation-volvulus (Lantz, et al.). Treatment of these disorders typically involves surgical removal of the obstruction. Reperfusion following such surgery can result in significant injury to reperfused tissues, and typically triggers an inflammatory response with progressive tissue necrosis. The reperfusion may also results in death of the animal due to cardiogenic shock. Compositions and methods of the present invention may be used therapeutically to treat such conditions, and to provide protection to vulnerable tissues, including heart and vascular endothelium, during the treatment of the above syndromes.

Another utility of the present invention is the treatment of cardiac disease in cats and dogs (Miller, et al.). A variety of forms of cardiovascular disease have been described in both cats and dogs, including dilated cardiomyopathy, left ventricular hypertrophy, and hyperthyroidism (Fox, et al.; Atkins, et al.). Systemic necrotizing vasculitis, a condition that may be analogous to atherosclerosis in humans (with regard to plaque formation and intimal proliferation), has been described in Beagles (Scott-Moncrieff, et al.). Each of these conditions may involve ischemia and reperfusion redox injuries to cardiac and vascular tissue that may be treated using the methods and compositions of the present invention.

B. Reporter Constructs for Diagnostic Applications

The present invention may also be employed in diagnostic applications, where it is desirable to localize the site of hypoxia or anoxia. According to this aspect of the invention, therapeutic genes are replaced by reporter genes, such as those used in experiments performed in support of the present invention (e.g., luciferase). The chimeric genes containing the reporter genes under the control of a selected promoter and a hypoxia response element are introduced into a tissue where it is desirable to localize the site of hypoxia. Hypoxia is localized by increased expression of the reporter gene.

The following examples illustrate but in no way are intended to limit the present invention.

MATERIALS AND METHODS

Unless indicated otherwise, chemicals and reagents were obtained from Sigma Chemical Company (St. Louis, Mo.) or Mallinckrodt Specialty Chemicals (Chesterfield, Mo.), restriction endonucleases were obtained from New England Biolabs (Beverly, Mass.), and other modifying enzymes and biochemicals were obtained from Pharmacia Biotech (Piscataway, N.J.), Boehringer Mannheim (Indianapolis, Ind.) or Promega Corporation (Madison, Wis.). Materials for media for cell culture were obtained from Gibco/BRL (Gaithersburg, Md.) or DIFCO (Detroit, Mich.). Unless otherwise indicated, manipulations of cells, bacteria and nucleic acids were performed using standard methods and protocols (e.g., Titus; Sambrook, et al.; Ausubel, et al.).

A. Definitions

"Transformation" means introducing DNA into an organism so that the DNA is replicable, either as an extrachromosomal element or by chromosomal integration. Several transformation methods are commonly used in the art, and may be found, for example, in Ausubel, et al., and Sambrook, et al.

"Transfection" refers to the taking up of an expression vector by a host cell whether or not any coding sequences are in fact expressed. Numerous methods of transfection are known to the ordinarily skilled artisan, for example, $CaPO_4$ and electroporation. Successful transfection is generally recognized when any indication of the operation of the expression vector occurs within the host cell.

"Plasmids" are designated by a lower case p preceded and/or followed by capital letters and/or numbers. The starting plasmids herein are either commercially available, publicly available on an unrestricted basis, or can be constructed from available plasmids in accord with published procedures.

"Digestion" of DNA refers to catalytic cleavage of the DNA with a restriction enzyme that acts only at certain sequences (restriction sites) in the DNA. The various restriction enzymes used herein are commercially available (e.g., New England Biolabs, Beverly, Mass.) and their reaction conditions are known to the ordinarily skilled artisan. For analytical purposes, typically 1 µg of a plasmid or of a DNA fragment is used with about 2 units of enzyme in about 20 µl of buffer solution. For the purpose of isolating DNA fragments for plasmid construction, typically 5 to 10 µg of DNA are digested with about 20 to 40 units of enzyme in a larger volume. Appropriate buffers and substrate amounts for particular restriction enzymes are specified by the manufacturer. Incubation times of about one hour at 37° C. are ordinarily used, but may vary in accordance with the supplier's instructions. After digestion, the reaction products are run on a gel (e.g., agarose) to isolate desired fragments.

"Ligation" refers to the process of forming phosphodiester bonds between two double stranded nucleic acid fragments (e.g., Sambrook, et al.). Unless otherwise noted, ligation may be accomplished using known buffers and conditions with 10 units of T4 DNA ligase per 0.5 µg of approximately equimolar amounts of the DNA fragments to be ligated.

"Filling" or "blunting" refer to the procedures by which the single stranded end in the cohesive terminus of a restriction enzyme-cleaved nucleic acid is converted to a double strand. This eliminates the cohesive terminus and forms a blunt end. This process is a versatile tool for converting a restriction cut end that may be cohesive with the ends created by only one or a few other restriction enzymes into a terminus compatible with any blunt-cutting restriction endonuclease or other filled cohesive terminus. Typically, blunting is accomplished by incubating 2–15 µg of the target DNA in a buffer containing 10 mM $MgCl_2$, 1 Mm dithiothreitol, 50 mM NaCl, 10 mM Tris (pH 7.5) at about 37° C. in the presence of 8 units of the Klenow fragment of DNA polymerase I (Boehringer Mannheim, Indianapolis, Ind.) and 250 µM of each of the four deoxynucleoside triphosphates (Boehringer Mannheim). The incubation is generally terminated after about 30 min. The reaction products may be purified using standard phenol and chloroform extraction methods followed by ethanol precipitation.

"Northern" blotting is a method by which the presence of a cellular MRNA is confirmed by hybridization to a known, labelled oligonucleotide, DNA or RNA fragment. For the purposes herein, unless otherwise provided, Northern analysis shall mean electrophoretic separation of RNA, typically MRNA, on agarose (e.g., 1%) in the presence of a denaturant (e.g., 7% formaldehyde), transfer to nitrocellulose or nylon membrane, hybridization to the labelled fragment, washing, and detection of the labeled fragment, as described by Sambrook, et al.

B. Cells and Media

HeLa cells, Hep G2 cells and C2C12 myoblasts were obtained from the American Type Culture Collection (ATCC; Rockville, Md.). Human arterial endothelial cells were obtained from Clonetics Corp. (San Diego, Calif.). Unless otherwise indicated, the cells were grown at 37° C. under 5 or 10% $CO_2$ in MEM or DMEM medium (Gibco/BRL) containing 10% fetal bovine serum (Gibco/BRL).

Cardiac myocytes were isolated and cultured as described previously (Bishopric, et al., Webster and Bisphopric, 1992). Briefly, hearts from about 30 (three litters) were minced and subjected to serial trypsin digestion to release single cells. After the final digestion, the cells were washed and preplated for 0.5 h in minimal essential medium (MEM; Gibco/BRL, Gaithersburg, Md.) with 5% fetal calf serum (FCS; Gibco/BRL). Nonattached cells were re-plated in 60-mm Falcon dishes (Becton Dickinson Labware, Lincoln Park, N.J.) at a density of about $2.5 \times 10^6$ cells per dish in MEM containing 5% fetal calf serum, 2.0 g/l glucose and 10 mM HEPES, and grown at 37° C. under 5 or 10% $CO_2$.

C. DNA

1. Therapeutic Genes

Bcl-2 cDNA was obtained in the expression vector pSFFV-Bcl-2 from Dr. Stanley Korsemeyer (Washington University, St. Louis, Mo.; Hockenbery, et al., 1990). Nitric oxide synthase (bNOS) cDNA was obtained from Dr. Solomon Snyder in the vector pNOS (Johns Hopkins University, Baltimore, Md.; Bredt, et al., 1991).

2. Promoters (i) Cardiac-specific p$\alpha$MHC$_{5.5}$CAT, containing 5.5 kilobases (Kb) 5' of the mouse $\alpha$-myosin heavy chain ($\alpha$MHC) promoter ligated to the chloramphenicol acetyl transferase (CAT) gene, was obtained from Dr. Jeffrey Robbins (University of Cincinnati, College of Medicine, Cincinnati, Ohio; Subramaniam, et al.).

p$\alpha$MHC$_{2.0}$CAT, containing 2.0 Kb of the rat $\alpha$MHC promoter ligated to the CAT gene, was obtained from Dr. Thomas Gustafson (University of Maryland, Baltimore, Md.; Gustafson, et al.).

p$\alpha$MHC$_{86}$CAT, containing 86 base pairs (bp) of the rat $\alpha$MHC promoter ligated to the CAT gene, was obtained from Dr. Bruce Markham (Medical College of Wisconsin, Milwaukee, Wis.). The construct was made by 5' truncation of p$\alpha$MHC2.0CAT and blunt end ligation to the CAT gene. The sequence of the 86 bp promoter fragment is provided herein as SEQ ID NO:24.

pHCA$_{118}$CAT, containing 118 bp of the region 5' of the human cardiac $\alpha$-actin promoter ligated to the CAT gene, was also obtained from Dr. Larry Kedes (Minty and Kedes).

(i) Skeletal muscle-specific pHSA-150CAT, containing 150 bp of the human skeletal muscle $\alpha$-actin promoter ligated to the CAT gene, was obtained from Dr. Larry Kedes (University of Southern California, Los Angeles, Calif.; Muscat and Kedes).

3. Hypoxia Response Elements

A construct containing four tandem copies of the erythropoietin gene 3' hypoxia inducible enhancer element cloned into the BamHI site of pGEM-4Z (Promega Corp., Madison, Wis.) was obtained from Dr. Greg Semenza (Johns Hopkins University School of Medicine, Baltimore, Md.; Semenza and Wang, 1992). The enhancer element fragment, termed herein as HREE1 (SEQ ID NO:6), was excised from the pGEM vector by cleavage with SmaI and HincII for blunt end subcloning into constructs of the present invention (below).

A construct containing 691 bp (−628 to +63) of the $\beta$-enolase (ENO3) gene was obtained from Dr. Charlotte Peterson (Veterans Administration Medical Center, University of Arkansas, Little Rock, Ark.). A sequence containing this region is presented herein as SEQ ID NO:29.

4. Chimeric Genes and Expression Vectors of the Present Invention

The vector pGL2PV (plasmid-gene-1 lght-promoter-vector; Promega Corp., Madison, Wis.), was used as the base vector for the construction of most of the plasmids described below. pGL2PV is a eukaryotic expression vector containing the SV40 early promoter upstream of the luciferase gene. The vector multiple cloning (MCS) site is just upstream of the SV40 promoter, and is designed for the insertion of DNA fragments containing enhancer sequences. pGL2BV (Promega Corp.) is similar to pGL2PV, but it does not contain an SV40 early promoter.

(i) HREE1/luc Constructs with Different Tissue-Specific Promoters

Figure 1B:
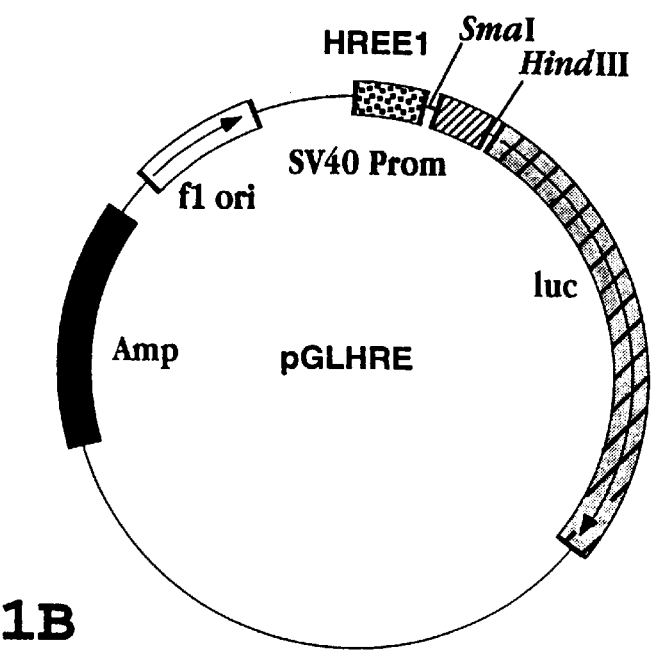
Figure 2A:
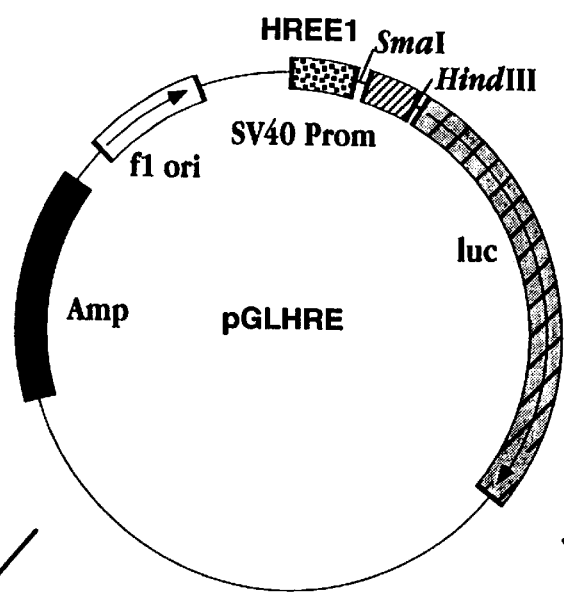
FIGS. 2A, 2B, 2C and 2D show a schematic diagram of the construction of plasmids pGLHSA-150HRE (FIG. 2B), pGLαMHC$_{86}$-HRE (FIG. 2C), and pGLHCA$_{118}$HRE (FIG. 2D), from plasmid pGLHRE (FIG. 2A).
Figure 3A:
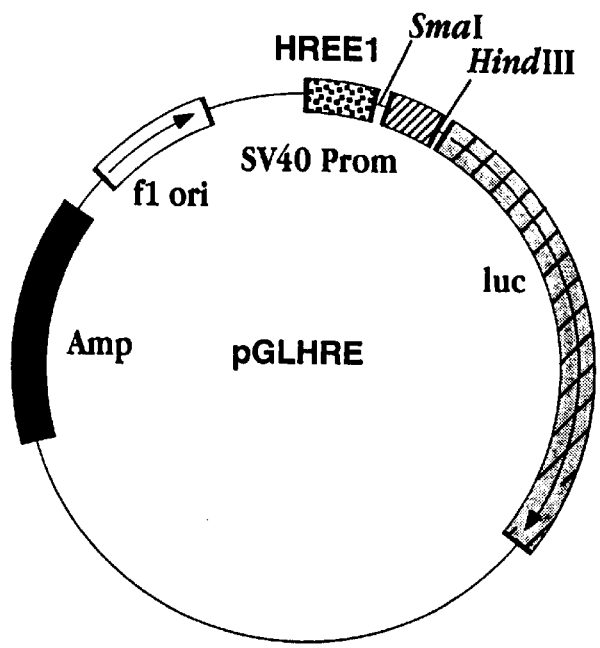
FIGS. 3A and 3B show a schematic diagram of the construction of plasmid pGLαMHC$_{1.2}$HRE (FIG. 3B) from plasmid pGLHRE (FIG. 3A).

Plasmid pGLHRE (FIGS. 1B, 2A, 3A) was made by blunt-1 lighting the 240 bp HREE1 fragment (SEQ ID NO:6) into the SmaI site of the MCS of pGL2PV (FIG. 1A).

Figures 2B, 2C, 2D:
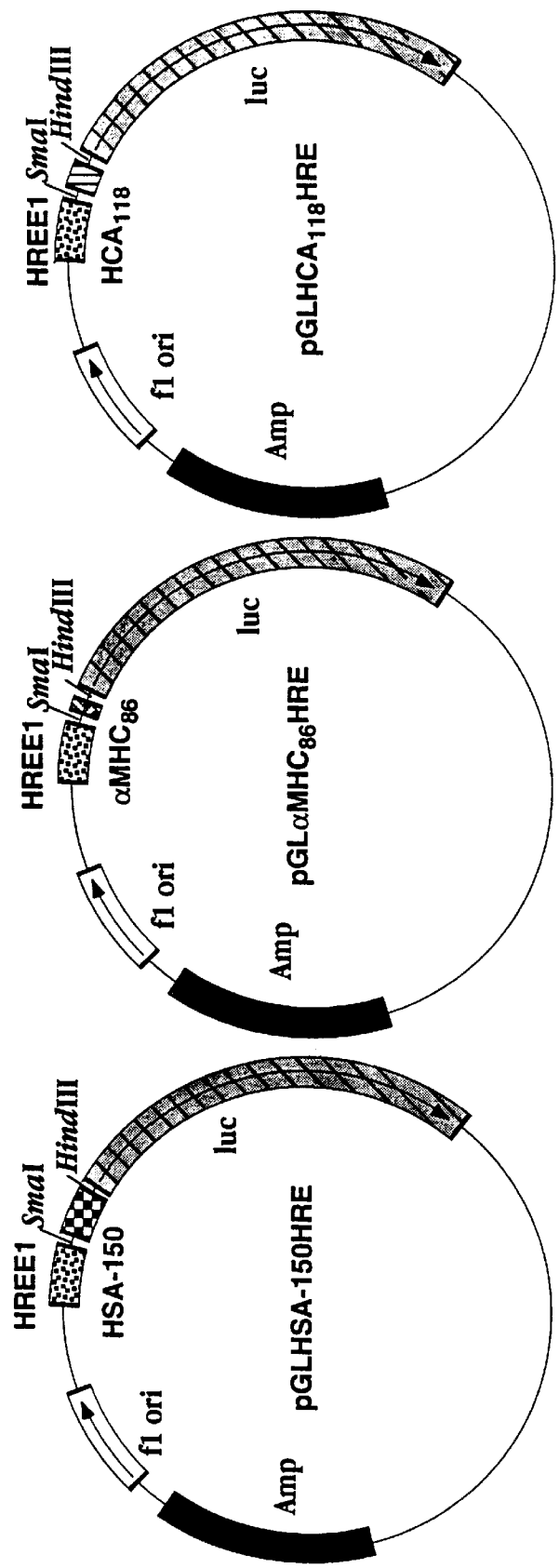

Plasmid pGLHSA-150HRE (FIG. 2B) was made by digesting pGLHRE with HindIII and SmaI to drop out the SV40 promoter and replacing it with a 150 bp HindIII-SmaI fragment from pHSA-150CAT containing a fragment of the human skeletal actin (HSA) promoter.

Plasmid pGL$\alpha$MHC$_{86}$HRE (FIG. 2C) was made by digesting pGLHRE with HindIII and SmaI to drop out the SV40 promoter and replacing it with a 120 bp HindIII-EcoRI fragment from p$\alpha$MHC$_{86}$CAT containing 86 bp (SEQ ID NO:24) of the human $\alpha$-myosin heavy chain ($\alpha$-MHC) promoter. The EcoRI end of the 120 bp fragment was filled in with DNA polymerase I using standard methods (Sambrook, et al.) before blunt end ligation to the vector SmaI site.

Plasmid DGL$\alpha$MHC$_{86}$-GATA-HRE was made by cloning a 36 bp oligonucleotide (SEQ ID NO:1; described above), containing a duplicated GATA 4 box into the HindIII site (filled in with polymerase) of plasmid pGL$\alpha$MHC$_{86}$HRE, upstream of the 86 bp promoter fragment.

Plasmid pGLHCA$_{118}$HRE (FIG. 2D) was made by digesting pGLHRE with HindIII and SmaI to drop out the SV40 promoter and replacing it with a 188 bp HindIII-EcoRI fragment from pHCA$_{118}$CAT, containing 118 bp of the human cardiac actin (HCA) promoter plus 70 bp of actin exon 1. The EcoRI end of the 188 bp fragment was filled in with DNA polymerase I as above before blunt end ligation to the vector SmaI site.

Figure 3B:
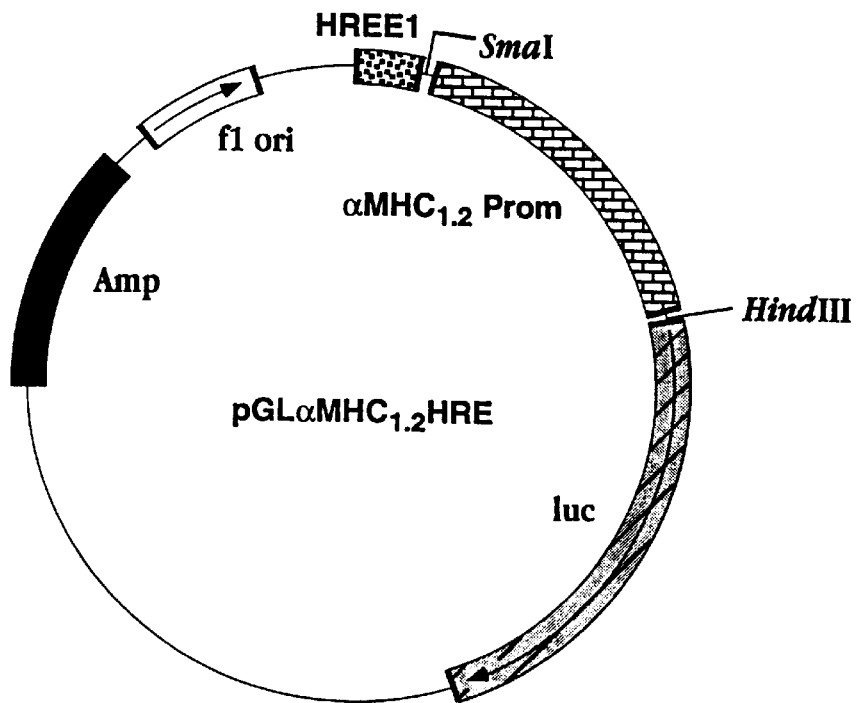

Plasmid pGL$\alpha$MHC$_{1.2}$HRE (FIG. 3B) was made by digesting pGLHRE with HindIII and SmaI to drop out the SV40 promoter and replacing it with a 1.2 kb HindIII-EcoRI fragment from p$\alpha$MHC$_{20}$CAT containing 1.2 kb of the human $\alpha$-MHC promoter. The EcoRI end of the 1.2 kb fragment was filled in as above in prior to cloning.

(ii) PKM Promoter/luc Constructs

Figure 6C:
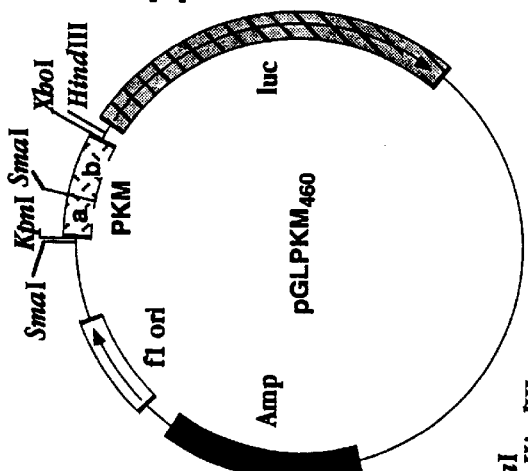

Plasmid pGLPKM$_{460}$, containing 460 bp of the rat muscle specific pyruvate kinase (PKM) gene promoter and 140 bp of the PKM coding sequence (SEQ ID NO:7), was created using polymerase chain reaction (PCR) as follows. PKM-specific primers containing endonuclease restriction sites near their 5' end were designed based on the nucleotide sequence of the PKM gene (Takenaka, et al., 1989). PKM primer F (SEQ ID NO:2) contained a KpnI site, while PKM primer R (SEQ ID NO:3) contained a XhoI site. PCR was carried out using the above primers and 1 μg of rat heart genomic DNA as a template for 25 cycles using standard procedures and a Perkin-Elmer (Norwalk, Conn.) DNA thermal cycler. The PCR product (FIG. 6A) was purified by agarose gel electrophoresis, cut with KpnI and XhoI, and cloned into KpnI/XhoI cut pGL2BV (FIG. 6B; Promega Corp., Madison, Wis.), generating pGLPKM$_{460}$ (FIG. 6C).

Figure 6E:
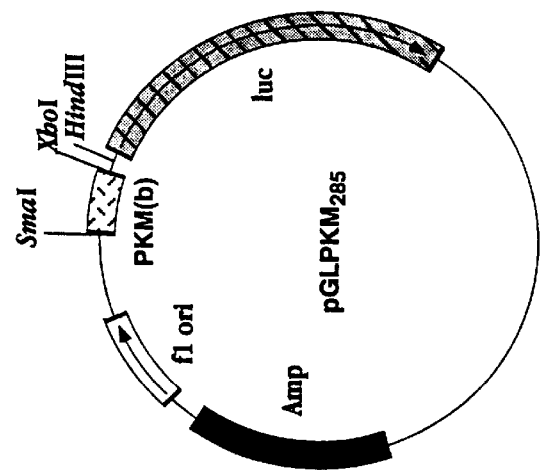
Figure 6D:
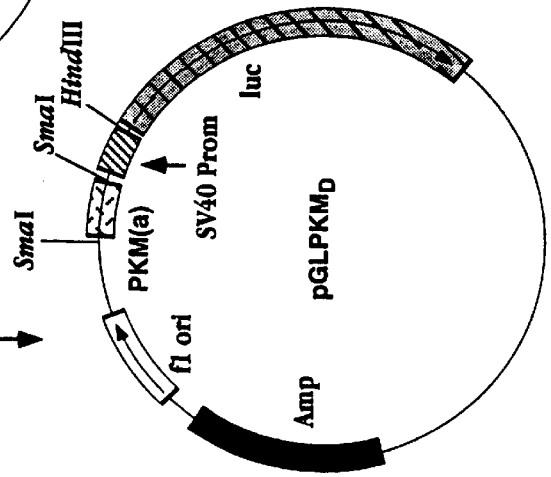

Plasmid pGLPKM$_{285}$ (FIG. 6E) was generated by digesting pGLPKM$_{460}$ with SmaI to drop out the −460 to −285 portion of the promoter, and religating the vector. pGLPKM$_D$ (FIG. 6D) was generated by digesting pGLPKM$_{460}$ with SmaI to isolate the −460 to −285 portion of the promoter, and cloning that fragment into pGL2PV (Promega Corp.) that had been cut with SmaI.

(iii) Et-1 Promoter/luc Constructs

Plasmid pGLET-1$_{700}$ (FIG. 7C), containing 700 bp of the human ET-1 gene promoter (SEQ ID NO:8), was created using PCR to amplify HeLa cell genomic DNA as described above. ET-1 specific primers were designed based on the promoter sequence (Inoue, et al., 1989) of the ET-1 gene. The forward primer (SEQ ID NO:4) contained PstI and KpnI sites, while the reverse primer (SEQ ID NO:5) contained HindIII and XbaI sites. The PCR product (FIG. 7A) was purified by gel electrophoresis, cut with KpnI and HindIII, and cloned into KpnI/HindIII cut pGL2BV (FIG. 7B; Promega Corp.).

(iv) ENO3 Promoter/luc Constructs

Plasmid pGLENO$_{628}$ was constructed by cloning a blunt ended genomic DNA containing an ENO3 promoter fragment (−628 to +63; SEQ ID NO:29), isolated from a lambda gt10 human genomic library, into the SmaI site of pGL2BV.

(v) Therapeutic Gene Constructs

Figure 4A:
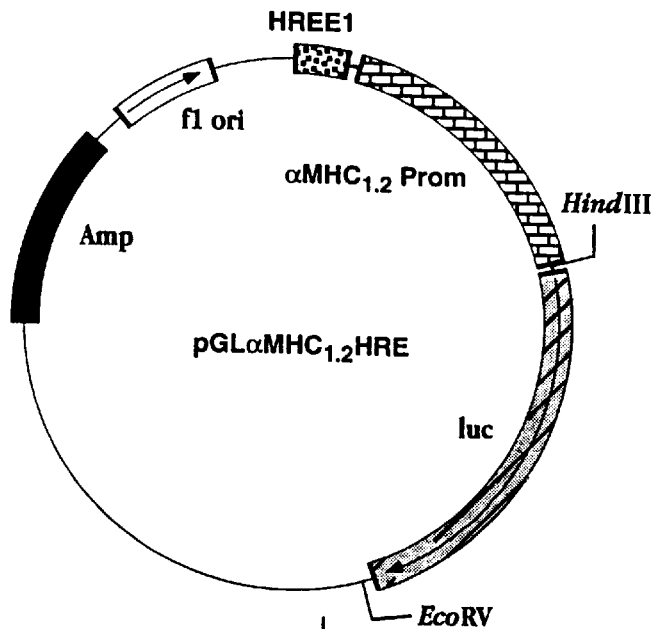
FIGS. 4A and 4B show a schematic diagram of the construction of plasmid pGLαMHC$_{1.2}$HRE-NOS (FIG. 4B) from plasmid pGLαMHC$_{1.2}$HRE (FIG. 4A).
Figure 4B:
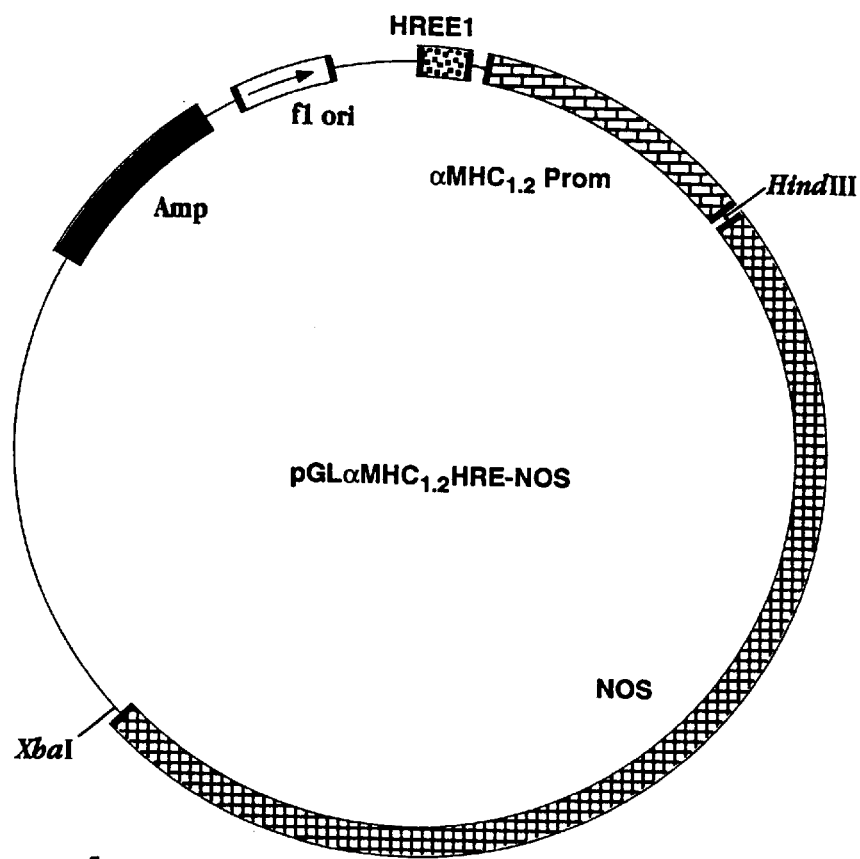

Plasmid pαMHC$_{1.2}$HRE-NOS (FIG. 4B) was made by digesting plasmid pGLαMHC$_{1.2}$HRE (FIG. 4A) with HindIII and EcoRV to drop out the luciferase cDNA and replacing it with a HindIII/XbaI fragment from pNOS containing a full length NOS CDNA.

Figure 5A:
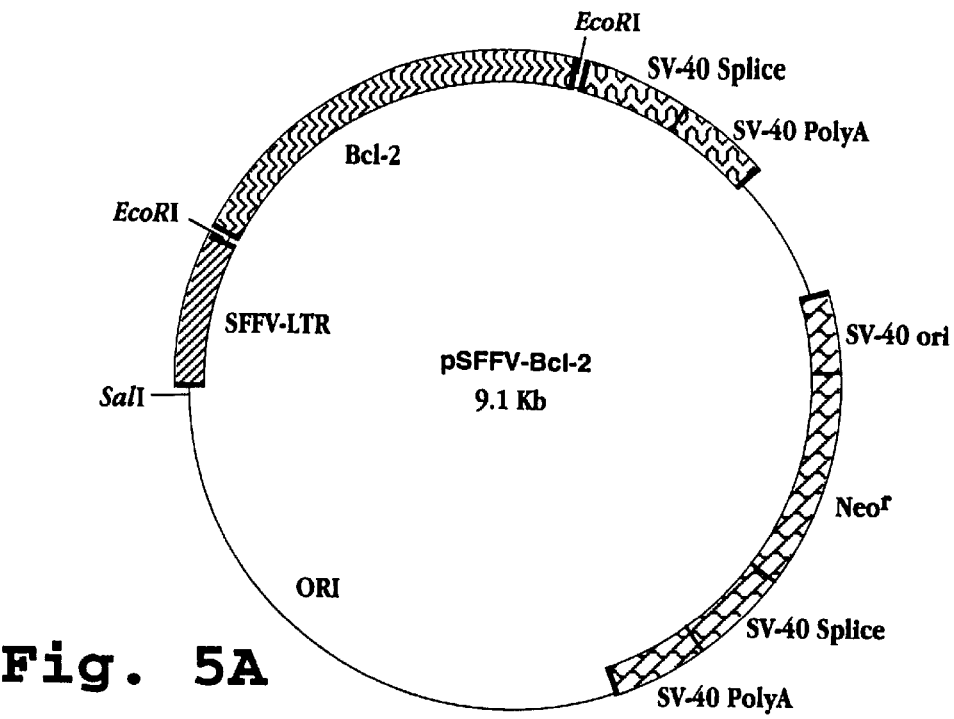
FIGS. 5A and 5B show a schematic diagram of the construction of plasmid pαMHC$_{1.2}$-HRE-Bcl-2 (FIG. 5B) from plasmid pSFFV-Bcl-2 (FIG. 5A).
Figure 5B:
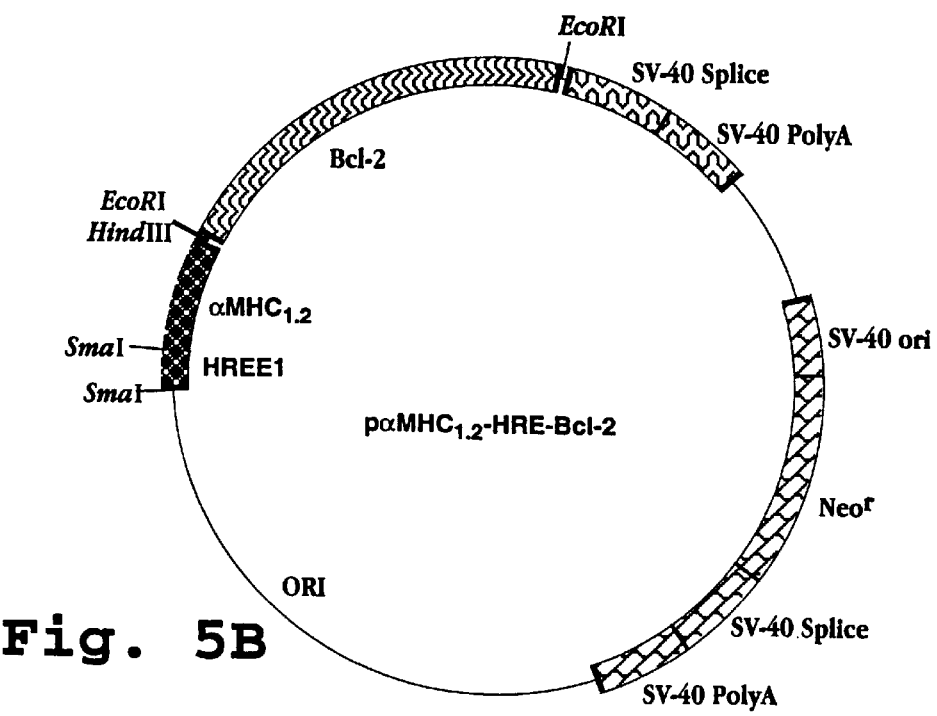

Plasmid pαMHC$_{1.2}$HRE-Bcl-2 (FIG. 5B) was made by digesting pSFFV-Bcl-2 with SalI, blunting the vector as described above, removing the SFFV promoter from the linearized vector with an EcoRI digest, and replacing the SFFV promoter with a SmaI/EcoRI fragment from pgLαMHC$_{1.2}$HREE containing the 1.2 kb αMHC promoter fragment and the 240 bp HREE1.

(vi) Other Plasmid Constructs

Plasmid pαMHC$_{5.5}$HRE-CAT was made by inserting the 240 bp HREE1 immediately 5' of the AMHC promoter of pαMHC$_{5.5}$CAT.

(vi) Adenoviral Constructs

Adenoviral constructs are made using standard methods (e.g., Friedman,, et al., 1986; Hertz and Gerard, 1993), as follows.

Construct AdαMHC1.2Bcl2HREE is made by inserting a 3.34 Kb EcoRI/HindIII fragment from pαMHC1.2-Bcl-2 (containing 1.2 Kb of the α-MHC promoter, 1.9 Kb Bcl-2 CDNA, and 240 bp HREE1) into pAPLCMV digested with EcoRI and HindIII to drop out the CMV promoter and CAT gene. pAPLCMV, which may be obtained from Dr. Larry Kedes (University of Southern California, Los Angeles, Calif.; Kass-Eisler, et al., 1993), is a base replication deficient adenoviral expression vector. The backbone adenoviral vector for recombination, p9M17, may also be obtained from Dr. Larry Kedes.

Recombinant pAPLCMV (pAdαMHC1.2bcl-2HRE) and p9M17 are used to co-transfect 293 cells (ATCC) to propagate the adenovirus.

EXAMPLE 1

Tissue Specific Hypoxia Induced Expression In Vitro

Constructs pGLHRE, pGLHSA-150HRE, pαMHC$_{5.5}$HRE-CAT, pGLαMHC$_{1.2}$HRE, pGLHCA$_{118}$HRE and pGL-Eno$_{628}$ were tested for tissue-specific expression and hypoxia inducibility in HeLa cells, Hep G2 cells, differentiated C2C12 muscle myotubes, and cardiac myocytes.

| A. | Buffers and Solutions |
|---|---|
| | HEPES buffered saline (HeBS; 2X solution) |
| 16.4 g | NaCl |
| 11.9 g | HEPES acid |
| 0.21 g | Na$_2$HPO$_4$ |
| H$_2$O to 1 liter | |
| Titrate Ph to 7.05 with 5 M NaOH. | |
| PBS Buffer | |
| 137 mM | NaCl |
| 2.7 mM | KCl |
| 4.3 mM | Na$_2$HPO$_4$ |
| 1.4 mM | KH$_2$PO$_4$ |
| Adjust pH to 7.1. | |
| Reconstituted Luciferase Assay Reagent (LAR) | |
| 20 mM | Tricine |
| 1.07 mM | (MgCO$_3$)$_4$MG(OH)$_2$.5H$_2$O |
| 2.67 mM | MgSO$_4$ |
| 0.1 mM | EDTA |
| 33.3 mM | DTT |
| 270 μM | coenzyme A |
| 470 μM | luciferin |
| 530 μM | ATP |
| Cell Culture Lysis Reagent (CCLR; 1X Solution) | |
| 25 mM | Tris-phosphate, pH 7.8 |
| 2 mM | DTT |
| 2 mM | 1,2-diaminocyclohexane-N,N,N',N'-tetraacetic acid |
| 10% | glycerol |
| 1% | Triton X-100 |

A. Cell Transfection

HeLa cells, C2C12 myocytes, and cardiac myocytes were transfected with the indicated plasmid DNA by the standard calcium phosphate procedure (Ausubel, et al.).

Briefly, 10$^5$ cells were plated on a 10-cm tissue culture dish and grown for 3 days. The cells were split 1:10 into 10 ml of medium one day before application of plasmid DNA. DNA for transfection was prepared by resuspending an ethanol-precipitated pellet containing 20 μg of the plasmid DNA in 450 μl ddH$_2$O and adding 50 μl of 2.5 mM CaCd$_2$.

500 μl of 2× HeBS were added to a 15 ml conical centrifuge tube, and the solution was aerated by bubbling air with a 10 ml pipette attached to an automatic pipettor (Drummond Instruments, Fisher Scientific, Pittsburgh, Pa.). The DNA/CaCl$_2$ solution was added dropwise, and the resultant mixture was vortexed for 5 seconds and then allowed to sit for 20 minutes at room temperature to form precipitate.

The precipitate was added to the dishes containing the cells and the dishes were incubated overnight.

The cells were washed twice with 5 ml PBS and fed with 10 ml of complete medium. The cells were then allowed to recover for 24 hours before incubation under an atmosphere of 1.0% $O_2$, 5% $CO_2$, 94% $N_2$ for an additional 20 hours.

B. Exposure to Hypoxic Conditions

Two to three days after transfection, the cells were exposed to atmospheric oxygen (approximately 21% $O_2$, 5% $CO_2$, balance $N_2$; $pO_2$=~160 mmHg), or to hypoxic conditions (approximately 0.5–2.0% $O_2$, 5% $CO_2$, balance $N_2$; $pO_2$=~4–8 mmHg) in an environmental chamber (Anaerobic Systems, San Jose, Calif., USA) which was equipped with a Nikon TMS microscope and a continuous readout oxygen electrode (Controls Katharobic, Philadelphia, Pa., USA). Unless otherwise indicated, the cells were kept in the chambers for one day prior to assaying for luciferase expression.

C. Luciferase Expression

Cells transfected and treated as above were assayed for expression of the luciferase enzyme using a standard reaction protocol (Titus). Briefly, 1 ml of CCLR and 1 ml of LAR were allowed to equilibrate at room temperature. The culture medium in the dish containing the cells to be assayed was removed and the cells were rinsed twice in PBS buffer.

Approximately 300 μl of the room-temperature CCLR was added to the dish containing the cells, and the dish was incubated at room temperature for 10–15 minutes. The cells were then scraped off the bottom of the culture dish, and the solution containing the cells was transferred to a microcentrifuge tube. The tube was centrifuged in a table-top microcentrifuge briefly (about 5 seconds) to pellet large debris.

20 μl of the supernatant (cell extract) were mixed with 100 μl of LAR at room temperature, and the light produced was measured for a period of 5 minutes, starting approximately 5 seconds after mixing, with a model # 1250 LKB luminometer (Bioorbit, Gaithersburg, Md.).

D. Results

Data from HeLa, C2C12, and cardiac cells are given in Table 1, below. Values, presented in arbitrary units, represent averages of three or more experiments for each condition.

basal (aerobic) expression from $\alpha$-$MHC_{1.2}$ $HCA_{118}$, and $HSA_{150}$ promoters is weak.

These results indicate that the HREE1 element is fully functional when fused to muscle and cardiac specific promoters and that muscle and cardiac cells are fully responsive to hypoxia in terms of the regulation of these promoters, and suggest that the $\alpha MHC_{1.2}$ promoter is an exemplary promoter for moderate levels of cardiac-specific expression.

The data also show that both the HREE present in the ENO3 promoter and HREE1, when present in constructs with the SV40 promoter, result in comparable levels of hypoxia induction in skeletal muscle cells. In cardiac cells, however, constructs containing the ENO3 HREE are expressed at significantly higher levels than those containing HREE1. Further, hypoxia increases the level of expression of the ENO3 HREE containing constructs in cardiac cells by over seven-fold, as compared with less than 5-fold in skeletal muscle cells. Plasmid $pGLENO_{628}$ confers induced expression in C2C12 myotubes and cardiac myocytes that is at least equivalent to four copies of the erythropoietin HRE (HREE1) in these cells. These results suggest that the HREE in the ENO3 promoter fragment may be a particularly effective HREE for hypoxia induction in constructs targeted with a tissue-specific promoter to cardiac or skeletal muscle cells.

EXAMPLE 2

Tissue Specific Hypoxia Induced Expression In Vivo Following Injection of Constructs into Target Animal Tissue Constructs of the present invention were injected directly into cardiac tissue using techniques described in Buttrick, et al., (1992) and Buttrick, et al., (1993). Briefly, adult female Wistar rats were anesthetized with an intraperitoneal injection of chloral hydrate (0.7 ml/100 g of a 4% solution). Cardiac injections were made directly into the apex of the heart through a lateral thoractomy, after which the heart was

TABLE 1

REGULATED EXPRESSION OF UBIQUITOUS-MUSCLE- AND CARDIAC-SPECIFIC PROMOTERS BY HYPOXIA

| | GL2PV | | GLHRE | | $GLHSA_{150}HRE$ | | $\alpha MHC_{1.2}HRE$ | | $GLHCA_{118}HRE$ | | $GLENO_{628}$ | |
|---|---|---|---|---|---|---|---|---|---|---|---|---|
| | A | Hx | A | Hx | A | Hx | A | Hx | A | Hx | A | Hx |
| HeLa | 18 | 27 | 56 | 387 | BG | | BG | | BG | | — | |
| C2C12 | 189 | 204 | 350 | 1680 | 46 | 278 | BG | | 48 | 248 | 320 | 1560 |
| Cardiac | 24 | 27 | 22 | 165 | 18 | 94 | 21 | 85 | 38 | 263 | 210 | 1610 |

BG - Background

Data shown in the table demonstrate that (i) none of the tested constructs carrying tissue-specific promoters are expressed above background in fibroblast-derived HeLa cells under either normal or hypoxic conditions, (ii) cells containing constructs having HREE1 and a compatible promoter (including the SV40 and tissue-specific promoters) express the reporter at levels that are ~5 to ~7 times greater under hypoxic conditions than under aerobic conditions; (iii) the HREE1 element is equally active in different cells and independent of the promoter; (iv) the $\alpha$-$MHC_{1.2}$ promoter expresses in cardiac, but not in skeletal or fibroblast-derived cells, the $HCA_{118}$ promoter expresses in both cardiac and skeletal muscle cells, but not in fibroblast-derived cells, and the $HSA_{150}$ promoter expresses in both skeletal and cardiac muscle, with stronger expression in skeletal muscle; and (v)

replaced in the chest, the rats were briefly hyperventilated, and the incision closed. Fifty microliters of a DNA solution containing 2 μg/μl of either pGLHRE or $pGLHCA_{118}HRE$ in 20% sucrose and 2% Evans blue were injected through a 27-gauge needle. Following injection the rats were subjected to a 20 min ischemia by cannulation of the coronary artery as described by Smith, et al. (1988).

Hypoxia-inducibility of vector expression was assayed as follows. Hearts were excised approximately 20 hours after the induced ischemia and the ventricles were washed with ice-cold phosphate buffered saline (PBS). The tissue was suspended in 1 ml of ice-cold PBS containing 20% sucrose and homogenized with a Polytron (Kinematica, Switzerland) for 45 sec. After centrifugation at 10,000×g for 10 min supernatants were analyzed for luciferase expression by the assay method described above. Protein was measured using a BioRad assay kit (BioRad Laboratories, Hercules, Calif.).

The results of the experiments are shown in Table 2, below. Luciferase expression in hearts from rats injected with pGLHRE or pGLHCA118HRE and subjected to ischemia was approximately 2-fold higher than expression in hearts from control animals injected with saline (n=3).

TABLE 2

ISCHEMIA INDUCIBLE EXPRESSION OF pGLHRE AND pGLHCA$_{118}$HRE IN RAT HEART

| Plasmid | Luciferase Activity Light Units/mg Protein | |
|---|---|---|
| | Aerobic | 20 min. Ischemic |
| pGLHRE | 1180 | 2440 |
| pGLHCA$_{118}$HRE | 88 | 127 |
| Control | 15 | 21 |

Rat hearts were injected with plasmids as described above. A 20 min. ischemia was imposed on one group (3 rats) and the other (1 control) was sham operated. Tissue samples were harvested and assayed for luciferase expression 20 hr. later.

These results indicate that the direct injection of plasmid DNA, made in accordance with the teachings of the present specification, into hearts of living mammals is effective to result in the expression of genes carried on those plasmids. Further, these results indicate that expression vectors carrying chimeric genes of the present invention are effective to result in significantly increased levels of expression in response to hypoxia caused by ischemia in vivo.

EXAMPLE 3

Stable Expression of Hypoxia Regulated NOS and Bcl-2 Genes In Vitro $10^6$ C2C12 myoblasts were cotransfected with pSV2Neo (Minty and Kedes) and a test plasmid at a ratio of 1:19 (1 µg pSV2Neo+19 µg test plasmid) using standard methods (Minty and Kedes, 1986). Test plasmids were pGLHRE, pGLHCA$_{118}$HRE, pGLαMHC$_{1.2}$HRE, pSFFV-Bcl-2, and pNOS-HRE. Cultures were selected on day 2 following transfection with 400 µg/ml of the neomycin drug G418 (Gibco/BRL). Colonies of cells resistant to G418 appeared after 10 to 14 days. The resistant cells were pooled. Mass cultures were assayed for the expression of luciferase as described above or by Northern blot assay (Webster, et al., 1993) for the expression of Bcl-2 or NOS RNA. Stable lines were positive for expression of the transfected genes.

Mass cultures were subjected to differentiation conditions by transferring them to low mitogen medium (DMEM with 2% horse serum) and were analyzed visually for differentiation into myotubes. There was no apparent difference between transfected and control cells. Approximately 40% of cells were fused into multinucleate myotubes after 24 h in low mitogen medium. All cultures contained approximately 74% myotubes after 48 h.

Reporter-transfected cells differentiated normally and respond to hypoxia with the predicted induction of reporter. NOS-transfected cells appeared normal both during the hypoxia and during subsequent reoxygenation. A stable line of C2C12 cells that constitutively over-expresses Bcl-2 (without HREE1) was also constructed as described above, and the cells showed normal growth and differentiation characteristics.

Taken together, the data presented above suggest that inclusion of HRE elements, Bcl-2 over-expression, and hypoxia-induced over-expression of NOS is not toxic to muscle cells in vitro. Further, the data indicate that the cells may be protected from the deleterious effects of hypoxia by the expression of therapeutic genes (e.g., NOS).

EXAMPLE 4

Expression of DGLPKM Plasmids under Hypoxic Conditions

Plasmid pGLPKM$_{460}$ was transfected into C2C12 cells and cardiac myocytes and assayed for luciferase activity as described in Example 1. The expression of PGLPKM in both transfected C2C12 myotubes and neonatal cardiac myocytes was increased by 6±2 fold (n=4) in both cell types by incubation of the cells in an atmosphere containing 0.5% $O_2$, 5% $CO_2$, balance $N_2$ (hypoxic conditions) relative to normal conditions, as described in Example 1.

A portion of this HRE element, obtained by digesting with SmaI to cut at an internal SmaI site, is also effective as a hypoxia response enhancer element. This fragment, termed HREPKM$_{285}$, confers hypoxia-induced expression in C2C12 myotubes and cardiac myocytes similar to that obtained with pGLPKM$_{460}$. This level of hypoxia induction is at least equivalent to that obtained using HREE1 (SEQ ID NO:6).

These results indicate that the PKM promoter fragment contained in the sequence represented as SEQ ID NO:7 contains an HRE element that is effective at enhancing the expression of chimeric genes containing the element under conditions of hypoxia.

The PKM promoter sequence has no significant homology with the erythropoietin HRE consensus, but does share a consensus sequence (SEQ ID NO:31) with the ENO3 promoter fragment (SEQ ID NO:29). This consensus, located approximately 88 bp upstream of the transcription start site of PKM and approximately 70 bp upstream of the transcription start site of ENO3, may represent an important element for conferring enhancement of expression in response to hypoxia.

EXAMPLE 5

Expression of pGLET-1$_{700}$ Plasmids under Hypoxic Conditions

Plasmid pGLET-1$_{700}$ was transfected into human arterial endothelial cells as described in Example 1. The expression of pGLET-1$_{700}$ in these cells was increased 5 fold by incubation of the cells in a hypoxic atmosphere as described above. No significant induction of pGLET-1$_{700}$ was observed in any other cell types tested, including HeLa, C2C12, and cardiac myocytes. Elements contained within the 700 bp sequence have no significant homology with the erythropoietin HRE consensus.

These results indicate that the 700 bp fragment of the human ET-1 gene promoter corresponding to the sequence represented herein as SEQ ID NO:8 is effective to (i) restrict expression of genes under its control to the vascular endothelium, and (ii) confer hypoxia-inducibility on the expression of those genes. Accordingly, this fragment, in conjunction with a therapeutic or reporter gene, may be used in the methods of the present invention to both target expression to a selected tissue (vascular endothelium), and confer enhancement of expression by hypoxia.

While the invention has been described with reference to specific methods and embodiments, it is appreciated that various modifications and changes may be made without departing from the invention.

It is claimed:

1. A chimeric DNA construct, comprising a hypoxia response enhancer element, a tissue-specific promoter heterologous to the element, and a coding sequence, with the proviso that the coding sequence is not an alpha globin coding sequence, wherein said promoter is operably linked to said coding sequence and said element is effective to cause expression of said coding sequence under conditions of hypoxia.

2. A chimeric DNA construct of claim 1, wherein said promoter is a cardiac-specific promoter.

3. A chimeric DNA construct of claim 1, wherein said promoter is selected from the group consisting of α-MHC$_{5.5}$ promoter, α-MHC$_{87}$ promoter, and human cardiac actin promoter.

4. A chimeric DNA construct of claim 1, wherein said promoter is a kidney-specific promoter.

5. A chimeric DNA construct of claim 4, wherein said promoter is a renin promoter.

6. A chimeric DNA construct of claim 1, wherein said promoter is a brain-specific promoter.

7. A chimeric DNA construct of claim 6, wherein said promoter is selected from the group consisting of aldolase C promoter, and tyrosine hydroxylase promoter.

8. A chimeric DNA construct of claim 1, wherein said promoter is a vascular endothelium-specific promoter.

9. A chimeric DNA construct of claim 8, wherein said promoter is selected from the group consisting of Et-1 promoter and vonWillebrand factor promoter.

10. A chimeric DNA construct of claim 1, wherein said hypoxia response enhancer element is selected from the group consisting of erythropoietin HRE element (HREE1), pyruvate kinase (PKM) HRE element, enolase 3 (ENO3) HRE element and endothelin-1 (ET-1) HRE element.

11. A chimeric DNA construct of claim 1, wherein said coding sequence is selected from the group consisting of nitric oxide synthase (NOS), Bcl-2, superoxide dismutase (SOD), and catalase.

12. An expression vector, comprising a hypoxia response enhancer element, a tissue-specific promoter heterologous to the element, and a coding sequence, with the proviso that the coding sequence is not an alpha globin coding sequence wherein said promoter is operably linked to said coding sequence and said element is effective to cause expression of said coding sequence.

13. An expression vector of claim 12, wherein said expression vector is a plasmid.

14. An expression vector of claim 12, wherein said expression vector is an adenovirus vector.

15. An expression vector of claim 12, wherein said expression vector is a retrovirus vector.

16. The chimeric DNA construct of claim 1, wherein said coding sequence is a viral thymidine kinase coding sequence.

17. The chimeric DNA construct of claim 16, wherein said viral thymidine kinase coding sequence encodes herpes simplex viral thymidine kinase.

18. The chimeric DNA construct of claim 1, wherein said coding sequence encodes luciferase.

* * * * *

SEQUENCE LISTING ( 1 ) GENERAL INFORMATION:

( i i i ) NUMBER OF SEQUENCES: 31

( 2 ) INFORMATION FOR SEQ ID NO:1:

( i ) SEQUENCE CHARACTERISTICS:
    ( A ) LENGTH: 35 base pairs
    ( B ) TYPE: nucleic acid
    ( C ) STRANDEDNESS: single
    ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
    ( C ) INDIVIDUAL ISOLATE: GATA4 Enhancer ( x i ) SEQUENCE DESCRIPTION: SEQ ID NO:1:

CAAAGGGCCG ATGGGCAGAT AGAGGAGAGA CAGGA     35

( 2 ) INFORMATION FOR SEQ ID NO:2:

( i ) SEQUENCE CHARACTERISTICS:
    ( A ) LENGTH: 33 base pairs
    ( B ) TYPE: nucleic acid
    ( C ) STRANDEDNESS: single
    ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
    ( C ) INDIVIDUAL ISOLATE: PKM primer F ( x i ) SEQUENCE DESCRIPTION: SEQ ID NO:2:

AATTGGTACC CGGGCGAGCG CCGGGAGGGT GGA     33

( 2 ) INFORMATION FOR SEQ ID NO:3:

( i ) SEQUENCE CHARACTERISTICS:
    ( A ) LENGTH: 32 base pairs
    ( B ) TYPE: nucleic acid
    ( C ) STRANDEDNESS: single
    ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
    ( C ) INDIVIDUAL ISOLATE: PKM primer R ( x i ) SEQUENCE DESCRIPTION: SEQ ID NO:3:

TTAACTCGAG GCACTATGGC ATTGGCTCTG GG     32

( 2 ) INFORMATION FOR SEQ ID NO:4:

( i ) SEQUENCE CHARACTERISTICS:
    ( A ) LENGTH: 41 base pairs
    ( B ) TYPE: nucleic acid
    ( C ) STRANDEDNESS: single (D) TOPOLOGY: linear (ii) MOLECULE TYPE: DNA (iii) HYPOTHETICAL: NO (iv) ANTI-SENSE: NO (vi) ORIGINAL SOURCE:
 (C) INDIVIDUAL ISOLATE: ET-1 primer F (xi) SEQUENCE DESCRIPTION: SEQ ID NO:4:

TATATCTGCA GGTACCGATA GGGAAAAGAC TGGCATGTGC C 41

(2) INFORMATION FOR SEQ ID NO:5:

(i) SEQUENCE CHARACTERISTICS:
 (A) LENGTH: 43 base pairs
 (B) TYPE: nucleic acid
 (C) STRANDEDNESS: single
 (D) TOPOLOGY: linear (ii) MOLECULE TYPE: DNA (iii) HYPOTHETICAL: NO (iv) ANTI-SENSE: NO (vi) ORIGINAL SOURCE:
 (C) INDIVIDUAL ISOLATE: ET-1 primer R (xi) SEQUENCE DESCRIPTION: SEQ ID NO:5:

TATATAAGCT TCTAGAGACC CGTTCGCCTG GCGCGCAGAT GCA 43

(2) INFORMATION FOR SEQ ID NO:6:

(i) SEQUENCE CHARACTERISTICS:
 (A) LENGTH: 240 base pairs
 (B) TYPE: nucleic acid
 (C) STRANDEDNESS: double
 (D) TOPOLOGY: linear (ii) MOLECULE TYPE: DNA (genomic)

(iii) HYPOTHETICAL: NO (iv) ANTI-SENSE: NO (vi) ORIGINAL SOURCE:
 (C) INDIVIDUAL ISOLATE: HREE1 (Hypoxia responsive enhancer
  element 1)

(xi) SEQUENCE DESCRIPTION: SEQ ID NO:6:

CGGGCCCTAC GTGCTGTCTC ACACAGCCTG TCTGACCTCT CGACCTACCG GCCCGGGATC 60

CCGGCCCTAC GTGCTGTCTC ACACAGCCTG TCTGACCTCT CGACCTACCG GCCCGGGATC 120

CCGGCCCTAC GTGCTGTCTC ACACAGCCTG TCTGACCTCT CGACCTACCG GCCCGGGATC 180

CCGGCCCTAC GTGCTGTCTC ACACAGCCTG TCTGACCTCT CGACCTACCG GCCGATCCCG 240

(2) INFORMATION FOR SEQ ID NO:7:

(i) SEQUENCE CHARACTERISTICS:
 (A) LENGTH: 560 base pairs
 (B) TYPE: nucleic acid
 (C) STRANDEDNESS: double
 (D) TOPOLOGY: linear (ii) MOLECULE TYPE: DNA (genomic)

(iii) HYPOTHETICAL: NO (iv) ANTI-SENSE: NO ( v i ) ORIGINAL SOURCE:
  ( C ) INDIVIDUAL ISOLATE: sequence containing PKM promoter frag.

( x i ) SEQUENCE DESCRIPTION: SEQ ID NO:7:

```
GAGTCACCGG  GCGGGGCTGG  AGGAATGTCC  GGGACCTATA  AATCTGGGCA  ACGCCCTGGT      60
AGGCCAGGGC  AGATGGGGCA  CCTGGGCAGA  ATTCCAAAAT  GGGATTATGT  AGCCTCTGAG     120
GTCCTAAAGC  AACAGGTGGC  GGACCACCCG  GGATCTAGG   GGTGGTGGCG  GCGGTGGACC     180
CGAGGGCGGG  TCCTGCCTCC  TCACCACTTC  CCCATTGGCC  ATCAGAATGA  CCCATGCGCA     240
ATTTTGGTTT  GCAATGTCCT  TCCGCCACGG  AAGGTAGTCC  CCCTCAAAAG  GGCAACCTGC     300
TTGTCCCGCC  TACCCTGCGA  CTCTCTCAGA  AGGTGCGGGT  GCCTGTTGAG  AGGCGGGGCT     360
CTGCTAGCTC  CTGCCCGGAT  TGGGCGAGGG  GCGGGGCTGC  GGAGGGATTG  CGGCGGCCCG     420
CAGCAGTGAT  AACCTTGAGG  CCCAGTCTGC  GCAGCCCCGC  ACAGCAGCGA  CCCGTCCTAA     480
GTCGACAGAC  GTCCTCTTTA  GGTATTGCAA  CAGGATCTGA  AGTACGCCCG  AGGTGAGCGG     540
GGAGAACCTT  TGCCATTCTC                                                     560
```

( 2 ) INFORMATION FOR SEQ ID NO:8:

( i ) SEQUENCE CHARACTERISTICS:
    ( A ) LENGTH: 713 base pairs
    ( B ) TYPE: nucleic acid
    ( C ) STRANDEDNESS: double
    ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
    ( C ) INDIVIDUAL ISOLATE: Sequence containing ET-1 promoter ( x i ) SEQUENCE DESCRIPTION: SEQ ID NO:8:

```
GATAGGGAAA  AGACTGGCAT  GTGCCTAAAC  GAGCTCTGAT  GTTATTTTA   AGCTCCCTTT      60
CTTGCCAATC  CCTCACGGAT  CTTTCTCCGA  TAGATGCAAA  GAACTTCAGC  AAAAAAGACC     120
CGCAGGAAGG  GGCTTGAAGA  GAAAAGTACG  TTGATCTGCC  AAAATAGTCT  GACCCCCAGT     180
AGTGGGCAGT  GACGAGGGAG  AGCATTCCCT  TGTTTGACTG  AGACTAGAAT  CGGAGAGACA     240
TAAAGGAAA   ATGAAGCGAG  CAACAATTAA  AAAAAATTCC  CCGCACACAA  CAATACAATC     300
TATTTAAACT  GTGGCTCATA  CTTTTCATAC  CAATGGTATG  ACTTTTTTC   TGGAGTCCCC     360
TCTTCTGATT  CTTGAACTCC  GGGGCTGGCA  GCTTGCAAAG  GGGAAGCGGA  CTCCAGCACT     420
GCACGGGCAG  GTTTAGCAAA  GGTCTCTAAT  GGGTATTTTC  TTTTTCTTAG  CCCTGCCCCC     480
GAATTGTCAG  ACGGCGGGCG  TCTGCTTCTG  AAGTTAGCAG  TGATTTCCTT  TCGGGCCTGG     540
CTTATCTCCG  GCTGCACGTT  GCCTGTTGGT  GACTAATAAC  ACAATAACAT  TGTCTGGGGC     600
TGGAATAAAG  TCGGAGCTGT  TTACCCCCAC  TCTAATAGGG  GTTCAATATA  AAAGCCGGC      660
AGAGAGCTGT  CCAAGTCAGA  CGCGCCTCTG  CATCTGCGCC  AGGCGAACGG  GTC            713
```

( 2 ) INFORMATION FOR SEQ ID NO:9:

( i ) SEQUENCE CHARACTERISTICS:
    ( A ) LENGTH: 118 base pairs
    ( B ) TYPE: nucleic acid
    ( C ) STRANDEDNESS: double
    ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
    ( C ) INDIVIDUAL ISOLATE: HCA118 promoter fragment ( x i ) SEQUENCE DESCRIPTION: SEQ ID NO:9:

```
CGAAGGGGAC  CAAATAAGGC  AAGGTGGCAG  ACCGGGCCCC  CCACCCCTGC  CCCCGGCTGC      60
TCCAACTGAC  CCTGTCCATC  AGCGTTCTAT  AAAGCGGCCC  TCCTGGAGCC  AGCCACCC       118
```

( 2 ) INFORMATION FOR SEQ ID NO:10:

( i ) SEQUENCE CHARACTERISTICS:
        ( A ) LENGTH: 1588 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( C ) INDIVIDUAL ISOLATE: Rat alpha MHC promoter fragment ( x i ) SEQUENCE DESCRIPTION: SEQ ID NO:10:

```
GAATTCTCTT  ACTATCAAAG  GGAAACTGAG  TCATGCACCT  GCAAAATGAA  TGCCCTCCCT      60
GGACATCATG  ACTTTGTCCC  TGGGGAGCCA  GCACTGTGGA  ACTCCAGGTC  TGAGAGTAGG     120
AGGCACCCCT  CAGCCTGAAG  CTGTGCAGAT  AGCTAGGGTG  TAAAAGAGGG  AAGGGGGGAG     180
GCTGGAATGG  GAGCTTGTGT  GTTCGGAGAC  AGGGGACAAA  TATTAGGCCC  GTAAGAGAAG     240
GTGACCCTTA  CCCAGTGTGT  TCAACTCAGC  CTTTCAGATT  AAAAATAACT  AAGGTAAGGG     300
CCATGTGGGT  AGGGGAGGTG  GTGTGAGACG  GTCCTGTCTC  TCCTCTATCT  GCCCATCGGC     360
CCTTTGGGGA  GGAGGAAATG  TGCCCAAGGA  CTAAAAAAGG  CCTGGAGCCA  GAGGGGCTAG     420
GGCTAAGCAG  ACCTTTCATG  GGCAAACCTC  AGGGCTGCTG  TCCTCCTGTC  ACCTCCAGAG     480
CCAAGGGATC  AAAGGAGGAG  GAGCCAGACA  GGAGGGATGG  GAGGGAGGGT  CCCAGCAGAT     540
GACTCCAAAT  TTAGGCAGCA  GGCACGCGGA  ATGAGCTATA  AAGGGGCTGG  AGCGCTGAGA     600
GCTGTCAGAC  CGAGATTTCT  CCATCCCAAG  TAAGAAGGAG  TTTAGCGTGG  GGGCTCTCCA     660
ACCGCACCAG  ACCTGTCCCA  CCTAGAGGGA  AAGTGTCTTC  CCTGGAAGTG  GGCTCCTCCC     720
ACCGGCCTGG  GAAGATTCCT  CGGTGGGCAG  GATGTTCTAC  TGGATGCCCC  TTCCCTTCCA     780
CTGCCTCCTC  CCTCCCTTGT  CTTGATTAAT  CTTGGCTCTT  AGTGTTCAGA  AAGATTTGCC     840
CGGTGCTGTC  TACTCCATCT  GTCTCTACTC  TCTCTGCCTT  GCCTTCTTGT  GTGTTCTCCT     900
TTTCCACGTG  TTTCTCACTC  CACTGCCTCC  CCCCCCCCCT  TCATTTTTAT  CCTTCCTTTC     960
TTTCTGTGTC  AGAATGCTGG  GAATCAAACC  CAGGGCTTCA  TACACGTCAA  GTAAGCAATC    1020
TCCCAGTGAG  TCAAAGCTTT  AATCCTCTGG  GTGCTGTCTT  ACCGAGCCTC  ACTCCCTGTC    1080
TTGTCCTGTT  CCGTCCTAGT  CAGGATCTCT  GGTCCGTCTC  TCAGCTTCTG  CTACTCCTCT    1140
CCCTGCCTGC  TCTTCTCTCC  GTCCAGCTGC  ACCTCTGTGG  CGCTCATTCC  AGCCGTGGTC    1200
CAAATTCTCT  GTGAAAAGAT  TAACCGGGTG  AGAATGCCCC  CAGTTTCCCC  TGTAGACAGC    1260
AGATCATGAT  TTTCCCCAGA  AGCCAGACTT  CCAGCGCCCG  CCCTCTGCCC  AGCAACTTGA    1320
CACTCTTAGC  AAACTTCAGC  CACCCTTCCC  CCACATAGAC  CAAGTCTTGC  AGAGAGCCTT    1380
```

-continued

| | | | | | |
|---|---|---|---|---|---|
| CCTTCAGATG | ACTTCGAGTT | CTTGCAAAGG | AAGGAGAACT | CTTTGTGGCG | GGGAAGCAGG | 1440 |
| CACTTTACAC | GGAGTCTGAC | GGGAGGTCAT | AGGCTATGGC | ATAGCAGAGG | CAGGGAGGTG | 1500 |
| GTGGAATTGG | ACTTCGCGCA | GAAGCTAAGC | ACACACCAGG | AATGACATAT | CCCTCCTATC | 1560 |
| TCCCCCATAA | GAGTTTAAGA | GTGACAGG | | | | 1588 |

( 2 ) INFORMATION FOR SEQ ID NO:11:

( i ) SEQUENCE CHARACTERISTICS:
        ( A ) LENGTH: 1679 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( C ) INDIVIDUAL ISOLATE: Mouse alpha MHC promoter fragment ( x i ) SEQUENCE DESCRIPTION: SEQ ID NO:11:

| | | | | | |
|---|---|---|---|---|---|
| GAATTCTCTT | ACTATCAAAG | GGAAACTGAG | TCGTGCACCT | GCAAAGTGGA | TGCTCTCCCT | 60 |
| AGACATCATG | ACTTTGTCTC | TGGGGAGCCA | GCACTGTGGA | ACTTCAGGTC | TGAGAGAGTA | 120 |
| GGAGGCTCCC | CTCAGCCTGA | AGCTATGCAG | ATAGCCAGGG | TTGAAAGGGG | GAAGGGAGAG | 180 |
| CCTGGGATGG | GAGCTTGTGT | GTTGGAGGCA | GGGGACAGAT | ATTAAGCCTG | GAAGAGAAGG | 240 |
| TGACCCTTAC | CCAGTTGTTC | AACTCACCCT | TCAGATTAAA | AATAACTGAG | GTAAGGGCCT | 300 |
| GGGTAGGGGA | GGTGGTGTGA | GACGCTCCTG | TCTCTCCTCT | ATCTGCCCAT | CGGCCCTTTG | 360 |
| GGGAGGAGGA | ATGTGCCCAA | GGACTAAAAA | AAGGCCATGG | AGCCAGAGGG | GCGAGGGCAA | 420 |
| CAGACCTTTC | ATGGGCAAAC | CTTGGGGCCC | TGCTGTCCTC | CTGTCACCTC | AGAGCCAAG | 480 |
| GGATCAAAGG | AGGAGGAGCC | AGGACAGGAG | GGAAGTGGGA | GGGAGGGTCC | CAGCAGAGGA | 540 |
| CTCCAAATTT | AGGCAGCAGG | CATATGGGAT | GGGATATAAA | GGGGCTGGAG | CACTGAGAGC | 600 |
| TGTCAGAGAT | TTCTCCAACC | CAGGTAAGAG | GGAGTTTCGG | GTGGGGCTC | TTCACCCACA | 660 |
| CCAGACCTCT | CCCCACCTAG | AAGGAAACTG | CCTTTCCTGG | AAGTGGGGTT | CAGGCCGGTC | 720 |
| AGAGATCTGA | CAGGGTGGCC | TTCCACCAGC | CTGGGAAGTT | CTCAGTGGCA | GGAGGTTTCC | 780 |
| ACAAGAAACA | CTGGATGCCC | CTTCCCTTAC | GCTGTCTTCT | CCATCTTCCT | CCTGGGGATG | 840 |
| CTCCTCCCCG | TCTTGGTTTA | TCTTGGCTCT | TCGTCTTCAG | CAAGATTTGC | CCTGTGCTGT | 900 |
| CCACTCCATC | TTTCTCTACT | GTCTCCGTGC | CTTGCCTTGC | CTTCTTGCGT | GTCCTTCCTT | 960 |
| TCCACCCATT | TCTCACTTCA | CCTTTTCTCC | CCTTCTCATT | TGTATTCATC | CTTCCTTCCT | 1020 |
| TCCTTCCTTC | CTTCCTTCCT | TCCTTCCTTC | CTTCCTTTCT | CCCTTCCTTC | CTTCCTTCCT | 1080 |
| TCCTTCCTTC | CTTCCTTCCT | TCCTGTGTCA | GAGTGCTGAG | AATCACACCT | GGGGTTCCCA | 1140 |
| CCCTTATGTA | AACAATCTTC | CAGTGAGCCA | CAGCTTCAGT | GCTGCTGGGT | GCTCTCTTAC | 1200 |
| CTTCCTCACC | CCCTGGCTTG | TCCTGTTCCA | TCCTGGTCAG | GATCTCTAGA | TTGGTCTCCC | 1260 |
| AGCCTCTGCT | ACTCCTCTTC | CTGCCTGTTC | CTCTCTCTGT | CCAGCTGCGC | CACTGTGGTG | 1320 |
| CCTCGTTCCA | GCTGTGGTCC | ACATTCTTCA | GGATTCTCTG | AAAAGTTAAC | CAGGTGAGAA | 1380 |
| TGTTTCCCCT | GTAGACAGCA | GATCACGATT | CTCCCGGAAG | TCAGGCTTCC | AGCCCTCTCT | 1440 |
| TTCTCTGCCC | AGCTGCCCGG | CACTCTTAGC | AAACCTCAGG | CACCCTTACC | CCACATAGAC | 1500 |
| CTCTGACAGA | GAAGCAGGCA | CTTTACATGG | AGTCCTGGTG | GGAGAGCCAT | AGGCTACGGT | 1560 |

(2) INFORMATION FOR SEQ ID NO:12:

(i) SEQUENCE CHARACTERISTICS:
        (A) LENGTH: 5057 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (C) INDIVIDUAL ISOLATE: rat bNOS cDNA (ix) FEATURE:
        (A) NAME/KEY: CDS
        (B) LOCATION: 349..4638

(xi) SEQUENCE DESCRIPTION: SEQ ID NO:12:

```
GTAAAAGAGG CAGGGAAGTG GTGGTGTAGG AAAGTCAGGA CTTCACATAG AAGCCTAGCC      1620

CACACCAGAA ATGACAGACA GATCCCTCCT ATCTCCCCA  TAAGAGTTTG AGTGACAGA       1679

ACGTCTGACA AGCTGGTGAC CAAGATGCCC AGAGACTAGA CCCTATGCTT GTGAGTCACA        60

GTCATCAGAC ACGGCAAACC TCCAGTCTTC CTGACCTGTT GCTTAGGGAC ACATCCCGTT       120

GCTGCCCCTG ACGTCTGCCT GGTCAACCTT GACTTCCTTT GAGAGTAAGG AAGGGGGCGG       180

GGACACGTTG AAATCATGCC ACCCAAGGCC GAATCGGAAT GAGCAGATGA CGCCAAGTTG       240

ACGTCAAAGA CAGAGGCGAC AGAAACTCTG CAGCCAGCTC TTGCCCCCGA GGAGCTCAGG       300

TTCCTGCAGG AGTCATTTTA GCTTAGTCTT CTGAAGGACA CAGATACC ATG GAA GAG       357
                                                    Met Glu Glu
                                                      1

AAC ACG TTT GGG GTT CAG CAG ATC CAA CCC AAT GTA ATT TCT GTT CGT       405
Asn Thr Phe Gly Val Gln Gln Ile Gln Pro Asn Val Ile Ser Val Arg
      5                  10                  15

CTC TTC AAA CGC AAA GTG GGA GGT CTG GGC TTC CTG GTG AAG GAA CGG       453
Leu Phe Lys Arg Lys Val Gly Gly Leu Gly Phe Leu Val Lys Glu Arg
 20                  25                  30                  35

GTC AGC AAG CCT CCC GTG ATC ATC TCA GAC CTG ATT CGA GGA GGT GCT       501
Val Ser Lys Pro Pro Val Ile Ile Ser Asp Leu Ile Arg Gly Gly Ala
                 40                  45                  50

GCG GAG CAG AGC GGC CTT ATC CAA GCT GGA GAC ATC ATT CTC GCA GTC       549
Ala Glu Gln Ser Gly Leu Ile Gln Ala Gly Asp Ile Ile Leu Ala Val
             55                  60                  65

AAC GAT CGG CCC TTG GTA GAC CTC AGC TAT GAC AGT GCC CTG GAG GTT       597
Asn Asp Arg Pro Leu Val Asp Leu Ser Tyr Asp Ser Ala Leu Glu Val
         70                  75                  80

CTC AGG GGC ATT GCC TCT GAG ACC CAC GTG GTC CTC ATT CTG AGG GGC       645
Leu Arg Gly Ile Ala Ser Glu Thr His Val Val Leu Ile Leu Arg Gly
     85                  90                  95

CCT GAG GGC TTC ACT ACA CAT CTG GAG ACC ACC TTC ACA GGG GAT GGA       693
Pro Glu Gly Phe Thr Thr His Leu Glu Thr Thr Phe Thr Gly Asp Gly
100                 105                 110                 115

ACC CCC AAG ACC ATC CGG GTG ACC CAG CCC CTC GGT CCT CCC ACC AAA       741
Thr Pro Lys Thr Ile Arg Val Thr Gln Pro Leu Gly Pro Pro Thr Lys
                120                 125                 130

GCC GTC GAT CTG TCT CAC CAG CCT TCA GCC AGC AAA GAC CAG TCA TTA       789
Ala Val Asp Leu Ser His Gln Pro Ser Ala Ser Lys Asp Gln Ser Leu
            135                 140                 145

GCA GTA GAC AGA GTC ACA GGT CTG GGT AAT GGC CCT CAG CAT GCC CAA       837
Ala Val Asp Arg Val Thr Gly Leu Gly Asn Gly Pro Gln His Ala Gln
```

-continued

|  |  |  | 150 |  |  |  |  | 155 |  |  |  |  | 160 |  |  |  |
|---|---|---|---|---|---|---|---|---|---|---|---|---|---|---|---|---|
| GGC | CAT | GGG | CAG | GGA | GCT | GGC | TCA | GTC | TCC | CAA | GCT | AAT | GGT | GTG | GCC | 885 |
| Gly | His | Gly | Gln | Gly | Ala | Gly | Ser | Val | Ser | Gln | Ala | Asn | Gly | Val | Ala |  |
|  | 165 |  |  |  |  | 170 |  |  |  | 175 |  |  |  |  |  |  |
| ATT | GAC | CCC | ACG | ATG | AAA | AGC | ACC | AAG | GCC | AAC | CTC | CAG | GAC | ATC | GGG | 933 |
| Ile | Asp | Pro | Thr | Met | Lys | Ser | Thr | Lys | Ala | Asn | Leu | Gln | Asp | Ile | Gly |  |
| 180 |  |  |  |  | 185 |  |  |  |  | 190 |  |  |  |  | 195 |  |
| GAA | CAT | GAT | GAA | CTG | CTC | AAA | GAG | ATA | GAA | CCT | GTG | CTG | AGC | ATC | CTC | 981 |
| Glu | His | Asp | Glu | Leu | Leu | Lys | Glu | Ile | Glu | Pro | Val | Leu | Ser | Ile | Leu |  |
|  |  |  |  | 200 |  |  |  | 205 |  |  |  |  |  | 210 |  |  |
| AAC | AGT | GGG | AGC | AAA | GCC | ACC | AAC | AGA | GGG | GGA | CCA | GCC | AAA | GCA | GAG | 1029 |
| Asn | Ser | Gly | Ser | Lys | Ala | Thr | Asn | Arg | Gly | Gly | Pro | Ala | Lys | Ala | Glu |  |
|  |  |  | 215 |  |  |  |  | 220 |  |  |  | 225 |  |  |  |  |
| ATG | AAA | GAC | ACA | GGA | ATC | CAG | GTG | GAC | AGA | GAC | CTC | GAT | GGC | AAA | TCG | 1077 |
| Met | Lys | Asp | Thr | Gly | Ile | Gln | Val | Asp | Arg | Asp | Leu | Asp | Gly | Lys | Ser |  |
|  |  | 230 |  |  |  |  | 235 |  |  |  |  | 240 |  |  |  |  |
| CAC | AAA | GCT | CCG | CCC | CTG | GGC | GGG | GAC | AAT | GAC | CGC | GTC | TTC | AAT | GAC | 1125 |
| His | Lys | Ala | Pro | Pro | Leu | Gly | Gly | Asp | Asn | Asp | Arg | Val | Phe | Asn | Asp |  |
|  | 245 |  |  |  |  | 250 |  |  |  |  | 255 |  |  |  |  |  |
| CTG | TGG | GGG | AAG | GAC | AAC | GTT | CCT | GTG | ATC | CTT | AAC | AAC | CCG | TAT | TCA | 1173 |
| Leu | Trp | Gly | Lys | Asp | Asn | Val | Pro | Val | Ile | Leu | Asn | Asn | Pro | Tyr | Ser |  |
| 260 |  |  |  |  | 265 |  |  |  |  | 270 |  |  |  |  | 275 |  |
| GAG | AAG | GAA | CAG | TCC | CCT | ACC | TCG | GGG | AAA | CAG | TCT | CCC | ACC | AAG | AAC | 1221 |
| Glu | Lys | Glu | Gln | Ser | Pro | Thr | Ser | Gly | Lys | Gln | Ser | Pro | Thr | Lys | Asn |  |
|  |  |  |  | 280 |  |  |  |  | 285 |  |  |  |  | 290 |  |  |
| GGC | AGC | CCT | TCC | AGG | TGC | CCC | CGT | TTC | CTC | AAG | GTC | AAG | AAC | TGG | GAG | 1269 |
| Gly | Ser | Pro | Ser | Arg | Cys | Pro | Arg | Phe | Leu | Lys | Val | Lys | Asn | Trp | Glu |  |
|  |  |  | 295 |  |  |  |  | 300 |  |  |  |  | 305 |  |  |  |
| ACG | GAC | GTG | GTC | CTC | ACC | GAC | ACC | CTG | CAC | CTG | AAG | AGC | ACA | CTG | GAA | 1317 |
| Thr | Asp | Val | Val | Leu | Thr | Asp | Thr | Leu | His | Leu | Lys | Ser | Thr | Leu | Glu |  |
|  |  |  | 310 |  |  |  |  | 315 |  |  |  |  | 320 |  |  |  |
| ACG | GGG | TGC | ACA | GAG | CAC | ATT | TGC | ATG | GGC | TCG | ATC | ATG | CTG | CCT | TCC | 1365 |
| Thr | Gly | Cys | Thr | Glu | His | Ile | Cys | Met | Gly | Ser | Ile | Met | Leu | Pro | Ser |  |
|  |  | 325 |  |  |  |  | 330 |  |  |  |  | 335 |  |  |  |  |
| CAG | CAC | ACG | CGG | AAG | CCA | GAA | GAT | GTC | CGC | ACA | AAG | GAC | CAG | CTC | TTC | 1413 |
| Gln | His | Thr | Arg | Lys | Pro | Glu | Asp | Val | Arg | Thr | Lys | Asp | Gln | Leu | Phe |  |
| 340 |  |  |  |  | 345 |  |  |  |  | 350 |  |  |  |  | 355 |  |
| CCT | CTA | GCC | AAA | GAA | TTT | CTC | GAC | CAA | TAC | TAC | TCA | TCC | ATT | AAG | AGA | 1461 |
| Pro | Leu | Ala | Lys | Glu | Phe | Leu | Asp | Gln | Tyr | Tyr | Ser | Ser | Ile | Lys | Arg |  |
|  |  |  |  | 360 |  |  |  |  | 365 |  |  |  |  | 370 |  |  |
| TTT | GGC | TCC | AAG | GCC | CAC | ATG | GAC | AGG | CTG | GAG | GAG | GTG | AAC | AAG | GAG | 1509 |
| Phe | Gly | Ser | Lys | Ala | His | Met | Asp | Arg | Leu | Glu | Glu | Val | Asn | Lys | Glu |  |
|  |  |  | 375 |  |  |  |  | 380 |  |  |  |  | 385 |  |  |  |
| ATT | GAA | AGC | ACC | AGC | ACC | TAC | CAG | CTC | AAG | GAC | ACC | GAG | CTC | ATC | TAT | 1557 |
| Ile | Glu | Ser | Thr | Ser | Thr | Tyr | Gln | Leu | Lys | Asp | Thr | Glu | Leu | Ile | Tyr |  |
|  |  | 390 |  |  |  |  | 395 |  |  |  |  | 400 |  |  |  |  |
| GGC | GCC | AAG | CAT | GCC | TGG | CGG | AAC | GCC | TCT | CGA | TGT | GTG | GGC | AGG | ATC | 1605 |
| Gly | Ala | Lys | His | Ala | Trp | Arg | Asn | Ala | Ser | Arg | Cys | Val | Gly | Arg | Ile |  |
|  | 405 |  |  |  |  | 410 |  |  |  |  | 415 |  |  |  |  |  |
| CAG | TGG | TCC | AAG | CTG | CAG | GTG | TTC | GAT | GCC | CGA | GAC | TGC | ACC | ACA | GCC | 1653 |
| Gln | Trp | Ser | Lys | Leu | Gln | Val | Phe | Asp | Ala | Arg | Asp | Cys | Thr | Thr | Ala |  |
| 420 |  |  |  |  | 425 |  |  |  |  | 430 |  |  |  |  | 435 |  |
| CAC | GGC | ATG | TTC | AAC | TAC | ATC | TGT | AAC | CAT | GTC | AAG | TAT | GCC | ACC | AAC | 1701 |
| His | Gly | Met | Phe | Asn | Tyr | Ile | Cys | Asn | His | Val | Lys | Tyr | Ala | Thr | Asn |  |
|  |  |  |  | 440 |  |  |  |  | 445 |  |  |  |  | 450 |  |  |
| AAA | GGG | AAT | CTC | AGG | TCG | GCC | ATC | ACG | ATA | TTC | CCT | CAG | AGG | ACT | GAC | 1749 |
| Lys | Gly | Asn | Leu | Arg | Ser | Ala | Ile | Thr | Ile | Phe | Pro | Gln | Arg | Thr | Asp |  |
|  |  |  | 455 |  |  |  |  | 460 |  |  |  |  | 465 |  |  |  |
| GGC | AAA | CAT | GAC | TTC | CGA | GTG | TGG | AAC | TCG | CAG | CTC | ATC | CGC | TAC | GCG | 1797 |
| Gly | Lys | His | Asp | Phe | Arg | Val | Trp | Asn | Ser | Gln | Leu | Ile | Arg | Tyr | Ala |  |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     |     |     | 470 |     |     |     |     | 475 |     |     |     |     | 480 |     |     |      |
| GGC | TAC | AAG | CAG | CCA | GAT | GGC | TCT | ACC | TTG | GGG | GAT | CCA | GCC | AAT | GTG | 1845 |
| Gly | Tyr | Lys | Gln | Pro | Asp | Gly | Ser | Thr | Leu | Gly | Asp | Pro | Ala | Asn | Val |      |
|     | 485 |     |     |     |     | 490 |     |     |     |     | 495 |     |     |     |     |      |
| CAG | TTC | ACG | GAG | ATC | TGT | ATA | CAG | CAG | GGC | TGG | AAA | GCC | CCA | AGA | GGC | 1893 |
| Gln | Phe | Thr | Glu | Ile | Cys | Ile | Gln | Gln | Gly | Trp | Lys | Ala | Pro | Arg | Gly |      |
| 500 |     |     |     |     | 505 |     |     |     |     | 510 |     |     |     |     | 515 |      |
| CGC | TTC | GAC | GTG | CTG | CCT | CTC | CTG | CTT | CAG | GCC | AAT | GGC | AAT | GAC | CCT | 1941 |
| Arg | Phe | Asp | Val | Leu | Pro | Leu | Leu | Leu | Gln | Ala | Asn | Gly | Asn | Asp | Pro |      |
|     |     |     |     | 520 |     |     |     |     | 525 |     |     |     |     | 530 |     |      |
| GAG | CTC | TTC | CAG | ATC | CCC | CCA | GAG | CTG | GTG | CTG | GAA | GTG | CCC | ATC | AGG | 1989 |
| Glu | Leu | Phe | Gln | Ile | Pro | Pro | Glu | Leu | Val | Leu | Glu | Val | Pro | Ile | Arg |      |
|     |     |     | 535 |     |     |     |     | 540 |     |     |     |     | 545 |     |     |      |
| CAC | CCC | AAG | TTC | GAC | TGG | TTT | AAG | GAC | CTG | GGG | CTC | AAA | TGG | TAT | GGC | 2037 |
| His | Pro | Lys | Phe | Asp | Trp | Phe | Lys | Asp | Leu | Gly | Leu | Lys | Trp | Tyr | Gly |      |
|     |     | 550 |     |     |     |     | 555 |     |     |     |     | 560 |     |     |     |      |
| CTC | CCC | GCT | GTG | TCC | AAC | ATG | CTG | CTG | GAG | ATC | GGG | GGC | CTG | GAG | TTC | 2085 |
| Leu | Pro | Ala | Val | Ser | Asn | Met | Leu | Leu | Glu | Ile | Gly | Gly | Leu | Glu | Phe |      |
| 565 |     |     |     |     | 570 |     |     |     |     | 575 |     |     |     |     |     |      |
| AGC | GCC | TGT | CCC | TTC | AGC | GGC | TGG | TAC | ATG | GGC | ACA | GAG | ATC | GGC | GTC | 2133 |
| Ser | Ala | Cys | Pro | Phe | Ser | Gly | Trp | Tyr | Met | Gly | Thr | Glu | Ile | Gly | Val |      |
| 580 |     |     |     |     | 585 |     |     |     |     | 590 |     |     |     |     | 595 |      |
| CGT | GAC | TAC | TGT | GAC | AAC | TCT | CGA | TAC | AAC | ATC | CTG | GAG | GAA | GTA | GCC | 2181 |
| Arg | Asp | Tyr | Cys | Asp | Asn | Ser | Arg | Tyr | Asn | Ile | Leu | Glu | Glu | Val | Ala |      |
|     |     |     |     | 600 |     |     |     |     | 605 |     |     |     |     | 610 |     |      |
| AAG | AAG | ATG | GAT | TTG | GAC | ATG | AGG | AAG | ACC | TCG | TCC | CTC | TGG | AAG | GAC | 2229 |
| Lys | Lys | Met | Asp | Leu | Asp | Met | Arg | Lys | Thr | Ser | Ser | Leu | Trp | Lys | Asp |      |
|     |     |     | 615 |     |     |     |     | 620 |     |     |     |     | 625 |     |     |      |
| CAA | GCA | CTG | GTG | GAG | ATC | AAC | ATT | GCT | GTT | CTA | TAT | AGC | TTC | CAG | AGT | 2277 |
| Gln | Ala | Leu | Val | Glu | Ile | Asn | Ile | Ala | Val | Leu | Tyr | Ser | Phe | Gln | Ser |      |
|     |     | 630 |     |     |     |     | 635 |     |     |     |     | 640 |     |     |     |      |
| GAC | AAG | GTG | ACC | ATC | GTT | GAC | CAC | CAC | TCT | GCC | ACG | GAG | TCC | TTC | ATC | 2325 |
| Asp | Lys | Val | Thr | Ile | Val | Asp | His | His | Ser | Ala | Thr | Glu | Ser | Phe | Ile |      |
|     | 645 |     |     |     |     | 650 |     |     |     |     | 655 |     |     |     |     |      |
| AAA | CAC | ATG | GAG | AAT | GAA | TAC | CGC | TGC | AGA | GGG | GGC | TGC | CCC | GCC | GAC | 2373 |
| Lys | His | Met | Glu | Asn | Glu | Tyr | Arg | Cys | Arg | Gly | Gly | Cys | Pro | Ala | Asp |      |
| 660 |     |     |     |     | 665 |     |     |     |     | 670 |     |     |     |     | 675 |      |
| TGG | GTG | TGG | ATT | GTG | CCT | CCC | ATG | TCG | GGC | AGC | ATC | ACC | CCT | GTC | TTC | 2421 |
| Trp | Val | Trp | Ile | Val | Pro | Pro | Met | Ser | Gly | Ser | Ile | Thr | Pro | Val | Phe |      |
|     |     |     |     | 680 |     |     |     |     | 685 |     |     |     |     | 690 |     |      |
| CAC | CAG | GAG | ATG | CTC | AAC | TAT | AGA | CTC | ACC | CCG | TCC | TTT | GAA | TAC | CAG | 2469 |
| His | Gln | Glu | Met | Leu | Asn | Tyr | Arg | Leu | Thr | Pro | Ser | Phe | Glu | Tyr | Gln |      |
|     |     |     | 695 |     |     |     |     | 700 |     |     |     |     | 705 |     |     |      |
| CCT | GAT | CCA | TGG | AAC | ACC | CAC | GTG | TGG | AAG | GGC | ACC | AAC | GGG | ACC | CCC | 2517 |
| Pro | Asp | Pro | Trp | Asn | Thr | His | Val | Trp | Lys | Gly | Thr | Asn | Gly | Thr | Pro |      |
|     |     | 710 |     |     |     |     | 715 |     |     |     |     | 720 |     |     |     |      |
| ACG | AAG | CGG | CGA | GCT | ATC | GGC | TTT | AAG | AAA | TTG | GCA | GAG | GCC | GTC | AAG | 2565 |
| Thr | Lys | Arg | Arg | Ala | Ile | Gly | Phe | Lys | Lys | Leu | Ala | Glu | Ala | Val | Lys |      |
|     | 725 |     |     |     |     | 730 |     |     |     |     | 735 |     |     |     |     |      |
| TTC | TCA | GCC | AAG | CTA | ATG | GGG | CAG | GCC | ATG | GCC | AAG | AGG | GTC | AAG | GCG | 2613 |
| Phe | Ser | Ala | Lys | Leu | Met | Gly | Gln | Ala | Met | Ala | Lys | Arg | Val | Lys | Ala |      |
| 740 |     |     |     |     | 745 |     |     |     |     | 750 |     |     |     |     | 755 |      |
| ACC | ATT | CTC | TAC | GCC | ACA | GAG | ACA | GGC | AAA | TCA | CAA | GCC | TAT | GCC | AAG | 2661 |
| Thr | Ile | Leu | Tyr | Ala | Thr | Glu | Thr | Gly | Lys | Ser | Gln | Ala | Tyr | Ala | Lys |      |
|     |     |     |     | 760 |     |     |     |     | 765 |     |     |     |     | 770 |     |      |
| ACC | CTG | TGT | GAG | ATC | TTC | AAG | CAC | GCC | TTC | GAT | GCC | AAG | GCA | ATG | TCC | 2709 |
| Thr | Leu | Cys | Glu | Ile | Phe | Lys | His | Ala | Phe | Asp | Ala | Lys | Ala | Met | Ser |      |
|     |     |     | 775 |     |     |     |     | 780 |     |     |     |     | 785 |     |     |      |
| ATG | GAG | GAG | TAT | GAC | ATC | GTG | CAC | CTG | GAG | CAC | GAA | GCC | CTG | GTC | TTG | 2757 |
| Met | Glu | Glu | Tyr | Asp | Ile | Val | His | Leu | Glu | His | Glu | Ala | Leu | Val | Leu |      |

-continued

```
              790                         795                         800
GTG  GTC  ACC  AGC  ACC  TTT  GGC  AAT  GGA  GAC  CCC  CCT  GAG  AAC  GGG  GAG    2805
Val  Val  Thr  Ser  Thr  Phe  Gly  Asn  Gly  Asp  Pro  Pro  Glu  Asn  Gly  Glu
805                      810                      815

AAA  TTC  GGC  TGT  GCT  TTA  ATG  GAG  ATG  AGG  CAC  CCC  AAC  TCT  GTG  CAG    2853
Lys  Phe  Gly  Cys  Ala  Leu  Met  Glu  Met  Arg  His  Pro  Asn  Ser  Val  Gln
820                      825                      830                      835

GAG  GAG  AGA  AAG  AGC  TAC  AAG  GTC  CGA  TTC  AAC  AGC  GTC  TCC  TCC  TAT    2901
Glu  Glu  Arg  Lys  Ser  Tyr  Lys  Val  Arg  Phe  Asn  Ser  Val  Ser  Ser  Tyr
                         840                      845                      850

TCT  GAC  TCC  CGA  AAG  TCA  TCG  GGC  GAC  GGA  CCC  GAC  CTC  AGA  GAC  AAC    2949
Ser  Asp  Ser  Arg  Lys  Ser  Ser  Gly  Asp  Gly  Pro  Asp  Leu  Arg  Asp  Asn
               855                      860                      865

TTT  GAA  AGT  ACT  GGA  CCC  CTG  GCC  AAT  GTG  AGG  TTC  TCA  GTG  TTC  GGC    2997
Phe  Glu  Ser  Thr  Gly  Pro  Leu  Ala  Asn  Val  Arg  Phe  Ser  Val  Phe  Gly
          870                      875                      880

CTC  GGC  TCT  CGG  GCG  TAC  CCC  CAC  TTC  TGT  GCC  TTT  GGG  CAT  GCG  GTG    3045
Leu  Gly  Ser  Arg  Ala  Tyr  Pro  His  Phe  Cys  Ala  Phe  Gly  His  Ala  Val
885                      890                      895

GAC  ACC  CTC  CTG  GAG  GAA  CTG  GGA  GGG  GAG  AGG  ATT  CTG  AAG  ATG  AGG    3093
Asp  Thr  Leu  Leu  Glu  Glu  Leu  Gly  Gly  Glu  Arg  Ile  Leu  Lys  Met  Arg
900                      905                      910                      915

GAG  GGG  GAT  GAG  CTT  TGC  GGA  CAG  GAA  GAA  GCT  TTC  AGG  ACC  TGG  GCC    3141
Glu  Gly  Asp  Glu  Leu  Cys  Gly  Gln  Glu  Glu  Ala  Phe  Arg  Thr  Trp  Ala
                         920                      925                      930

AAG  AAA  GTC  TTC  AAG  GCA  GCC  TGT  GAT  GTG  TTC  TGC  GTG  GGG  GAT  GAC    3189
Lys  Lys  Val  Phe  Lys  Ala  Ala  Cys  Asp  Val  Phe  Cys  Val  Gly  Asp  Asp
               935                      940                      945

GTC  AAC  ATC  GAG  AAG  CCG  AAC  AAC  TCC  CTC  ATT  AGC  AAT  GAC  CGA  AGC    3237
Val  Asn  Ile  Glu  Lys  Pro  Asn  Asn  Ser  Leu  Ile  Ser  Asn  Asp  Arg  Ser
          950                      955                      960

TGG  AAG  AGG  AAC  AAG  TTC  CGC  CTC  ACG  TAT  GTG  GCG  GAA  GCT  CCA  GAT    3285
Trp  Lys  Arg  Asn  Lys  Phe  Arg  Leu  Thr  Tyr  Val  Ala  Glu  Ala  Pro  Asp
965                      970                      975

CTG  ACC  CAA  GGT  CTT  TCC  AAT  GTT  CAC  AAA  AAA  CGA  GTC  TCG  GCT  GCT    3333
Leu  Thr  Gln  Gly  Leu  Ser  Asn  Val  His  Lys  Lys  Arg  Val  Ser  Ala  Ala
980                      985                      990                      995

CGA  CTC  CTC  AGC  CGC  CAA  AAC  CTG  CAA  AGC  CCT  AAG  TTC  AGC  CGA  TCG    3381
Arg  Leu  Leu  Ser  Arg  Gln  Asn  Leu  Gln  Ser  Pro  Lys  Phe  Ser  Arg  Ser
                         1000                     1005                    1010

ACC  ATC  TTC  GTG  CGT  CTC  CAC  ACC  AAC  GGG  AAT  CAG  GAG  CTG  CAG  TAC    3429
Thr  Ile  Phe  Val  Arg  Leu  His  Thr  Asn  Gly  Asn  Gln  Glu  Leu  Gln  Tyr
               1015                     1020                    1025

CAG  CCA  GGG  GAC  CAC  CTG  GGT  GTC  TTC  CCC  GGC  AAC  CAC  GAG  GAC  CTC    3477
Gln  Pro  Gly  Asp  His  Leu  Gly  Val  Phe  Pro  Gly  Asn  His  Glu  Asp  Leu
          1030                     1035                    1040

GTG  AAT  GCA  CTC  ATT  GAA  CGG  CTG  GAG  GAT  GCA  CCG  CCT  GCC  AAC  CAC    3525
Val  Asn  Ala  Leu  Ile  Glu  Arg  Leu  Glu  Asp  Ala  Pro  Pro  Ala  Asn  His
1045                     1050                    1055

GTG  GTG  AAG  GTG  GAG  ATG  CTG  GAG  GAG  AGG  AAC  ACT  GCT  CTG  GGT  GTC    3573
Val  Val  Lys  Val  Glu  Met  Leu  Glu  Glu  Arg  Asn  Thr  Ala  Leu  Gly  Val
1060                     1065                    1070                    1075

ATC  AGT  AAT  TGG  AAG  GAT  GAA  TCT  CGC  CTC  CCA  CCC  TGC  ACC  ATC  TTC    3621
Ile  Ser  Asn  Trp  Lys  Asp  Glu  Ser  Arg  Leu  Pro  Pro  Cys  Thr  Ile  Phe
               1080                     1085                    1090

CAG  GCC  TTC  AAG  TAC  TAC  CTG  GAC  ATC  ACC  ACG  CCG  CCC  ACG  CCC  CTG    3669
Gln  Ala  Phe  Lys  Tyr  Tyr  Leu  Asp  Ile  Thr  Thr  Pro  Pro  Thr  Pro  Leu
          1095                     1100                    1105

CAG  CTG  CAG  CAG  TTC  GCC  TCT  CTG  GCC  ACT  AAT  GAG  AAA  GAG  AAG  CAG    3717
Gln  Leu  Gln  Gln  Phe  Ala  Ser  Leu  Ala  Thr  Asn  Glu  Lys  Glu  Lys  Gln
```

```
                    1110                      1115                      1120
CGG  TTG  CTG  GTC  CTC  AGC  AAG  GGG  CTC  CAG  GAA  TAT  GAG  GAG  TGG  AAG         3765
Arg  Leu  Leu  Val  Leu  Ser  Lys  Gly  Leu  Gln  Glu  Tyr  Glu  Glu  Trp  Lys
1125                     1130                          1135

TGG  GGC  AAG  AAC  CCC  ACA  ATG  GTG  GAG  GTG  CTG  GAG  GAG  TTC  CCG  TCC         3813
Trp  Gly  Lys  Asn  Pro  Thr  Met  Val  Glu  Val  Leu  Glu  Glu  Phe  Pro  Ser
1140                     1145                          1150                     1155

ATC  CAG  ATG  CCG  GCT  ACA  CTT  CTC  CTC  ACT  CAG  CTG  TCG  CTG  CTG  CAG         3861
Ile  Gln  Met  Pro  Ala  Thr  Leu  Leu  Leu  Thr  Gln  Leu  Ser  Leu  Leu  Gln
                         1160                          1165                     1170

CCT  CGC  TAC  TAC  TCC  ATC  AGC  TCC  TCT  CCA  GAC  ATG  TAC  CCC  GAC  GAG         3909
Pro  Arg  Tyr  Tyr  Ser  Ile  Ser  Ser  Ser  Pro  Asp  Met  Tyr  Pro  Asp  Glu
                    1175                          1180                     1185

GTG  CAC  CTC  ACT  GTG  GCC  ATC  GTC  TCC  TAC  CAC  ACC  CGA  GAC  GGA  GAA         3957
Val  His  Leu  Thr  Val  Ala  Ile  Val  Ser  Tyr  His  Thr  Arg  Asp  Gly  Glu
                         1190                          1195                     1200

GGA  CCA  GTC  CAC  CAC  GGG  GTG  TGC  TCC  TCC  TGG  CTC  AAC  AGA  ATA  CAG         4005
Gly  Pro  Val  His  His  Gly  Val  Cys  Ser  Ser  Trp  Leu  Asn  Arg  Ile  Gln
1205                          1210                          1215

GCT  GAC  GAT  GTA  GTC  CCC  TGC  TTC  GTG  AGA  GGT  GCC  CCT  AGC  TTC  CAC         4053
Ala  Asp  Asp  Val  Val  Pro  Cys  Phe  Val  Arg  Gly  Ala  Pro  Ser  Phe  His
1220                          1225                          1230                1235

CTG  CCT  CGA  AAC  CCC  CAG  GTG  CCT  TGC  ATC  CTG  GTT  GGC  CCA  GGC  ACT         4101
Leu  Pro  Arg  Asn  Pro  Gln  Val  Pro  Cys  Ile  Leu  Val  Gly  Pro  Gly  Thr
                         1240                          1245                     1250

GGC  ATC  GCA  CCC  TTC  CGA  AGC  TTC  TGG  CAA  CAG  CGA  CAA  TTT  GAC  ATC         4149
Gly  Ile  Ala  Pro  Phe  Arg  Ser  Phe  Trp  Gln  Gln  Arg  Gln  Phe  Asp  Ile
                    1255                          1260                     1265

CAA  CAC  AAA  GGA  ATG  AAT  CCG  TGC  CCC  ATG  GTT  CTG  GTC  TTC  GGG  TGT         4197
Gln  His  Lys  Gly  Met  Asn  Pro  Cys  Pro  Met  Val  Leu  Val  Phe  Gly  Cys
                    1270                          1275                     1280

CGA  CAA  TCC  AAG  ATA  GAT  CAT  ATC  TAC  AGA  GAG  GAG  ACC  CTG  CAG  GCT         4245
Arg  Gln  Ser  Lys  Ile  Asp  His  Ile  Tyr  Arg  Glu  Glu  Thr  Leu  Gln  Ala
                    1285                          1290                     1295

AAG  AAC  AAG  GGC  GTC  TTC  AGA  GAG  CTG  TAC  ACT  GCC  TAT  TCC  CGG  GAA         4293
Lys  Asn  Lys  Gly  Val  Phe  Arg  Glu  Leu  Tyr  Thr  Ala  Tyr  Ser  Arg  Glu
1300                          1305                          1310                1315

CCG  GAC  AGG  CCA  AAG  AAA  TAT  GTA  CAG  GAC  GTG  CTG  CAG  GAA  CAG  CTG         4341
Pro  Asp  Arg  Pro  Lys  Lys  Tyr  Val  Gln  Asp  Val  Leu  Gln  Glu  Gln  Leu
                         1320                          1325                     1330

GCT  GAG  TCT  GTG  TAC  CGC  GCC  CTG  AAG  GAG  CAA  GGA  GGC  CAC  ATT  TAT         4389
Ala  Glu  Ser  Val  Tyr  Arg  Ala  Leu  Lys  Glu  Gln  Gly  Gly  His  Ile  Tyr
                    1335                          1340                     1345

GTC  TGT  GGG  GAC  GTT  ACC  ATG  GCC  GCC  GAT  GTC  CTC  AAA  GCC  ATC  CAG         4437
Val  Cys  Gly  Asp  Val  Thr  Met  Ala  Ala  Asp  Val  Leu  Lys  Ala  Ile  Gln
                         1350                          1355                     1360

CGC  ATA  ATG  ACC  CAG  CAG  GGG  AAA  CTC  TCA  GAG  GAG  GAC  GCT  GGT  GTA         4485
Arg  Ile  Met  Thr  Gln  Gln  Gly  Lys  Leu  Ser  Glu  Glu  Asp  Ala  Gly  Val
1365                          1370                          1375

TTC  ATC  AGC  AGG  CTG  AGG  GAT  GAC  AAC  CGG  TAC  CAC  GAG  GAC  ATC  TTT         4533
Phe  Ile  Ser  Arg  Leu  Arg  Asp  Asp  Asn  Arg  Tyr  His  Glu  Asp  Ile  Phe
1380                          1385                          1390                1395

GGA  GTC  ACC  CTC  AGA  ACG  TAT  GAA  GTG  ACC  AAC  CGC  CTT  AGA  TCT  GAG         4581
Gly  Val  Thr  Leu  Arg  Thr  Tyr  Glu  Val  Thr  Asn  Arg  Leu  Arg  Ser  Glu
                         1400                          1405                     1410

TCC  ATC  GCC  TTC  ATC  GAA  GAG  AGC  AAA  AAA  GAC  GCA  GAT  GAG  GTT  TTC         4629
Ser  Ile  Ala  Phe  Ile  Glu  Glu  Ser  Lys  Lys  Asp  Ala  Asp  Glu  Val  Phe
                    1415                          1420                     1425

AGC  TCC   TAACTGGATC  CTCCTGCCCC  CGTGCGTGCG  ATGTGGCGGC  TGCCCCAAGT              4685
Ser  Ser
```

```
                    1 4 3

GCCCAAGTAA  GGGCGGCCGC  AGGTTGACTA  AATTCGGACA  CACACGGCTG  AACCGAGTGG     4 7 4 5

CCCTGCTCTG  CCTCTTGTCC  TGTTGCTGTG  TCCTGGTCCT  TCTTCCTGCT  CTGGGCTCTC     4 8 0 5

TCAACCCCAC  CCCTGGGTTT  TCTCCTTGAC  TCTTGGGCTA  CGATGCATCA  CCCTTGTACC     4 8 6 5

CTGCAGTGGC  TCTCACAAAA  CCGCATCCTC  CCCACCCCCA  CCCGATTGCT  GCCAAGGGCA     4 9 2 5

GGTTGCGGTG  CATGGCTGTT  GCTCCTGTTG  TTGGGGTCTG  AAGGTGGCTG  GCGCTGGGCC     4 9 8 5

TCAGGTCACC  CTGAACCAGT  CCCTTGGCCA  CTTAAGCCCC  CTTCCACCCT  CTTTTTATGA     5 0 4 5

TGGTGTGTTT  GT                                                              5 0 5 7
```

( 2 ) INFORMATION FOR SEQ ID NO:13:

( i ) SEQUENCE CHARACTERISTICS:
        ( A ) LENGTH: 1429 amino acids
        ( B ) TYPE: amino acid
        ( D ) TOPOLOGY: linear ( i i ) MOLECULE TYPE: protein ( x i ) SEQUENCE DESCRIPTION: SEQ ID NO:13:

```
Met  Glu  Glu  Asn  Thr  Phe  Gly  Val  Gln  Gln  Ile  Gln  Pro  Asn  Val  Ile
 1                    5                        1 0                         1 5

Ser  Val  Arg  Leu  Phe  Lys  Arg  Lys  Val  Gly  Gly  Leu  Gly  Phe  Leu  Val
               2 0                   2 5                         3 0

Lys  Glu  Arg  Val  Ser  Lys  Pro  Pro  Val  Ile  Ile  Ser  Asp  Leu  Ile  Arg
          3 5                   4 0                        4 5

Gly  Gly  Ala  Ala  Glu  Gln  Ser  Gly  Leu  Ile  Gln  Ala  Gly  Asp  Ile  Ile
     5 0                   5 5                        6 0

Leu  Ala  Val  Asn  Asp  Arg  Pro  Leu  Val  Asp  Leu  Ser  Tyr  Asp  Ser  Ala
6 5                    7 0                        7 5                    8 0

Leu  Glu  Val  Leu  Arg  Gly  Ile  Ala  Ser  Glu  Thr  His  Val  Val  Leu  Ile
               8 5                   9 0                         9 5

Leu  Arg  Gly  Pro  Glu  Gly  Phe  Thr  Thr  His  Leu  Glu  Thr  Thr  Phe  Thr
               1 0 0                 1 0 5                       1 1 0

Gly  Asp  Gly  Thr  Pro  Lys  Thr  Ile  Arg  Val  Thr  Gln  Pro  Leu  Gly  Pro
               1 1 5                 1 2 0                       1 2 5

Pro  Thr  Lys  Ala  Val  Asp  Leu  Ser  His  Gln  Pro  Ser  Ala  Ser  Lys  Asp
     1 3 0                 1 3 5                       1 4 0

Gln  Ser  Leu  Ala  Val  Asp  Arg  Val  Thr  Gly  Leu  Gly  Asn  Gly  Pro  Gln
1 4 5                  1 5 0                       1 5 5                  1 6 0

His  Ala  Gln  Gly  His  Gly  Gln  Gly  Ala  Gly  Ser  Val  Ser  Gln  Ala  Asn
                     1 6 5                 1 7 0                       1 7 5

Gly  Val  Ala  Ile  Asp  Pro  Thr  Met  Lys  Ser  Thr  Lys  Ala  Asn  Leu  Gln
               1 8 0                 1 8 5                       1 9 0

Asp  Ile  Gly  Glu  His  Asp  Glu  Leu  Leu  Lys  Glu  Ile  Glu  Pro  Val  Leu
          1 9 5                 2 0 0                       2 0 5

Ser  Ile  Leu  Asn  Ser  Gly  Ser  Lys  Ala  Thr  Asn  Arg  Gly  Gly  Pro  Ala
     2 1 0                 2 1 5                       2 2 0

Lys  Ala  Glu  Met  Lys  Asp  Thr  Gly  Ile  Gln  Val  Asp  Arg  Asp  Leu  Asp
2 2 5                  2 3 0                       2 3 5                  2 4 0

Gly  Lys  Ser  His  Lys  Ala  Pro  Pro  Leu  Gly  Asp  Asn  Asp  Arg  Val
                     2 4 5                 2 5 0                       2 5 5

Phe  Asn  Asp  Leu  Trp  Gly  Lys  Asp  Asn  Val  Pro  Val  Ile  Leu  Asn  Asn
               2 6 0                 2 6 5                       2 7 0

Pro  Tyr  Ser  Glu  Lys  Glu  Gln  Ser  Pro  Thr  Ser  Gly  Lys  Gln  Ser  Pro
```

|         |     |     |     |     | 275 |     |     |     |     | 280 |     |     |     |     | 285 |     |
|---------|-----|-----|-----|-----|-----|-----|-----|-----|-----|-----|-----|-----|-----|-----|-----|-----|

Thr Lys Asn Gly Ser Pro Ser Arg Cys Pro Arg Phe Leu Lys Val Lys
        290                 295                 300

Asn Trp Glu Thr Asp Val Val Leu Thr Asp Thr Leu His Leu Lys Ser
305                 310                 315                 320

Thr Leu Glu Thr Gly Cys Thr Glu His Ile Cys Met Gly Ser Ile Met
                    325                 330                 335

Leu Pro Ser Gln His Thr Arg Lys Pro Glu Asp Val Arg Thr Lys Asp
            340                 345                 350

Gln Leu Phe Pro Leu Ala Lys Glu Phe Leu Asp Gln Tyr Tyr Ser Ser
        355                 360                 365

Ile Lys Arg Phe Gly Ser Lys Ala His Met Asp Arg Leu Glu Glu Val
        370                 375                 380

Asn Lys Glu Ile Glu Ser Thr Ser Thr Tyr Gln Leu Lys Asp Thr Glu
385                 390                 395                 400

Leu Ile Tyr Gly Ala Lys His Ala Trp Arg Asn Ala Ser Arg Cys Val
                    405                 410                 415

Gly Arg Ile Gln Trp Ser Lys Leu Gln Val Phe Asp Ala Arg Asp Cys
            420                 425                 430

Thr Thr Ala His Gly Met Phe Asn Tyr Ile Cys Asn His Val Lys Tyr
            435                 440                 445

Ala Thr Asn Lys Gly Asn Leu Arg Ser Ala Ile Thr Ile Phe Pro Gln
450                 455                 460

Arg Thr Asp Gly Lys His Asp Phe Arg Val Trp Asn Ser Gln Leu Ile
465                 470                 475                 480

Arg Tyr Ala Gly Tyr Lys Gln Pro Asp Gly Ser Thr Leu Gly Asp Pro
                    485                 490                 495

Ala Asn Val Gln Phe Thr Glu Ile Cys Ile Gln Gln Gly Trp Lys Ala
            500                 505                 510

Pro Arg Gly Arg Phe Asp Val Leu Pro Leu Leu Leu Gln Ala Asn Gly
            515                 520                 525

Asn Asp Pro Glu Leu Phe Gln Ile Pro Pro Glu Leu Val Leu Glu Val
530                 535                 540

Pro Ile Arg His Pro Lys Phe Asp Trp Phe Lys Asp Leu Gly Leu Lys
545                 550                 555                 560

Trp Tyr Gly Leu Pro Ala Val Ser Asn Met Leu Leu Glu Ile Gly Gly
                    565                 570                 575

Leu Glu Phe Ser Ala Cys Pro Phe Ser Gly Trp Tyr Met Gly Thr Glu
            580                 585                 590

Ile Gly Val Arg Asp Tyr Cys Asp Asn Ser Arg Tyr Asn Ile Leu Glu
            595                 600                 605

Glu Val Ala Lys Lys Met Asp Leu Asp Met Arg Lys Thr Ser Ser Leu
610                 615                 620

Trp Lys Asp Gln Ala Leu Val Glu Ile Asn Ile Ala Val Leu Tyr Ser
625                 630                 635                 640

Phe Gln Ser Asp Lys Val Thr Ile Val Asp His His Ser Ala Thr Glu
                    645                 650                 655

Ser Phe Ile Lys His Met Glu Asn Glu Tyr Arg Cys Arg Gly Gly Cys
            660                 665                 670

Pro Ala Asp Trp Val Trp Ile Val Pro Pro Met Ser Gly Ser Ile Thr
            675                 680                 685

Pro Val Phe His Gln Glu Met Leu Asn Tyr Arg Leu Thr Pro Ser Phe
    690                 695                 700

```
Glu  Tyr  Gln  Pro  Asp  Pro  Trp  Asn  Thr  His  Val  Trp  Lys  Gly  Thr  Asn
705                 710                 715                 720

Gly  Thr  Pro  Thr  Lys  Arg  Arg  Ala  Ile  Gly  Phe  Lys  Lys  Leu  Ala  Glu
                    725                 730                 735

Ala  Val  Lys  Phe  Ser  Ala  Lys  Leu  Met  Gly  Gln  Ala  Met  Ala  Lys  Arg
               740                 745                 750

Val  Lys  Ala  Thr  Ile  Leu  Tyr  Ala  Thr  Glu  Thr  Gly  Lys  Ser  Gln  Ala
          755                 760                 765

Tyr  Ala  Lys  Thr  Leu  Cys  Glu  Ile  Phe  Lys  His  Ala  Phe  Asp  Ala  Lys
     770                 775                 780

Ala  Met  Ser  Met  Glu  Glu  Tyr  Asp  Ile  Val  His  Leu  Glu  His  Glu  Ala
785                 790                 795                 800

Leu  Val  Leu  Val  Val  Thr  Ser  Thr  Phe  Gly  Asn  Gly  Asp  Pro  Pro  Glu
                    805                 810                 815

Asn  Gly  Glu  Lys  Phe  Gly  Cys  Ala  Leu  Met  Glu  Met  Arg  His  Pro  Asn
               820                 825                 830

Ser  Val  Gln  Glu  Glu  Arg  Lys  Ser  Tyr  Lys  Val  Arg  Phe  Asn  Ser  Val
          835                 840                 845

Ser  Ser  Tyr  Ser  Asp  Ser  Arg  Lys  Ser  Ser  Gly  Asp  Gly  Pro  Asp  Leu
     850                 855                 860

Arg  Asp  Asn  Phe  Glu  Ser  Thr  Gly  Pro  Leu  Ala  Asn  Val  Arg  Phe  Ser
865                 870                 875                 880

Val  Phe  Gly  Leu  Gly  Ser  Arg  Ala  Tyr  Pro  His  Phe  Cys  Ala  Phe  Gly
                    885                 890                 895

His  Ala  Val  Asp  Thr  Leu  Leu  Glu  Glu  Leu  Gly  Gly  Glu  Arg  Ile  Leu
               900                 905                 910

Lys  Met  Arg  Glu  Gly  Asp  Glu  Leu  Cys  Gly  Gln  Glu  Glu  Ala  Phe  Arg
          915                 920                 925

Thr  Trp  Ala  Lys  Lys  Val  Phe  Lys  Ala  Ala  Cys  Asp  Val  Phe  Cys  Val
     930                 935                 940

Gly  Asp  Asp  Val  Asn  Ile  Glu  Lys  Pro  Asn  Asn  Ser  Leu  Ile  Ser  Asn
945                 950                 955                 960

Asp  Arg  Ser  Trp  Lys  Arg  Asn  Lys  Phe  Arg  Leu  Thr  Tyr  Val  Ala  Glu
                    965                 970                 975

Ala  Pro  Asp  Leu  Thr  Gln  Gly  Leu  Ser  Asn  Val  His  Lys  Lys  Arg  Val
               980                 985                 990

Ser  Ala  Ala  Arg  Leu  Leu  Ser  Arg  Gln  Asn  Leu  Gln  Ser  Pro  Lys  Phe
          995                 1000                1005

Ser  Arg  Ser  Thr  Ile  Phe  Val  Arg  Leu  His  Thr  Asn  Gly  Asn  Gln  Glu
     1010                1015                1020

Leu  Gln  Tyr  Gln  Pro  Gly  Asp  His  Leu  Gly  Val  Phe  Pro  Gly  Asn  His
1025                1030                1035                1040

Glu  Asp  Leu  Val  Asn  Ala  Leu  Ile  Glu  Arg  Leu  Glu  Asp  Ala  Pro  Pro
                    1045                1050                1055

Ala  Asn  His  Val  Val  Lys  Val  Glu  Met  Leu  Glu  Glu  Arg  Asn  Thr  Ala
               1060                1065                1070

Leu  Gly  Val  Ile  Ser  Asn  Trp  Lys  Asp  Glu  Ser  Arg  Leu  Pro  Pro  Cys
          1075                1080                1085

Thr  Ile  Phe  Gln  Ala  Phe  Lys  Tyr  Tyr  Leu  Asp  Ile  Thr  Thr  Pro  Pro
     1090                1095                1100

Thr  Pro  Leu  Gln  Leu  Gln  Gln  Phe  Ala  Ser  Leu  Ala  Thr  Asn  Glu  Lys
1105                1110                1115                1120

Glu  Lys  Gln  Arg  Leu  Leu  Val  Leu  Ser  Lys  Gly  Leu  Gln  Glu  Tyr  Glu
                    1125                1130                1135
```

```
Glu Trp Lys Trp Gly Lys Asn Pro Thr Met Val Glu Val Leu Glu Glu
            1140            1145              1150

Phe Pro Ser Ile Gln Met Pro Ala Thr Leu Leu Leu Thr Gln Leu Ser
            1155            1160              1165

Leu Leu Gln Pro Arg Tyr Tyr Ser Ile Ser Ser Ser Pro Asp Met Tyr
1170                1175                1180

Pro Asp Glu Val His Leu Thr Val Ala Ile Val Ser Tyr His Thr Arg
1185                1190                1195                1200

Asp Gly Glu Gly Pro Val His His Gly Val Cys Ser Ser Trp Leu Asn
            1205            1210              1215

Arg Ile Gln Ala Asp Asp Val Val Pro Cys Phe Val Arg Gly Ala Pro
            1220            1225              1230

Ser Phe His Leu Pro Arg Asn Pro Gln Val Pro Cys Ile Leu Val Gly
            1235            1240              1245

Pro Gly Thr Gly Ile Ala Pro Phe Arg Ser Phe Trp Gln Gln Arg Gln
            1250            1255              1260

Phe Asp Ile Gln His Lys Gly Met Asn Pro Cys Pro Met Val Leu Val
1265                1270                1275                1280

Phe Gly Cys Arg Gln Ser Lys Ile Asp His Ile Tyr Arg Glu Glu Thr
                1285                1290              1295

Leu Gln Ala Lys Asn Lys Gly Val Phe Arg Glu Leu Tyr Thr Ala Tyr
            1300                1305              1310

Ser Arg Glu Pro Asp Arg Pro Lys Lys Tyr Val Gln Asp Val Leu Gln
            1315                1320              1325

Glu Gln Leu Ala Glu Ser Val Tyr Arg Ala Leu Lys Glu Gln Gly Gly
            1330            1335              1340

His Ile Tyr Val Cys Gly Asp Val Thr Met Ala Ala Asp Val Leu Lys
1345                1350                1355                1360

Ala Ile Gln Arg Ile Met Thr Gln Gln Gly Lys Leu Ser Glu Glu Asp
                1365            1370              1375

Ala Gly Val Phe Ile Ser Arg Leu Arg Asp Asp Asn Arg Tyr His Glu
                1380            1385              1390

Asp Ile Phe Gly Val Thr Leu Arg Thr Tyr Glu Val Thr Asn Arg Leu
            1395            1400              1405

Arg Ser Glu Ser Ile Ala Phe Ile Glu Glu Ser Lys Lys Asp Ala Asp
            1410            1415              1420

Glu Val Phe Ser Ser
1425
```

( 2 ) INFORMATION FOR SEQ ID NO:14:

( i ) SEQUENCE CHARACTERISTICS:
        ( A ) LENGTH: 5086 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
        ( C ) INDIVIDUAL ISOLATE: human bcl-2 cDNA ( i x ) FEATURE:
        ( A ) NAME/KEY: CDS
        ( B ) LOCATION: 1459..2178

( x i ) SEQUENCE DESCRIPTION: SEQ ID NO:14:

| | | | | | |
|---|---|---|---|---|---|
| GCGCCCGCCC | CTCCGCGCCG | CCTGCCCGCC | CGCCCGCCGC | GCTCCCGCCC | GCCGCTCTCC | 60 |
| GTGGCCCCGC | CGCGCTGCCG | CCGCCGCCGC | TGCCAGCGAA | GGTGCCGGGG | CTCCGGGCCC | 120 |
| TCCCTGCCGG | CGGCCGTCAG | CGCTCGGAGC | GAACTGCGCG | ACGGGAGGTC | CGGGAGGCGA | 180 |
| CCGTAGTCGC | GCCGCCGCGC | AGGACCAGGA | GGAGGAGAAA | GGGTGCGCAG | CCCGGAGGCG | 240 |
| GGGTGCGCCG | GTGGGGTGCA | GCGGAAGAGG | GGGTCCAGGG | GGGAGAACTT | CGTAGCAGTC | 300 |
| ATCCTTTTTA | GGAAAAGAGG | GAAAAAATAA | AACCCTCCCC | CACCACCTCC | TTCTCCCCAC | 360 |
| CCCTCGCCGC | ACCACACACA | GCGCGGGCTT | CTAGCGCTCG | GCACCGGCGG | GCCAGGCGCG | 420 |
| TCCTGCCTTC | ATTTATCCAG | CAGCTTTTCG | GAAAATGCAT | TTGCTGTTCG | GAGTTTAATC | 480 |
| AGAAGACGAT | TCCTGCCTCC | GTCCCGGCT | CCTTCATCGT | CCCATCTCCC | CTGTCTCTCT | 540 |
| CCTGGGGAGG | CGTGAAGCGG | TCCCGTGGAT | AGAGATTCAT | GCCTGTGTCC | GCGCGTGTGT | 600 |
| GCGCGCGTAT | AAATTGCCGA | GAAGGGGAAA | ACATCACAGG | ACTTCTGCGA | ATACCGGACT | 660 |
| GAAAATTGTA | ATTCATCTGC | CGCCGCCGCT | GCCAAAAAAA | AACTCGAGCT | CTTGAGATCT | 720 |
| CCGGTTGGGA | TTCCTGCGGA | TTGACATTTC | TGTGAAGCAG | AAGTCTGGGA | ATCGATCTGG | 780 |
| AAATCCTCCT | AATTTTTACT | CCCTCTCCCC | CCGACTCCTG | ATTCATTGGG | AAGTTTCAAA | 840 |
| TCAGCTATAA | CTGGAGAGTG | CTGAAGATTG | ATGGGATCGT | TGCCTTATGC | ATTTGTTTTG | 900 |
| GTTTTACAAA | AAGGAAACTT | GACAGAGGAT | CATGCTGTAC | TTAAAAAATA | CAAGTAAGTC | 960 |
| TCGCACAGGA | AATTGGTTTA | ATGTAACTTT | CAATGGAAAC | CTTTGAGATT | TTTTACTTAA | 1020 |
| AGTGCATTCG | AGTAAATTTA | ATTTCCAGGC | AGCTTAATAC | ATTGTTTTA | GCCGTGTTAC | 1080 |
| TTGTAGTGTG | TATGCCCTGC | TTTCACTCAG | TGTGTACAGG | GAAACGCACC | TGATTTTTA | 1140 |
| CTTATTAGTT | TGTTTTTTCT | TTAACCTTTC | AGCATCACAG | AGGAAGTAGA | CTGATATTAA | 1200 |
| CAATACTTAC | TAATAATAAC | GTGCCTCATG | AAATAAAGAT | CCGAAAGGAA | TTGGAATAAA | 1260 |
| AATTTCCTGC | GTCTCATGCC | AAGAGGGAAA | CACCAGAATC | AAGTGTTCCG | CGTGATTGAA | 1320 |
| GACACCCCCT | CGTCCAAGAA | TGCAAAGCAC | ATCCAATAAA | ATAGCTGGAT | TATAACTCCT | 1380 |
| CTTCTTTCTC | TGGGGGCCGT | GGGGTGGGAG | CTGGGGCGAG | AGGTGCCGTT | GGCCCCCGTT | 1440 |

| | | | | | |
|---|---|---|---|---|---|
| GCTTTTCCTC | TGGGAAGG | ATG GCG CAC GCT GGG AGA ACG GGG TAC GAC AAC | 1491 |
| | | Met Ala His Ala Gly Arg Thr Gly Tyr Asp Asn | |
| | | 1       5             10 | |

| CGG GAG ATA GTG ATG AAG TAC ATC CAT TAT AAG CTG TCG CAG AGG GGC | 1539 |
|---|---|
| Arg Glu Ile Val Met Lys Tyr Ile His Tyr Lys Leu Ser Gln Arg Gly | |
| 15                  20                    25 | |

| TAC GAG TGG GAT GCG GGA GAT GTG GGC GCC GCG CCC CCG GGG GCC GCC | 1587 |
|---|---|
| Tyr Glu Trp Asp Ala Gly Asp Val Gly Ala Ala Pro Pro Gly Ala Ala | |
| 30                  35                    40 | |

| CCC GCA CCG GGC ATC TTC TCC TCC CAG CCC GGG CAC ACG CCC CAT CCA | 1635 |
|---|---|
| Pro Ala Pro Gly Ile Phe Ser Ser Gln Pro Gly His Thr Pro His Pro | |
| 45                  50                    55 | |

| GCC GCA TCC CGC GAC CCG GTC GCC AGG ACC TCG CCG CTG CAG ACC CCG | 1683 |
|---|---|
| Ala Ala Ser Arg Asp Pro Val Ala Arg Thr Ser Pro Leu Gln Thr Pro | |
| 60                  65                    70                 75 | |

| GCT GCC CCC GGC GCC GCC GCG GGG CCT GCG CTC AGC CCG GTG CCA CCT | 1731 |
|---|---|
| Ala Ala Pro Gly Ala Ala Ala Gly Pro Ala Leu Ser Pro Val Pro Pro | |
| 80                  85                    90 | |

| GTG GTC CAC CTG GCC CTC CGC CAA GCC GGC GAC GAC TTC TCC CGC CGC | 1779 |
|---|---|
| Val Val His Leu Ala Leu Arg Gln Ala Gly Asp Asp Phe Ser Arg Arg | |
| 95                  100                   105 | |

| TAC CGC GGC GAC TTC GCC GAG ATG TCC AGC CAG CTG CAC CTG ACG CCC | 1827 |
|---|---|
| Tyr Arg Gly Asp Phe Ala Glu Met Ser Ser Gln Leu His Leu Thr Pro | |

-continued

```
           110                          115                         120
TTC ACC GCG CGG GGA CGC TTT GCC ACG GTG GTG GAG GAG CTC TTC AGG          1875
Phe Thr Ala Arg Gly Arg Phe Ala Thr Val Val Glu Glu Leu Phe Arg
    125                 130                 135

GAC GGG GTG AAC TGG GGG AGG ATT GTG GCC TTT GAG TTC GGT GGG              1923
Asp Gly Val Asn Trp Gly Arg Ile Val Ala Phe Glu Phe Gly Gly
140                 145                 150                 155

GTC ATG TGT GTG GAG AGC GTC AAC CGG GAG ATG TCG CCC CTG GTG GAC          1971
Val Met Cys Val Glu Ser Val Asn Arg Glu Met Ser Pro Leu Val Asp
                    160                 165                 170

AAC ATC GCC CTG TGG ATG ACT GAG TAC CTG AAC CGG CAC CTG CAC ACC          2019
Asn Ile Ala Leu Trp Met Thr Glu Tyr Leu Asn Arg His Leu His Thr
                175                 180                 185

TGG ATC CAG GAT AAC GGA GGC TGG GAT GCC TTT GTG GAA CTG TAC GGC          2067
Trp Ile Gln Asp Asn Gly Gly Trp Asp Ala Phe Val Glu Leu Tyr Gly
            190                 195                 200

CCC AGC ATG CGG CCT CTG TTT GAT TTC TCC TGG CTG TCT CTG AAG ACT          2115
Pro Ser Met Arg Pro Leu Phe Asp Phe Ser Trp Leu Ser Leu Lys Thr
    205                 210                 215

CTG CTC AGT TTG GCC CTG GTG GGA GCT TGC ATC ACC CTG GGT GCC TAT          2163
Leu Leu Ser Leu Ala Leu Val Gly Ala Cys Ile Thr Leu Gly Ala Tyr
220                 225                 230                 235

CTG AGC CAC AAG TGAAGTCAAC ATGCCTGCCC CAAACAAATA TGCAAAAGGT              2215
Leu Ser His Lys
                240

TCACTAAAGC AGTAGAAATA ATATGCATTG TCAGTGATGT ACCATGAAAC AAAGCTGCAG        2275

GCTGTTTAAG AAAAAATAAC ACACATATAA ACATCACACA CACAGACAGA CACACACACA        2335

CACAACAATT AACAGTCTTC AGGCAAAACG TCGAATCAGC TATTTACTGC CAAAGGGAAA        2395

TATCATTTAT TTTTTACATT ATTAAGAAAA AAGATTTATT TATTTAAGAC AGTCCCATCA        2455

AAACTCCGTC TTTGGAAATC CGACCACTAA TTGCCAAACA CCGCTTCGTG TGGCTCCACC        2515

TGGATGTTCT GTGCCTGTAA ACATAGATTC GCTTTCCATG TTGTTGGCCG GATCACCATC        2575

TGAAGAGCAG ACGGATGGAA AAAGGACCTG ATCATTGGGG AAGCTGGCTT TCTGGCTGCT        2635

GGAGGCTGGG GAGAAGGTGT TCATTCACTT GCATTTCTTT GCCCTGGGGG CGTGATATTA        2695

ACAGAGGGAG GGTTCCCGTG GGGGGAAGTC CATGCCTCCC TGGCCTGAAG AAGAGACTCT        2755

TTGCATATGA CTCACATGAT GCATACCTGG TGGGAGGAAA AGAGTTGGGA ACTTCAGATG        2815

GACCTAGTAC CCACTGAGAT TTCCACGCCG AAGGACAGCG ATGGGAAAAA TGCCCTTAAA        2875

TCATAGGAAA GTATTTTTTT AAGCTACCAA TTGTGCCGAG AAAAGCATTT TAGCAATTTA        2935

TACAATATCA TCCAGTACCT TAAACCCTGA TTGTGTATAT TCATATATTT TGGATACGCA        2995

CCCCCCAACT CCCAATACTG GCTCTGTCTG AGTAAGAAAC AGAATCCTCT GGAACTTGAG        3055

GAAGTGAACA TTTCGGTGAC TTCCGATCAG GAAGGCTAGA GTTACCCAGA GCATCAGGCC        3115

GCCACAAGTG CCTGCTTTTA GGAGACCGAA GTCCGCAGAA CCTACCTGTG TCCCAGCTTG        3175

GAGGCCTGGT CCTGGAACTG AGCCGGGCCC TCACTGGCCT CCTCCAGGGA TGATCAACAG        3235

GGTAGTGTGG TCTCCGAATG TCTGGAAGCT GATGGATGGA GCTCAGAATT CCACTGTCAA        3295

GAAAGAGCAG TAGAGGGGTG TGGCTGGGCC TGTCACCCTG GGGCCCTCCA GGTAGGCCCG        3355

TTTTCACGTG GAGCATAGGA GCCACGACCC TTCTTAAGAC ATGTATCACT GTAGAGGGAA        3415

GGAACAGAGG CCCTGGGCCT TCCTATCAGA AGGACATGGT GAAGGCTGGG AACGTGAGGA        3475

GAGGCAATGG CCACGGCCCA TTTTGGCTGT AGCACATGGC ACGTTGGCTG TGTGGCCTTG        3535

GCCACCTGTG AGTTTAAAGC AAGGCTTTAA ATGACTTTGG AGAGGGTCAC AAATCCTAAA        3595
```

| | | | | | |
|---|---|---|---|---|---|
| AGAAGCATTG | AAGTGAGGTG | TCATGGATTA | ATTGACCCCT | GTCTATGGAA | TTACATGTAA | 3655 |
| AACATTATCT | TGTCACTGTA | GTTTGGTTTT | ATTTGAAAAC | CTGACAAAAA | AAAAGTTCCA | 3715 |
| GGTGTGGAAT | ATGGGGGTTA | TCTGTACATC | CTGGGGCATT | AAAAAAAAAT | CAATGGTGGG | 3775 |
| GAACTATAAA | GAAGTAACAA | AAGAAGTGAC | ATCTTCAGCA | AATAAACTAG | GAAATTTTTT | 3835 |
| TTTCTTCCAG | TTAGAATCA | GCCTTGAAAC | ATTGATGGAA | TAACTCTGTG | GCATTATTGC | 3895 |
| ATTATATACC | ATTTATCTGT | ATTAACTTTG | GAATGTACTC | TGTTCAATGT | TTAATGCTGT | 3955 |
| GGTTGATATT | TCGAAAGCTG | CTTTAAAAAA | ATACATGCAT | CTCAGCGTTT | TTTTGTTTTT | 4015 |
| AATTGTATTT | AGTTATGGCC | TATACACTAT | TTGTGAGCAA | AGGTGATCGT | TTTCTGTTTG | 4075 |
| AGATTTTTAT | CTCTTGATTC | TTCAAAAGCA | TTCTGAGAAG | GTGAGATAAG | CCCTGAGTCT | 4135 |
| CAGCTACCTA | AGAAAAACCT | GGATGTCACT | GGCCACTGAG | GAGCTTTGTT | TCAACCAAGT | 4195 |
| CATGTGCATT | TCCACGTCAA | CAGAATTGTT | TATTGTGACA | GTTATATCTG | TTGTCCCTTT | 4255 |
| GACCTTGTTT | CTTGAAGGTT | TCCTCGTCCC | TGGGCAATTC | CGCATTTAAT | TCATGGTATT | 4315 |
| CAGGATTACA | TGCATGTTTG | GTTAAACCCA | TGAGATTCAT | TCAGTTAAAA | ATCCAGATGG | 4375 |
| CGAATGACCA | GCAGATTCAA | ATCTATGGTG | GTTTGACCTT | TAGAGAGTTG | CTTTACGTGG | 4435 |
| CCTGTTTCAA | CACAGACCCA | CCCAGAGCCC | TCCTGCCCTC | CTTCCGCGGG | GGCTTTCTCA | 4495 |
| TGGCTGTCCT | TCAGGGTCTT | CCTGAAATGC | AGTGGTCGTT | ACGCTCCACC | AAGAAAGCAG | 4555 |
| GAAACCTGTG | GTATGAAGCC | AGACCTCCCC | GGCGGGCCTC | AGGGAACAGA | ATGATCAGAC | 4615 |
| CTTTGAATGA | TTCTAATTTT | TAAGCAAAAT | ATTATTTTAT | GAAAGGTTTA | CATTGTCAAA | 4675 |
| GTGATGAATA | TGGAATATCC | AATCCTGTGC | TGCTATCCTG | CCAAAATCAT | TTTAATGGAG | 4735 |
| TCAGTTTGCA | GTATGCTCCA | CGTGGTAAGA | TCCTCCAAGC | TGCTTTAGAA | GTAACAATGA | 4795 |
| AGAACGTGGA | CGTTTTTAAT | ATAAAGCCTG | TTTTGTCTTT | TGTTGTTGTT | CAAACGGGAT | 4855 |
| TCACAGAGTA | TTTGAAAAAT | GTATATATAT | TAAGAGGTCA | CGGGGGCTAA | TTGCTAGCTG | 4915 |
| GCTGCCTTTT | GCTGTGGGGT | TTTGTTACCT | GGTTTTAATA | ACAGTAAATG | TGCCCAGCCT | 4975 |
| CTTGGCCCCA | GAACTGTACA | GTATTGTGGC | TGCACTTGCT | CTAAGAGTAG | TTGATGTTGC | 5035 |
| ATTTTCCTTA | TTGTTAAAAA | CATGTTAGAA | GCAATGAATG | TATATAAAAG | C | 5086 |

( 2 ) INFORMATION FOR SEQ ID NO:15:

( i ) SEQUENCE CHARACTERISTICS:
        ( A ) LENGTH: 239 amino acids
        ( B ) TYPE: amino acid
        ( D ) TOPOLOGY: linear ( i i ) MOLECULE TYPE: protein ( x i ) SEQUENCE DESCRIPTION: SEQ ID NO:15:

```
Met Ala His Ala Gly Arg Thr Gly Tyr Asp Asn Arg Glu Ile Val Met
 1               5                  10                  15

Lys Tyr Ile His Tyr Lys Leu Ser Gln Arg Gly Tyr Glu Trp Asp Ala
             20                  25                  30

Gly Asp Val Gly Ala Ala Pro Pro Gly Ala Ala Pro Ala Pro Gly Ile
         35                  40                  45

Phe Ser Ser Gln Pro Gly His Thr His Pro Ala Ala Ser Arg Asp
     50                  55                  60

Pro Val Ala Arg Thr Ser Pro Leu Gln Thr Pro Ala Ala Pro Gly Ala
 65                  70                  75                  80

Ala Ala Gly Pro Ala Leu Ser Pro Val Pro Pro Val Val His Leu Ala
                 85                  90                  95
```

| Leu | Arg | Gln | Ala<br>100 | Gly | Asp | Asp | Phe | Ser<br>105 | Arg | Arg | Tyr | Arg | Gly<br>110 | Asp | Phe |
| --- | --- | --- | --- | --- | --- | --- | --- | --- | --- | --- | --- | --- | --- | --- | --- |
| Ala | Glu | Met<br>115 | Ser | Ser | Gln | Leu | His<br>120 | Leu | Thr | Pro | Phe | Thr<br>125 | Ala | Arg | Gly |
| Arg | Phe<br>130 | Ala | Thr | Val | Val | Glu<br>135 | Glu | Leu | Phe | Arg | Asp<br>140 | Gly | Val | Asn | Trp |
| Gly<br>145 | Arg | Ile | Val | Ala | Phe<br>150 | Phe | Glu | Phe | Gly | Gly<br>155 | Val | Met | Cys | Val | Glu<br>160 |
| Ser | Val | Asn | Arg | Glu<br>165 | Met | Ser | Pro | Leu | Val<br>170 | Asp | Asn | Ile | Ala | Leu<br>175 | Trp |
| Met | Thr | Glu | Tyr<br>180 | Leu | Asn | Arg | His | Leu<br>185 | His | Thr | Trp | Ile | Gln<br>190 | Asp | Asn |
| Gly | Gly | Trp<br>195 | Asp | Ala | Phe | Val | Glu<br>200 | Leu | Tyr | Gly | Pro | Ser<br>205 | Met | Arg | Pro |
| Leu | Phe | Asp<br>210 | Phe | Ser | Trp | Leu | Ser<br>215 | Leu | Lys | Thr | Leu<br>220 | Leu | Ser | Leu | Ala |
| Leu<br>225 | Val | Gly | Ala | Cys | Ile<br>230 | Thr | Leu | Gly | Ala | Tyr<br>235 | Leu | Ser | His | Lys | |

( 2 ) INFORMATION FOR SEQ ID NO:16:

( i ) SEQUENCE CHARACTERISTICS:
        ( A ) LENGTH: 1846 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
        ( C ) INDIVIDUAL ISOLATE: bcl-2 fusion gene; Seto, et al.,
            EMBO J 7:123 (1988)

( i x ) FEATURE:
        ( A ) NAME/KEY: CDS
        ( B ) LOCATION: 887..1606

( x i ) SEQUENCE DESCRIPTION: SEQ ID NO:16:

```
ACCACCTCCT TCTCCCCACC CCTCGCCGCA CCACACACAG CGCGGGCTTC TGGCGCTCGG      60
CACCGGCGGG CCAGGCGCGT CCTGTCTTCA TTTATCCAGC AGCTTTTCGG AAAATCCATT     120
TGGTGTTCGG AGTTTAATCA GAAGAGGATT CCTGCCTCCG TCCCCGGCTC CTTCATCGTC     180
CCCTCTCCCC TGTCTCTCTC CTGGGGAGGC GTGAAGAGAG ATTCATGCCT GTGCCCGCGC     240
GTGTGTGCGC GCGTATAAAT TGCCGAGAAG GGGAAAACAT CACAGGACTT CTGCGAATAC     300
CGGACTGAAA ATTGTAGCTC ATCTGCCGCC GCCGCTGCCT TTTTTTTTTC TCGAGCTCTT     360
GAGATCTCCG GTTGGGACTC CTGCGGATTG ACATTTCTGT GAAGCAGAAG TCTGGGAATC     420
GATCTGGAAA TCCTCCTAAT TTTTACTCCC TCTCCCCCCG ACTCCTGATT CATTGGGAAG     480
TTTCAAATCA GCTATAACTG GAGAGAGCTG AAGATTGATG GGATCGTTGC CTTATGCCTT     540
TGTTTTGGTT TTACAAAAAG GAAACTTGAC AGAGGATCAT GCTATACTTA AAAAATACAA     600
CATCGCAGAG GAAGTAGACT CATATTAAAA ATACTTACTA ATAATAACGT GCCTCATGAA     660
GTAAAGATCC GAAAGGAATT GGAATAAAAC TTTCCTGCAT CTCAAGCCAA GGGGAAACA      720
CCAGAATCAA GTGTTCCGCG TGATTGAAGA CACCCCCTCG TCCAAGAATG CAAAGCACAT     780
CCAATAAAAG AGCTGGATTA TAACTCCTCT TCTTTCTCTG GGGCCGTGG  GGTAGGGGCT     840
```

| | | | | | | | | | | | | | | | | |
|---|---|---|---|---|---|---|---|---|---|---|---|---|---|---|---|---|
| GGGGCGAGAG | | GTGCCGTTGG | | CCCCCGTTGC | | TTTTCCTCTG | | GGAGGG | ATG<br>Met<br>1 | | GCG<br>Ala | | CAC<br>His | | | 895 |

| | | | | | | | | | | | | | | | |
|---|---|---|---|---|---|---|---|---|---|---|---|---|---|---|---|
| GCT<br>Ala | GGG<br>Gly<br>5 | AGA<br>Arg | AGT<br>Ser | GGT<br>Gly | TAC<br>Tyr | GAT<br>Asp | AAC<br>Asn<br>10 | CGG<br>Arg | GAG<br>Glu | ATA<br>Ile | GTG<br>Val<br>15 | ATG<br>Met | AAG<br>Lys | TAC<br>Tyr | ATC<br>Ile | 943 |
| CAT<br>His<br>20 | TAT<br>Tyr | AAG<br>Lys | CTG<br>Leu | TCG<br>Ser | CAG<br>Gln<br>25 | AGG<br>Arg | GGC<br>Gly | TAC<br>Tyr | GAG<br>Glu | TGG<br>Trp<br>30 | GAT<br>Asp | GCG<br>Ala | GGA<br>Gly | GAT<br>Asp | GTG<br>Val<br>35 | 991 |
| GGC<br>Gly | GCC<br>Ala | GCG<br>Ala | CCC<br>Pro | CCG<br>Pro<br>40 | GGG<br>Gly | GCC<br>Ala | GCC<br>Ala | CCC<br>Pro | GCA<br>Ala<br>45 | CCG<br>Pro | GGC<br>Gly | TTC<br>Phe | TTC<br>Phe | TCC<br>Ser<br>50 | TCC<br>Ser | 1039 |
| CAG<br>Gln | CCC<br>Pro | GGG<br>Gly | CAC<br>His<br>55 | ACG<br>Thr | CCC<br>Pro | CAT<br>His | CCA<br>Pro | GCC<br>Ala<br>60 | GCA<br>Ala | TCC<br>Ser | CGG<br>Arg | GAC<br>Asp | CCG<br>Pro<br>65 | GTC<br>Val | GCC<br>Ala | 1087 |
| AGG<br>Arg | ACC<br>Thr | TCG<br>Ser<br>70 | CCA<br>Pro | CTA<br>Leu | CAG<br>Gln | ACC<br>Thr | CCG<br>Pro<br>75 | GCT<br>Ala | GCC<br>Ala | CCC<br>Pro | GGC<br>Gly | GCC<br>Ala<br>80 | GCC<br>Ala | GCG<br>Ala | GGG<br>Gly | 1135 |
| CCT<br>Pro | GCG<br>Ala<br>85 | CTC<br>Leu | AGC<br>Ser | CCG<br>Pro | GTG<br>Val | CCA<br>Pro<br>90 | CCT<br>Pro | GTG<br>Val | GTC<br>Val | CAC<br>His | CTG<br>Leu<br>95 | ACC<br>Thr | CTC<br>Leu | CGC<br>Arg | CAG<br>Gln | 1183 |
| GCC<br>Ala | GGC<br>Gly | GAC<br>Asp | GAC<br>Asp | TTC<br>Phe<br>105 | TCC<br>Ser | CGC<br>Arg | CGC<br>Arg | TAC<br>Tyr | CGC<br>Arg<br>110 | CGC<br>Arg | GAC<br>Asp | TTC<br>Phe | GCC<br>Ala | GAG<br>Glu<br>115 | ATG<br>Met | 1231 |
| TCC<br>Ser<br>100 | AGC<br>Ser | CAG<br>Gln | CTG<br>Leu | CAC<br>His<br>120 | CTG<br>Leu | ACG<br>Thr | CCC<br>Pro | TTC<br>Phe | ACC<br>Thr<br>125 | GCG<br>Ala | CGG<br>Arg | GGA<br>Gly | TGC<br>Cys | TTT<br>Phe<br>130 | GCC<br>Ala | 1279 |
| ACG<br>Thr | GTG<br>Val | GTG<br>Val | GAG<br>Glu<br>135 | GAG<br>Glu | CTC<br>Leu | TTC<br>Phe | AGG<br>Arg | GAC<br>Asp<br>140 | GGG<br>Gly | GTG<br>Val | AAC<br>Asn | TGG<br>Trp | GGG<br>Gly<br>145 | AGG<br>Arg | ATT<br>Ile | 1327 |
| GTG<br>Val | GCC<br>Ala | TTC<br>Phe<br>150 | TTT<br>Phe | GAG<br>Glu | TTC<br>Phe | GGT<br>Gly | GGG<br>Gly<br>155 | GTC<br>Val | ATG<br>Met | TGT<br>Cys | GTG<br>Val | GAG<br>Glu<br>160 | AGC<br>Ser | GTC<br>Val | AAC<br>Asn | 1375 |
| CGG<br>Arg | GAG<br>Glu<br>165 | ATG<br>Met | TCG<br>Ser | CCC<br>Pro | CTG<br>Leu | GTG<br>Val<br>170 | GAC<br>Asp | AAC<br>Asn | ATC<br>Ile | GCC<br>Ala | CTG<br>Leu<br>175 | TGG<br>Trp | ATG<br>Met | ACT<br>Thr | GAG<br>Glu | 1423 |
| TAC<br>Tyr<br>180 | CTG<br>Leu | AAC<br>Asn | CGG<br>Arg | CAC<br>His | CTG<br>Leu<br>185 | CAC<br>His | ACC<br>Thr | TGG<br>Trp | ATC<br>Ile | CAG<br>Gln<br>190 | GAT<br>Asp | AAC<br>Asn | GGA<br>Gly | GGC<br>Gly | TGG<br>Trp<br>195 | 1471 |
| GAT<br>Asp | GCC<br>Ala | TTT<br>Phe | GTG<br>Val | GAA<br>Glu<br>200 | CTG<br>Leu | TAC<br>Tyr | GGC<br>Gly | CCC<br>Pro | AGC<br>Ser<br>205 | ATG<br>Met | CGG<br>Arg | CCT<br>Pro | CTG<br>Leu | TTT<br>Phe<br>210 | GAT<br>Asp | 1519 |
| TTC<br>Phe | TCC<br>Ser | TGG<br>Trp | CTG<br>Leu<br>215 | TCT<br>Ser | CTG<br>Leu | AAG<br>Lys | ACT<br>Thr | CTG<br>Leu<br>220 | CTC<br>Leu | AGT<br>Ser | TTG<br>Leu | GCC<br>Ala | CTG<br>Leu<br>225 | GTG<br>Val | GGA<br>Gly | 1567 |
| GCT<br>Ala | TGC<br>Cys | ATC<br>Ile<br>230 | ACC<br>Thr | CTG<br>Leu | GGT<br>Gly | GCC<br>Ala | TAT<br>Tyr<br>235 | CTG<br>Leu | GGC<br>Gly | CAC<br>His | AAG<br>Lys | TGAAGTCAAC<br>240 | | | | 1613 |

| | | | | |
|---|---|---|---|---|
| ATGCCTGCCC | CAAACAAATA | TGCAAAAGGT | TCACTAAAGC | AGTAGAAATA ATATGCATTG | 1673 |
| TCAGTGATGT | ACCATGAAAC | AAAGCTGCAG | GCTGTTTAAG | AAAAAATAAC ACACATATAA | 1733 |
| ACATCACACA | CACAGACAGA | CACACACACA | CACAACAATT | AACAGTCTTC AGGCAAAACG | 1793 |
| TCGAATCAGC | TATTTACTGC | CAAAGGGAAA | TATCATTTAT | TTTTTACATT ATT | 1846 |

( 2 ) INFORMATION FOR SEQ ID NO:17:

( i ) SEQUENCE CHARACTERISTICS:
        ( A ) LENGTH: 239 amino acids
        ( B ) TYPE: amino acid
        ( D ) TOPOLOGY: linear ( i i ) MOLECULE TYPE: protein ( x i ) SEQUENCE DESCRIPTION: SEQ ID NO:17:

| Met | Ala | His | Ala | Gly | Arg | Ser | Gly | Tyr | Asp | Asn | Arg | Glu | Ile | Val | Met |
|---|---|---|---|---|---|---|---|---|---|---|---|---|---|---|---|
| 1 | | | | 5 | | | | | 10 | | | | | 15 | |

| Lys | Tyr | Ile | His | Tyr | Lys | Leu | Ser | Gln | Arg | Gly | Tyr | Glu | Trp | Asp | Ala |
|---|---|---|---|---|---|---|---|---|---|---|---|---|---|---|---|
| | | | 20 | | | | | 25 | | | | | 30 | | |

| Gly | Asp | Val | Gly | Ala | Ala | Pro | Pro | Gly | Ala | Ala | Pro | Ala | Pro | Gly | Phe |
|---|---|---|---|---|---|---|---|---|---|---|---|---|---|---|---|
| | | 35 | | | | | 40 | | | | | 45 | | | |

| Phe | Ser | Ser | Gln | Pro | Gly | His | Thr | Pro | His | Pro | Ala | Ala | Ser | Arg | Asp |
|---|---|---|---|---|---|---|---|---|---|---|---|---|---|---|---|
| | 50 | | | | | 55 | | | | | 60 | | | | |

| Pro | Val | Ala | Arg | Thr | Ser | Pro | Leu | Gln | Thr | Pro | Ala | Ala | Pro | Gly | Ala |
|---|---|---|---|---|---|---|---|---|---|---|---|---|---|---|---|
| 65 | | | | | 70 | | | | | 75 | | | | | 80 |

| Ala | Ala | Gly | Pro | Ala | Leu | Ser | Pro | Val | Pro | Pro | Val | Val | His | Leu | Thr |
|---|---|---|---|---|---|---|---|---|---|---|---|---|---|---|---|
| | | | | 85 | | | | | 90 | | | | | 95 | |

| Leu | Arg | Gln | Ala | Gly | Asp | Asp | Phe | Ser | Arg | Arg | Tyr | Arg | Arg | Asp | Phe |
|---|---|---|---|---|---|---|---|---|---|---|---|---|---|---|---|
| | | | | 100 | | | | | 105 | | | | | 110 | |

| Ala | Glu | Met | Ser | Ser | Gln | Leu | His | Leu | Thr | Pro | Phe | Thr | Ala | Arg | Gly |
|---|---|---|---|---|---|---|---|---|---|---|---|---|---|---|---|
| | | | 115 | | | | | 120 | | | | | 125 | | |

| Cys | Phe | Ala | Thr | Val | Val | Glu | Glu | Leu | Phe | Arg | Asp | Gly | Val | Asn | Trp |
|---|---|---|---|---|---|---|---|---|---|---|---|---|---|---|---|
| | 130 | | | | | 135 | | | | | 140 | | | | |

| Gly | Arg | Ile | Val | Ala | Phe | Phe | Glu | Phe | Gly | Gly | Val | Met | Cys | Val | Glu |
|---|---|---|---|---|---|---|---|---|---|---|---|---|---|---|---|
| 145 | | | | | 150 | | | | | 155 | | | | | 160 |

| Ser | Val | Asn | Arg | Glu | Met | Ser | Pro | Leu | Val | Asp | Asn | Ile | Ala | Leu | Trp |
|---|---|---|---|---|---|---|---|---|---|---|---|---|---|---|---|
| | | | | 165 | | | | | 170 | | | | | 175 | |

| Met | Thr | Glu | Tyr | Leu | Asn | Arg | His | Leu | His | Thr | Trp | Ile | Gln | Asp | Asn |
|---|---|---|---|---|---|---|---|---|---|---|---|---|---|---|---|
| | | | 180 | | | | | 185 | | | | | 190 | | |

| Gly | Gly | Trp | Asp | Ala | Phe | Val | Glu | Leu | Tyr | Gly | Pro | Ser | Met | Arg | Pro |
|---|---|---|---|---|---|---|---|---|---|---|---|---|---|---|---|
| | | 195 | | | | | 200 | | | | | 205 | | | |

| Leu | Phe | Asp | Phe | Ser | Trp | Leu | Ser | Leu | Lys | Thr | Leu | Leu | Ser | Leu | Ala |
|---|---|---|---|---|---|---|---|---|---|---|---|---|---|---|---|
| | 210 | | | | | 215 | | | | | 220 | | | | |

| Leu | Val | Gly | Ala | Cys | Ile | Thr | Leu | Gly | Ala | Tyr | Leu | Gly | His | Lys |
|---|---|---|---|---|---|---|---|---|---|---|---|---|---|---|
| 225 | | | | | 230 | | | | | 235 | | | | |

( 2 ) INFORMATION FOR SEQ ID NO:18:

( i ) SEQUENCE CHARACTERISTICS:
        ( A ) LENGTH: 4353 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
        ( C ) INDIVIDUAL ISOLATE: Human NOS-1 gene, Fujisawa, et al,
            J. Neurochem 63:140 1994

( i x ) FEATURE:
        ( A ) NAME/KEY: CDS
        ( B ) LOCATION: 1..4305

( x i ) SEQUENCE DESCRIPTION: SEQ ID NO:18:

| ATG | GAG | GAT | CAC | ATG | TTC | GGT | GTT | CAG | CAA | ATC | CAG | CCC | AAT | GTC | ATT | 48 |
|---|---|---|---|---|---|---|---|---|---|---|---|---|---|---|---|---|
| Met | Glu | Asp | His | Met | Phe | Gly | Val | Gln | Gln | Ile | Gln | Pro | Asn | Val | Ile | |
| 1 | | | | 5 | | | | | 10 | | | | | 15 | | |

| TCT | GTT | CGT | CTC | TTC | AAG | CGC | AAA | GTT | GGG | GGC | CTG | GGA | TTT | CTG | GTG | 96 |
|---|---|---|---|---|---|---|---|---|---|---|---|---|---|---|---|---|
| Ser | Val | Arg | Leu | Phe | Lys | Arg | Lys | Val | Gly | Gly | Leu | Gly | Phe | Leu | Val | |

-continued

|  |  | 20 |  |  |  |  | 25 |  |  |  |  | 30 |  |  |  |  |
|---|---|---|---|---|---|---|---|---|---|---|---|---|---|---|---|---|
| AAG<br>Lys | GAG<br>Glu | CGG<br>Arg<br>35 | GTC<br>Val | AGT<br>Ser | AAG<br>Lys | CCG<br>Pro | CCC<br>Pro<br>40 | GTG<br>Val | ATC<br>Ile | ATC<br>Ile | TCT<br>Ser | GAC<br>Asp<br>45 | CTG<br>Leu | ATT<br>Ile | CGT<br>Arg | 144 |
| GGG<br>Gly | GGC<br>Gly<br>50 | GCC<br>Ala | GCA<br>Ala | GAG<br>Glu | CAG<br>Gln | AGT<br>Ser<br>55 | GGC<br>Gly | CTC<br>Leu | ATC<br>Ile | CAG<br>Gln | GCC<br>Ala<br>60 | GGA<br>Gly | GAC<br>Asp | ATC<br>Ile | ATT<br>Ile | 192 |
| CTT<br>Leu<br>65 | GCG<br>Ala | GTC<br>Val | AAC<br>Asn | GGC<br>Gly | CGG<br>Arg<br>70 | CCC<br>Pro | TTG<br>Leu | GTG<br>Val | GAC<br>Asp | CTG<br>Leu<br>75 | AGC<br>Ser | TAT<br>Tyr | GAC<br>Asp | AGC<br>Ser | GCC<br>Ala<br>80 | 240 |
| CTG<br>Leu | GAG<br>Glu | GTA<br>Val | CTC<br>Leu | AGA<br>Arg<br>85 | GGC<br>Gly | ATT<br>Ile | GCC<br>Ala | TCT<br>Ser | GAG<br>Glu<br>90 | ACC<br>Thr | CAC<br>His | GTG<br>Val | GTC<br>Val | CTC<br>Leu<br>95 | ATT<br>Ile | 288 |
| CTG<br>Leu | AGG<br>Arg | GGC<br>Gly | CCT<br>Pro<br>100 | GAA<br>Glu | GGT<br>Gly | TTC<br>Phe | ACC<br>Thr | ACG<br>Thr<br>105 | CAC<br>His | CTG<br>Leu | GAG<br>Glu | ACC<br>Thr | ACC<br>Thr<br>110 | TTT<br>Phe | ACA<br>Thr | 336 |
| GGT<br>Gly | GAT<br>Asp | GGG<br>Gly<br>115 | ACC<br>Thr | CCC<br>Pro | AAG<br>Lys | ACC<br>Thr | ATC<br>Ile<br>120 | CGG<br>Arg | GTG<br>Val | ACA<br>Thr | CAG<br>Gln | CCC<br>Pro<br>125 | CTG<br>Leu | GGT<br>Gly | CCC<br>Pro | 384 |
| CCC<br>Pro | ACC<br>Thr<br>130 | AAA<br>Lys | GCC<br>Ala | GTG<br>Val | GAT<br>Asp | CTG<br>Leu<br>135 | TCC<br>Ser | CAC<br>His | CAG<br>Gln | CCA<br>Pro | CCG<br>Pro<br>140 | GCC<br>Ala | GGC<br>Gly | AAA<br>Lys | GAA<br>Glu | 432 |
| CAG<br>Gln<br>145 | CCC<br>Pro | CTG<br>Leu | GCA<br>Ala | GTG<br>Val | GAT<br>Asp<br>150 | GGG<br>Gly | GCC<br>Ala | TCG<br>Ser | GGT<br>Gly | CCC<br>Pro<br>155 | GGG<br>Gly | AAT<br>Asn | GGG<br>Gly | CCT<br>Pro | CAG<br>Gln<br>160 | 480 |
| CAT<br>His | GCC<br>Ala | TAC<br>Tyr | GAT<br>Asp | GAT<br>Asp<br>165 | GGG<br>Gly | CAG<br>Gln | GAG<br>Glu | GCT<br>Ala | GGC<br>Gly<br>170 | TCA<br>Ser | CTC<br>Leu | CCC<br>Pro | CAT<br>His | GCC<br>Ala<br>175 | AAC<br>Asn | 528 |
| GGC<br>Gly | CTG<br>Leu | GCC<br>Ala | CCC<br>Pro<br>180 | AGG<br>Arg | CCC<br>Pro | CCA<br>Pro | GGC<br>Gly | CAG<br>Gln<br>185 | GAC<br>Asp | CCC<br>Pro | GCG<br>Ala | AAG<br>Lys | AAA<br>Lys<br>190 | GCA<br>Ala | ACC<br>Thr | 576 |
| AGA<br>Arg | GTC<br>Val | AGC<br>Ser<br>195 | CTC<br>Leu | CAA<br>Gln | GGC<br>Gly | AGA<br>Arg | GGG<br>Gly<br>200 | GAG<br>Glu | AAC<br>Asn | AAT<br>Asn | GAA<br>Glu | CTG<br>Leu<br>205 | CTC<br>Leu | AAG<br>Lys | GAG<br>Glu | 624 |
| ATA<br>Ile | GAG<br>Glu<br>210 | CCT<br>Pro | GTG<br>Val | CTG<br>Leu | AGC<br>Ser<br>215 | CTT<br>Leu | CTC<br>Leu | ACC<br>Thr | AGT<br>Ser | GGG<br>Gly<br>220 | AGC<br>Ser | AGA<br>Arg | GGG<br>Gly | GTC<br>Val | AAG<br>Lys | 672 |
| GGA<br>Gly<br>225 | GGG<br>Gly | GCA<br>Ala | CCT<br>Pro | GCC<br>Ala | AAG<br>Lys<br>230 | GCA<br>Ala | GAG<br>Glu | ATG<br>Met | AAA<br>Lys | GAT<br>Asp<br>235 | ATG<br>Met | GGA<br>Gly | ATC<br>Ile | CAG<br>Gln | GTG<br>Val<br>240 | 720 |
| GAC<br>Asp | AGA<br>Arg | GAT<br>Asp | TTG<br>Leu | GAC<br>Asp<br>245 | GGC<br>Gly | AAG<br>Lys | TCA<br>Ser | CAC<br>His | AAA<br>Lys<br>250 | CCT<br>Pro | CTG<br>Leu | CCC<br>Pro | CTC<br>Leu | GGC<br>Gly<br>255 | GTG<br>Val | 768 |
| GAG<br>Glu | AAC<br>Asn | GAC<br>Asp | CGA<br>Arg<br>260 | GTC<br>Val | TTC<br>Phe | AAT<br>Asn | GAC<br>Asp | CTA<br>Leu<br>265 | TGG<br>Trp | GGG<br>Gly | AAG<br>Lys | GGC<br>Gly | AAT<br>Asn<br>270 | GTG<br>Val | CCT<br>Pro | 816 |
| GTC<br>Val | GTC<br>Val | CTC<br>Leu<br>275 | AAC<br>Asn | AAC<br>Asn | CCA<br>Pro | TAT<br>Tyr | TCA<br>Ser<br>280 | GAG<br>Glu | AAG<br>Lys | GAG<br>Glu | CAG<br>Gln | CCC<br>Pro<br>285 | CCC<br>Pro | ACC<br>Thr | TCA<br>Ser | 864 |
| GGA<br>Gly | AAA<br>Lys<br>290 | CAG<br>Gln | TCC<br>Ser | CCC<br>Pro | ACA<br>Thr | AAG<br>Lys<br>295 | AAT<br>Asn | GGC<br>Gly | AGC<br>Ser | CCC<br>Pro | TCC<br>Ser<br>300 | AAG<br>Lys | TGT<br>Cys | CCA<br>Pro | CGC<br>Arg | 912 |
| TTC<br>Phe<br>305 | CTC<br>Leu | AAG<br>Lys | GTC<br>Val | AAG<br>Lys | AAC<br>Asn<br>310 | TGG<br>Trp | GAG<br>Glu | ACT<br>Thr | GAG<br>Glu | GTG<br>Val<br>315 | GTT<br>Val | CTC<br>Leu | ACT<br>Thr | GAC<br>Asp | ACC<br>Thr<br>320 | 960 |
| CTC<br>Leu | CAC<br>His | CTT<br>Leu | AAG<br>Lys | AGC<br>Ser<br>325 | ACA<br>Thr | TTG<br>Leu | GAA<br>Glu | ACG<br>Thr | GGA<br>Gly<br>330 | TGC<br>Cys | ACT<br>Thr | GAG<br>Glu | TAC<br>Tyr | ATC<br>Ile<br>335 | TGC<br>Cys | 1008 |
| ATG<br>Met | GGC<br>Gly | TCC<br>Ser | ATC<br>Ile | ATG<br>Met | CAT<br>His | CCT<br>Pro | TCT<br>Ser | CAG<br>Gln | CAT<br>His | GCA<br>Ala | AGG<br>Arg | AGG<br>Arg | CCT<br>Pro | GAA<br>Glu | GAC<br>Asp | 1056 |

```
                            340                          345                          350
GTC   CGC   ACA   AAA   GGA   CAG   CTC   TTC   CCT   CTC   GCC   AAA   GAG   TTT   ATT   GAT    1104
Val   Arg   Thr   Lys   Gly   Gln   Leu   Phe   Pro   Leu   Ala   Lys   Glu   Phe   Ile   Asp
            355                     360                     365

CAA   TAC   TAT   TCA   TCA   ATT   AAA   AGA   TTT   GGC   TCC   AAA   GCC   CAC   ATG   GAA    1152
Gln   Tyr   Tyr   Ser   Ser   Ile   Lys   Arg   Phe   Gly   Ser   Lys   Ala   His   Met   Glu
            370                     375                     380

AGG   CTG   GAA   GAG   GTG   AAC   AAA   GAG   ATC   GAC   ACC   ACT   AGC   ACT   TAC   CAG    1200
Arg   Leu   Glu   Glu   Val   Asn   Lys   Glu   Ile   Asp   Thr   Thr   Ser   Thr   Tyr   Gln
385                           390                     395                           400

CTC   AAG   GAC   ACA   GAG   CTC   ATC   TAT   GGG   GCC   AAG   CAC   GCC   TGG   CGG   AAT    1248
Leu   Lys   Asp   Thr   Glu   Leu   Ile   Tyr   Gly   Ala   Lys   His   Ala   Trp   Arg   Asn
                        405                     410                           415

GCC   TCG   CGC   TGT   GTG   GGC   AGG   ATC   CAG   TGG   TCC   AAG   CTG   CAG   GTA   TTC    1296
Ala   Ser   Arg   Cys   Val   Gly   Arg   Ile   Gln   Trp   Ser   Lys   Leu   Gln   Val   Phe
            420                     425                           430

GAT   GCC   CGT   GAC   TGC   ACC   ACG   GCC   CAC   GGG   ATG   TTC   AAC   TAC   ATC   TGT    1344
Asp   Ala   Arg   Asp   Cys   Thr   Thr   Ala   His   Gly   Met   Phe   Asn   Tyr   Ile   Cys
            435                     440                     445

AAC   CAT   GTC   AAG   TAT   GCC   ACC   AAC   AAA   GGG   AAC   CTC   AGG   TCT   GCC   ATC    1392
Asn   His   Val   Lys   Tyr   Ala   Thr   Asn   Lys   Gly   Asn   Leu   Arg   Ser   Ala   Ile
      450                           455                     460

ACC   ATA   TTC   CCC   CAG   AGG   ACA   GAC   GGC   AAG   CAC   GAC   TTC   CGA   GTC   TGG    1440
Thr   Ile   Phe   Pro   Gln   Arg   Thr   Asp   Gly   Lys   His   Asp   Phe   Arg   Val   Trp
465                           470                     475                           480

AAC   TCC   CAG   CTC   ATC   CGC   TAC   GCT   GGC   TAC   AAG   CAG   CCT   GAC   GGC   TCC    1488
Asn   Ser   Gln   Leu   Ile   Arg   Tyr   Ala   Gly   Tyr   Lys   Gln   Pro   Asp   Gly   Ser
                        485                     490                           495

ACC   CTG   GGG   GAC   CCA   GCC   AAT   GTG   CAG   TTC   ACA   GAG   ATA   TGC   ATA   CAG    1536
Thr   Leu   Gly   Asp   Pro   Ala   Asn   Val   Gln   Phe   Thr   Glu   Ile   Cys   Ile   Gln
                  500                     505                           510

CAG   GGC   TGG   AAA   CCG   CCT   AGA   GGC   CGC   TTC   GAT   GTC   CTG   CCG   CTC   CTG    1584
Gln   Gly   Trp   Lys   Pro   Pro   Arg   Gly   Arg   Phe   Asp   Val   Leu   Pro   Leu   Leu
            515                     520                           525

CTT   CAG   GCC   AAC   GGC   AAT   GAC   CCT   GAG   CTC   TTC   CAG   ATT   CCT   CCA   GAG    1632
Leu   Gln   Ala   Asn   Gly   Asn   Asp   Pro   Glu   Leu   Phe   Gln   Ile   Pro   Pro   Glu
      530                           535                     540

CTG   GTG   TTG   GAA   GTT   CCC   ATC   AGG   CAC   CCC   AAG   TTT   GAG   TGG   TTC   AAG    1680
Leu   Val   Leu   Glu   Val   Pro   Ile   Arg   His   Pro   Lys   Phe   Glu   Trp   Phe   Lys
545                           550                     555                           560

GAC   CTG   GGG   CTG   AAG   TGG   TAC   GGC   CTC   CCC   GCC   GTG   TCC   AAC   ATG   CTC    1728
Asp   Leu   Gly   Leu   Lys   Trp   Tyr   Gly   Leu   Pro   Ala   Val   Ser   Asn   Met   Leu
                        565                     570                           575

CTA   GAG   ATT   GGC   GGC   CTG   GAG   TTC   AGC   GCC   TGT   CCC   TTC   AGT   GGC   TGG    1776
Leu   Glu   Ile   Gly   Gly   Leu   Glu   Phe   Ser   Ala   Cys   Pro   Phe   Ser   Gly   Trp
                  580                     585                           590

TAC   ATG   GGC   ACA   GAG   ATT   GGT   GTC   CGC   GAC   TAC   TGT   GAC   AAC   TCC   CGC    1824
Tyr   Met   Gly   Thr   Glu   Ile   Gly   Val   Arg   Asp   Tyr   Cys   Asp   Asn   Ser   Arg
            595                     600                     605

TAC   AAT   ATC   CTG   GAG   GAA   GTG   GCC   AAG   AAG   ATG   AAC   TTA   GAC   ATG   AGG    1872
Tyr   Asn   Ile   Leu   Glu   Glu   Val   Ala   Lys   Lys   Met   Asn   Leu   Asp   Met   Arg
      610                           615                     620

AAG   ACG   TCC   TCC   CTG   TGG   AAG   GAC   CAG   GCG   CTG   GTG   GAG   ATC   AAT   ATC    1920
Lys   Thr   Ser   Ser   Leu   Trp   Lys   Asp   Gln   Ala   Leu   Val   Glu   Ile   Asn   Ile
625                           630                     635                           640

GCG   GTT   CTC   TAT   AGC   TTC   CAG   AGT   GAC   AAA   GTG   ACC   ATT   GTT   GAC   CAT    1968
Ala   Val   Leu   Tyr   Ser   Phe   Gln   Ser   Asp   Lys   Val   Thr   Ile   Val   Asp   His
                        645                     650                           655

CAC   TCC   GCC   ACC   GAG   TCC   TTC   ATT   AAG   CAC   ATG   GAG   AAT   GAG   TAC   CGC    2016
His   Ser   Ala   Thr   Glu   Ser   Phe   Ile   Lys   His   Met   Glu   Asn   Glu   Tyr   Arg
```

-continued

|  |  |  |  |  |  |  | 660 |  |  |  | 665 |  |  |  | 670 |  |  |  |
|---|---|---|---|---|---|---|---|---|---|---|---|---|---|---|---|---|---|---|
| TGC | CGG | GGG | GGC | TGC | CCT | GCC | GAC | TGG | GTG | TGG | ATC | GTG | CCC | CCC | ATG |  |  | 2064 |
| Cys | Arg | Gly | Gly | Cys | Pro | Ala | Asp | Trp | Val | Trp | Ile | Val | Pro | Pro | Met |  |  |  |
|  | 675 |  |  |  |  | 680 |  |  |  |  | 685 |  |  |  |  |  |  |  |
| TCC | GGA | AGC | ATC | ACC | CCT | GTG | TTC | CAC | CAG | GAG | ATG | CTC | AAC | TAC | CGG |  |  | 2112 |
| Ser | Gly | Ser | Ile | Thr | Pro | Val | Phe | His | Gln | Glu | Met | Leu | Asn | Tyr | Arg |  |  |  |
|  | 690 |  |  |  |  | 695 |  |  |  |  | 700 |  |  |  |  |  |  |  |
| CTC | ACC | CCC | TCC | TTC | GAA | TAC | CAG | CCT | GAT | CCC | TGG | AAC | ACG | CAT | GTC |  |  | 2160 |
| Leu | Thr | Pro | Ser | Phe | Glu | Tyr | Gln | Pro | Asp | Pro | Trp | Asn | Thr | His | Val |  |  |  |
| 705 |  |  |  |  | 710 |  |  |  |  | 715 |  |  |  |  | 720 |  |  |  |
| TGG | AAA | GGC | ACC | AAC | GGG | ACC | CCC | ACA | AAG | CGG | CGA | GCC | ATC | GGC | TTC |  |  | 2208 |
| Trp | Lys | Gly | Thr | Asn | Gly | Thr | Pro | Thr | Lys | Arg | Arg | Ala | Ile | Gly | Phe |  |  |  |
|  |  |  |  | 725 |  |  |  |  | 730 |  |  |  |  | 735 |  |  |  |  |
| AAG | AAG | CTA | GCA | GAA | GCT | GTC | AAG | TTC | TCG | GCC | AAG | CTG | ATG | GGG | CAG |  |  | 2256 |
| Lys | Lys | Leu | Ala | Glu | Ala | Val | Lys | Phe | Ser | Ala | Lys | Leu | Met | Gly | Gln |  |  |  |
|  |  |  | 740 |  |  |  |  | 745 |  |  |  |  | 750 |  |  |  |  |  |
| GCT | ATG | GCC | AAG | AGG | GTG | AAA | GCG | ACC | ATC | CTC | TAT | GCC | ACA | GAG | ACA |  |  | 2304 |
| Ala | Met | Ala | Lys | Arg | Val | Lys | Ala | Thr | Ile | Leu | Tyr | Ala | Thr | Glu | Thr |  |  |  |
|  |  | 755 |  |  |  |  | 760 |  |  |  |  | 765 |  |  |  |  |  |  |
| GGC | AAA | TCG | CAA | GCT | TAT | GCC | AAG | ACC | TTG | TGT | GAG | ATC | TTC | AAA | CAC |  |  | 2352 |
| Gly | Lys | Ser | Gln | Ala | Tyr | Ala | Lys | Thr | Leu | Cys | Glu | Ile | Phe | Lys | His |  |  |  |
|  | 770 |  |  |  |  | 775 |  |  |  |  | 780 |  |  |  |  |  |  |  |
| GCC | TTT | GAT | GCC | AAG | GTG | ATG | TCC | ATG | GAA | GAA | TAT | GAC | ATT | GTG | CAC |  |  | 2400 |
| Ala | Phe | Asp | Ala | Lys | Val | Met | Ser | Met | Glu | Glu | Tyr | Asp | Ile | Val | His |  |  |  |
| 785 |  |  |  |  | 790 |  |  |  |  | 795 |  |  |  |  | 800 |  |  |  |
| CTG | GAA | CAT | GAA | ACT | CTG | GTC | CTT | GTG | GTC | ACC | AGC | ACC | TTT | GGC | AAT |  |  | 2448 |
| Leu | Glu | His | Glu | Thr | Leu | Val | Leu | Val | Val | Thr | Ser | Thr | Phe | Gly | Asn |  |  |  |
|  |  |  |  | 805 |  |  |  |  | 810 |  |  |  |  | 815 |  |  |  |  |
| GGA | GAT | CCC | CCT | GAG | AAT | GGG | GAG | AAA | TTC | GGC | TGT | GCT | TTG | ATG | GAA |  |  | 2496 |
| Gly | Asp | Pro | Pro | Glu | Asn | Gly | Glu | Lys | Phe | Gly | Cys | Ala | Leu | Met | Glu |  |  |  |
|  |  |  | 820 |  |  |  |  | 825 |  |  |  |  | 830 |  |  |  |  |  |
| ATG | AGG | CAC | CCC | AAC | TCT | GTG | CAG | GAA | GAA | AGG | AAG | AGC | TAC | AAG | GTC |  |  | 2544 |
| Met | Arg | His | Pro | Asn | Ser | Val | Gln | Glu | Glu | Arg | Lys | Ser | Tyr | Lys | Val |  |  |  |
|  |  | 835 |  |  |  |  | 840 |  |  |  |  | 845 |  |  |  |  |  |  |
| CGA | TTC | AAC | AGC | GTC | TCC | TCC | TAC | TCT | GAC | TCC | CAA | AAA | TCA | TCA | GGC |  |  | 2592 |
| Arg | Phe | Asn | Ser | Val | Ser | Ser | Tyr | Ser | Asp | Ser | Gln | Lys | Ser | Ser | Gly |  |  |  |
|  | 850 |  |  |  |  | 855 |  |  |  |  | 860 |  |  |  |  |  |  |  |
| GAT | GGG | CCC | GAC | CTC | AGA | GAC | AAC | TTT | GAG | AGT | GCT | GGA | CCC | CTG | GCC |  |  | 2640 |
| Asp | Gly | Pro | Asp | Leu | Arg | Asp | Asn | Phe | Glu | Ser | Ala | Gly | Pro | Leu | Ala |  |  |  |
| 865 |  |  |  |  | 870 |  |  |  |  | 875 |  |  |  |  | 880 |  |  |  |
| AAT | GTG | AGG | TTC | TCA | GTT | TTT | GGC | CTC | GGC | TCA | CGA | GCA | TAC | CCT | CAC |  |  | 2688 |
| Asn | Val | Arg | Phe | Ser | Val | Phe | Gly | Leu | Gly | Ser | Arg | Ala | Tyr | Pro | His |  |  |  |
|  |  |  |  | 885 |  |  |  |  | 890 |  |  |  |  | 895 |  |  |  |  |
| TTT | TGC | GCC | TTC | GGA | CAC | GCT | GTG | GAC | ACC | CTC | CTG | GAA | GAA | CTG | GGA |  |  | 2736 |
| Phe | Cys | Ala | Phe | Gly | His | Ala | Val | Asp | Thr | Leu | Leu | Glu | Glu | Leu | Gly |  |  |  |
|  |  |  | 900 |  |  |  |  | 905 |  |  |  |  | 910 |  |  |  |  |  |
| GGG | GAG | AGG | ATC | CTG | AAG | ATG | AGG | GAA | GGG | GAT | GAG | CTC | TGT | GGG | CAG |  |  | 2784 |
| Gly | Glu | Arg | Ile | Leu | Lys | Met | Arg | Glu | Gly | Asp | Glu | Leu | Cys | Gly | Gln |  |  |  |
|  |  | 915 |  |  |  |  | 920 |  |  |  |  | 925 |  |  |  |  |  |  |
| GAA | GAG | GCT | TTC | AGG | ACC | TGG | GCC | AAG | AAG | GTC | TTC | AAG | GCA | GCC | TGT |  |  | 2832 |
| Glu | Glu | Ala | Phe | Arg | Thr | Trp | Ala | Lys | Lys | Val | Phe | Lys | Ala | Ala | Cys |  |  |  |
|  | 930 |  |  |  |  | 935 |  |  |  |  | 940 |  |  |  |  |  |  |  |
| GAT | GTC | TTC | TGT | GTG | GGA | GAT | GAT | GTC | AAC | ATT | GAA | AAG | GCC | AAC | AAT |  |  | 2880 |
| Asp | Val | Phe | Cys | Val | Gly | Asp | Asp | Val | Asn | Ile | Glu | Lys | Ala | Asn | Asn |  |  |  |
| 945 |  |  |  |  | 950 |  |  |  |  | 955 |  |  |  |  | 960 |  |  |  |
| TCC | CTC | ATC | AGC | AAT | GAT | CGC | AGC | TGG | AAG | AGA | AAC | AAG | TTC | CGC | CTC |  |  | 2928 |
| Ser | Leu | Ile | Ser | Asn | Asp | Arg | Ser | Trp | Lys | Arg | Asn | Lys | Phe | Arg | Leu |  |  |  |
|  |  |  |  | 965 |  |  |  |  | 970 |  |  |  |  | 975 |  |  |  |  |
| ACC | TTT | GTG | GCC | GAA | GCT | CCA | GAA | CTC | ACA | CAA | GGT | CTA | TCC | AAT | GTC |  |  | 2976 |
| Thr | Phe | Val | Ala | Glu | Ala | Pro | Glu | Leu | Thr | Gln | Gly | Leu | Ser | Asn | Val |  |  |  |

-continued

|  |  |  |  |  |  |  |  |  |  |  |  |  |  |  |  |
|---|---|---|---|---|---|---|---|---|---|---|---|---|---|---|---|
|  |  |  |  | 980 |  |  |  |  | 985 |  |  |  |  | 990 |  |
| CAC | AAA | AAG | CGA | GTC | TCA | GCT | GCC | CGG | CTC | CTT | AGC | CGT | CAA | AAC | CTC | 3024 |
| His | Lys | Lys | Arg | Val | Ser | Ala | Ala | Arg | Leu | Leu | Ser | Arg | Gln | Asn | Leu |  |
| 995 |  |  |  |  | 1000 |  |  |  |  |  | 1005 |  |  |  |  |  |
| CAG | AGC | CCT | AAA | TCC | AGT | CGG | TCA | ACT | ATC | TTC | GTG | CGT | CTC | CAC | ACC | 3072 |
| Gln | Ser | Pro | Lys | Ser | Ser | Arg | Ser | Thr | Ile | Phe | Val | Arg | Leu | His | Thr |  |
| 1010 |  |  |  |  | 1015 |  |  |  |  | 1020 |  |  |  |  |  |  |
| AAC | GGG | AGC | CAG | GAG | CTG | CAG | TAC | CAG | CCT | GGG | GAC | CAC | CTG | GGT | GTC | 3120 |
| Asn | Gly | Ser | Gln | Glu | Leu | Gln | Tyr | Gln | Pro | Gly | Asp | His | Leu | Gly | Val |  |
| 1025 |  |  |  |  | 1030 |  |  |  |  | 1035 |  |  |  |  | 1040 |  |
| TTC | CCT | GGC | AAC | CAC | GAG | GAC | CTC | GTG | AAT | GCC | CTG | ATC | GAG | CGG | CTG | 3168 |
| Phe | Pro | Gly | Asn | His | Glu | Asp | Leu | Val | Asn | Ala | Leu | Ile | Glu | Arg | Leu |  |
|  |  |  |  | 1045 |  |  |  |  | 1050 |  |  |  |  | 1055 |  |  |
| GAG | GAC | GCG | CCG | CCT | GTC | AAC | CAG | ATG | GTG | AAA | GTG | GAA | CTG | CTG | GAG | 3216 |
| Glu | Asp | Ala | Pro | Pro | Val | Asn | Gln | Met | Val | Lys | Val | Glu | Leu | Leu | Glu |  |
|  |  |  | 1060 |  |  |  |  | 1065 |  |  |  |  | 1070 |  |  |  |
| GAG | CGG | AAC | ACG | GCT | TTA | GGT | GTC | ATC | AGT | AAC | TGG | ACA | GAC | GAG | CTC | 3264 |
| Glu | Arg | Asn | Thr | Ala | Leu | Gly | Val | Ile | Ser | Asn | Trp | Thr | Asp | Glu | Leu |  |
|  |  |  | 1075 |  |  |  |  | 1080 |  |  |  |  | 1085 |  |  |  |
| CGC | CTC | CCA | CCC | TGC | ACC | ATC | TTC | CAG | GCC | TTC | AAG | TAC | TAC | CTG | GAC | 3312 |
| Arg | Leu | Pro | Pro | Cys | Thr | Ile | Phe | Gln | Ala | Phe | Lys | Tyr | Tyr | Leu | Asp |  |
|  |  |  | 1090 |  |  |  |  | 1095 |  |  |  |  | 1100 |  |  |  |
| ATC | ACC | ACG | CCA | CCA | ACG | CCC | CTG | CAG | CTG | CAG | CAG | TTT | GCC | TCC | CTA | 3360 |
| Ile | Thr | Thr | Pro | Pro | Thr | Pro | Leu | Gln | Leu | Gln | Gln | Phe | Ala | Ser | Leu |  |
| 1105 |  |  |  |  | 1110 |  |  |  |  | 1115 |  |  |  |  | 1120 |  |
| GCT | ACC | AGC | GAG | AAG | GAG | AAG | CAG | CGT | CTG | CTG | GTC | CTC | AGC | AAG | GGT | 3408 |
| Ala | Thr | Ser | Glu | Lys | Glu | Lys | Gln | Arg | Leu | Leu | Val | Leu | Ser | Lys | Gly |  |
|  |  |  |  |  | 1125 |  |  |  |  | 1130 |  |  |  |  | 1135 |  |
| TTG | CAG | GAG | TAC | GAG | GAA | TGG | AAA | TGG | GGC | AAG | AAC | CCC | ACC | ATC | GTG | 3456 |
| Leu | Gln | Glu | Tyr | Glu | Glu | Trp | Lys | Trp | Gly | Lys | Asn | Pro | Thr | Ile | Val |  |
|  |  |  | 1140 |  |  |  |  | 1145 |  |  |  |  | 1150 |  |  |  |
| GAG | GTG | CTG | GAG | GAG | TTC | CCA | TCT | ATC | CAG | ATG | CCG | GCC | ACC | CTG | CTC | 3504 |
| Glu | Val | Leu | Glu | Glu | Phe | Pro | Ser | Ile | Gln | Met | Pro | Ala | Thr | Leu | Leu |  |
|  |  | 1155 |  |  |  |  | 1160 |  |  |  |  | 1165 |  |  |  |  |
| CTG | ACC | CAG | CTG | TCC | CTG | CTG | CAG | CCC | CGC | TAC | TAT | TCC | ATC | AGC | TCC | 3552 |
| Leu | Thr | Gln | Leu | Ser | Leu | Leu | Gln | Pro | Arg | Tyr | Tyr | Ser | Ile | Ser | Ser |  |
|  | 1170 |  |  |  |  | 1175 |  |  |  |  | 1180 |  |  |  |  |  |
| TCC | CCA | GAC | ATG | TAC | CCT | GAT | GAA | GTG | CAC | CTC | ACT | GTG | GCC | ATC | GTT | 3600 |
| Ser | Pro | Asp | Met | Tyr | Pro | Asp | Glu | Val | His | Leu | Thr | Val | Ala | Ile | Val |  |
| 1185 |  |  |  | 1190 |  |  |  |  | 1195 |  |  |  |  | 1200 |  |  |
| TCC | TAC | CGC | ACT | CGA | GAT | GGA | GAA | GGA | CCA | ATT | CAC | CAC | GGC | GTA | TGC | 3648 |
| Ser | Tyr | Arg | Thr | Arg | Asp | Gly | Glu | Gly | Pro | Ile | His | His | Gly | Val | Cys |  |
|  |  |  |  | 1205 |  |  |  |  | 1210 |  |  |  |  | 1215 |  |  |
| TCC | TCC | TGG | CTC | AAC | CGG | ATA | CAG | GCT | GAC | GAA | CTG | GTC | CCC | TGT | TTC | 3696 |
| Ser | Ser | Trp | Leu | Asn | Arg | Ile | Gln | Ala | Asp | Glu | Leu | Val | Pro | Cys | Phe |  |
|  |  |  | 1220 |  |  |  |  | 1225 |  |  |  |  | 1230 |  |  |  |
| GTG | AGA | GGA | GCA | CCC | AGC | TTC | CAC | CTG | CCC | CGG | AAC | CCC | CAA | GTC | CCC | 3744 |
| Val | Arg | Gly | Ala | Pro | Ser | Phe | His | Leu | Pro | Arg | Asn | Pro | Gln | Val | Pro |  |
|  |  | 1235 |  |  |  |  | 1240 |  |  |  |  | 1245 |  |  |  |  |
| TGC | ATC | CTC | GTT | GGA | CCA | GGC | ACC | GGC | ATT | GCC | CCT | TTC | CGA | AGC | TTC | 3792 |
| Cys | Ile | Leu | Val | Gly | Pro | Gly | Thr | Gly | Ile | Ala | Pro | Phe | Arg | Ser | Phe |  |
|  | 1250 |  |  |  |  | 1255 |  |  |  |  | 1260 |  |  |  |  |  |
| TGG | CAA | CAG | CGG | CAA | TTT | GAT | ATC | CAA | CAC | AAA | GGA | ATG | AAC | CCC | TGC | 3840 |
| Trp | Gln | Gln | Arg | Gln | Phe | Asp | Ile | Gln | His | Lys | Gly | Met | Asn | Pro | Cys |  |
| 1265 |  |  |  |  | 1270 |  |  |  |  | 1275 |  |  |  |  | 1280 |  |
| CCC | ATG | GTC | CTG | GTC | TTC | GGG | TGC | CGG | CAA | TCC | AAG | ATA | GAT | CAT | ATC | 3888 |
| Pro | Met | Val | Leu | Val | Phe | Gly | Cys | Arg | Gln | Ser | Lys | Ile | Asp | His | Ile |  |
|  |  |  |  | 1285 |  |  |  |  | 1290 |  |  |  |  | 1295 |  |  |
| TAC | AGG | GAA | GAG | ACC | CTG | CAG | GCC | AAG | AAC | AAG | GGG | GTC | TTC | AGA | GAG | 3936 |
| Tyr | Arg | Glu | Glu | Thr | Leu | Gln | Ala | Lys | Asn | Lys | Gly | Val | Phe | Arg | Glu |  |

```
                         1300                         1305                         1310
CTG  TAC  ACG  GCT  TAC  TCC  CGG  GAG  CCA  GAC  AAA  CCA  AAG  AAG  TAC  GTG              3984
Leu  Tyr  Thr  Ala  Tyr  Ser  Arg  Glu  Pro  Asp  Lys  Pro  Lys  Lys  Tyr  Val
               1315                    1320                    1325

CAG  GAC  ATC  CTG  CAG  GAG  CAG  CTG  GCG  GAG  TCT  GTG  TAC  CGA  GCC  CTG              4032
Gln  Asp  Ile  Leu  Gln  Glu  Gln  Leu  Ala  Glu  Ser  Val  Tyr  Arg  Ala  Leu
               1330                    1335                    1340

AAG  GAG  CAA  GGG  GGC  CAC  ATA  TAC  GTC  TGT  GGG  GAC  GTC  ACC  ATG  GCT              4080
Lys  Glu  Gln  Gly  Gly  His  Ile  Tyr  Val  Cys  Gly  Asp  Val  Thr  Met  Ala
1345                         1350                    1355                    1360

GCT  GAT  GTC  CTC  AAA  GCC  ATC  CAG  CGC  ATC  ATG  ACC  CAG  CAG  GGG  AAG              4128
Ala  Asp  Val  Leu  Lys  Ala  Ile  Gln  Arg  Ile  Met  Thr  Gln  Gln  Gly  Lys
               1365                    1370                    1375

CTC  TCG  GCA  GAG  GAC  GCC  GGC  GTA  TTC  ATC  AGC  CGG  ATG  AGG  GAT  GAC              4176
Leu  Ser  Ala  Glu  Asp  Ala  Gly  Val  Phe  Ile  Ser  Arg  Met  Arg  Asp  Asp
               1380                    1385                    1390

AAC  CGA  TAC  CAT  GAG  GAT  ATT  TTT  GGA  GTC  ACC  CTG  CGA  ACG  TAC  GAA              4224
Asn  Arg  Tyr  His  Glu  Asp  Ile  Phe  Gly  Val  Thr  Leu  Arg  Thr  Tyr  Glu
               1395                    1400                    1405

GTG  ACC  AAC  CGC  CTT  AGA  TCT  GAG  TCC  ATT  GCC  TTC  ATT  GAA  GAG  AGC              4272
Val  Thr  Asn  Arg  Leu  Arg  Ser  Glu  Ser  Ile  Ala  Phe  Ile  Glu  Glu  Ser
1410                         1415                    1420

AAA  AAA  GAC  ACC  GAT  GAG  GTT  TTC  AGC  TCC  TAACTGGACC  CTCTTGCCCA                    4322
Lys  Lys  Asp  Thr  Asp  Glu  Val  Phe  Ser  Ser
1425                         1430                    143

GCCGGCTGCA  AGTTTGTAAG  CGCGGGACAG  A                                                        4353
```

( 2 ) INFORMATION FOR SEQ ID NO:19:

( i ) SEQUENCE CHARACTERISTICS:
        ( A ) LENGTH: 1434 amino acids
        ( B ) TYPE: amino acid
        ( D ) TOPOLOGY: linear ( i i ) MOLECULE TYPE: protein ( x i ) SEQUENCE DESCRIPTION: SEQ ID NO:19:

```
Met  Glu  Asp  His  Met  Phe  Gly  Val  Gln  Gln  Ile  Gln  Pro  Asn  Val  Ile
 1                    5                        10                        15

Ser  Val  Arg  Leu  Phe  Lys  Arg  Lys  Val  Gly  Gly  Leu  Gly  Phe  Leu  Val
                    20                        25                        30

Lys  Glu  Arg  Val  Ser  Lys  Pro  Pro  Val  Ile  Ile  Ser  Asp  Leu  Ile  Arg
               35                        40                        45

Gly  Gly  Ala  Ala  Glu  Gln  Ser  Gly  Leu  Ile  Gln  Ala  Gly  Asp  Ile  Ile
          50                        55                        60

Leu  Ala  Val  Asn  Gly  Arg  Pro  Leu  Val  Asp  Leu  Ser  Tyr  Asp  Ser  Ala
 65                        70                        75                        80

Leu  Glu  Val  Leu  Arg  Gly  Ile  Ala  Ser  Glu  Thr  His  Val  Val  Leu  Ile
                    85                        90                        95

Leu  Arg  Gly  Pro  Glu  Gly  Phe  Thr  Thr  His  Leu  Glu  Thr  Thr  Phe  Thr
              100                       105                       110

Gly  Asp  Gly  Thr  Pro  Lys  Thr  Ile  Arg  Val  Thr  Gln  Pro  Leu  Gly  Pro
              115                       120                       125

Pro  Thr  Lys  Ala  Val  Asp  Leu  Ser  His  Gln  Pro  Pro  Ala  Gly  Lys  Glu
         130                       135                       140

Gln  Pro  Leu  Ala  Val  Asp  Gly  Ala  Ser  Gly  Pro  Gly  Asn  Gly  Pro  Gln
145                       150                       155                       160

His  Ala  Tyr  Asp  Asp  Gly  Gln  Glu  Ala  Gly  Ser  Leu  Pro  His  Ala  Asn
                   165                       170                       175
```

```
Gly  Leu  Ala  Pro  Arg  Pro  Pro  Gly  Gln  Asp  Pro  Ala  Lys  Lys  Ala  Thr
               180                      185                      190

Arg  Val  Ser  Leu  Gln  Gly  Arg  Glu  Asn  Asn  Glu  Leu  Leu  Lys  Glu
          195                      200                      205

Ile  Glu  Pro  Val  Leu  Ser  Leu  Thr  Ser  Gly  Ser  Arg  Gly  Val  Lys
          210                      215                      220

Gly  Gly  Ala  Pro  Ala  Lys  Ala  Glu  Met  Lys  Asp  Met  Gly  Ile  Gln  Val
225                           230                     235                     240

Asp  Arg  Asp  Leu  Asp  Gly  Lys  Ser  His  Lys  Pro  Leu  Pro  Leu  Gly  Val
               245                      250                      255

Glu  Asn  Asp  Arg  Val  Phe  Asn  Asp  Leu  Trp  Gly  Lys  Gly  Asn  Val  Pro
               260                      265                      270

Val  Val  Leu  Asn  Asn  Pro  Tyr  Ser  Glu  Lys  Glu  Gln  Pro  Pro  Thr  Ser
               275                      280                      285

Gly  Lys  Gln  Ser  Pro  Thr  Lys  Asn  Gly  Ser  Pro  Ser  Lys  Cys  Pro  Arg
          290                      295                      300

Phe  Leu  Lys  Val  Lys  Asn  Trp  Glu  Thr  Glu  Val  Val  Leu  Thr  Asp  Thr
305                           310                     315                     320

Leu  His  Leu  Lys  Ser  Thr  Leu  Glu  Thr  Gly  Cys  Thr  Glu  Tyr  Ile  Cys
               325                      330                      335

Met  Gly  Ser  Ile  Met  His  Pro  Ser  Gln  His  Ala  Arg  Arg  Pro  Glu  Asp
               340                      345                      350

Val  Arg  Thr  Lys  Gly  Gln  Leu  Phe  Pro  Leu  Ala  Lys  Glu  Phe  Ile  Asp
               355                      360                      365

Gln  Tyr  Tyr  Ser  Ser  Ile  Lys  Arg  Phe  Gly  Ser  Lys  Ala  His  Met  Glu
          370                      375                      380

Arg  Leu  Glu  Glu  Val  Asn  Lys  Glu  Ile  Asp  Thr  Thr  Ser  Thr  Tyr  Gln
385                           390                     395                     400

Leu  Lys  Asp  Thr  Glu  Leu  Ile  Tyr  Gly  Ala  Lys  His  Ala  Trp  Arg  Asn
               405                      410                      415

Ala  Ser  Arg  Cys  Val  Gly  Arg  Ile  Gln  Trp  Ser  Lys  Leu  Gln  Val  Phe
               420                      425                      430

Asp  Ala  Arg  Asp  Cys  Thr  Thr  Ala  His  Gly  Met  Phe  Asn  Tyr  Ile  Cys
               435                      440                      445

Asn  His  Val  Lys  Tyr  Ala  Thr  Asn  Lys  Gly  Asn  Leu  Arg  Ser  Ala  Ile
     450                      455                      460

Thr  Ile  Phe  Pro  Gln  Arg  Thr  Asp  Gly  Lys  His  Asp  Phe  Arg  Val  Trp
465                           470                     475                     480

Asn  Ser  Gln  Leu  Ile  Arg  Tyr  Ala  Gly  Tyr  Lys  Gln  Pro  Asp  Gly  Ser
               485                      490                      495

Thr  Leu  Gly  Asp  Pro  Ala  Asn  Val  Gln  Phe  Thr  Glu  Ile  Cys  Ile  Gln
               500                      505                      510

Gln  Gly  Trp  Lys  Pro  Pro  Arg  Gly  Arg  Phe  Asp  Val  Leu  Pro  Leu  Leu
          515                      520                      525

Leu  Gln  Ala  Asn  Gly  Asn  Asp  Pro  Glu  Leu  Phe  Gln  Ile  Pro  Pro  Glu
     530                      535                      540

Leu  Val  Leu  Glu  Val  Pro  Ile  Arg  His  Pro  Lys  Phe  Glu  Trp  Phe  Lys
545                      550                      555                      560

Asp  Leu  Gly  Leu  Lys  Trp  Tyr  Gly  Leu  Pro  Ala  Val  Ser  Asn  Met  Leu
               565                      570                      575

Leu  Glu  Ile  Gly  Gly  Leu  Glu  Phe  Ser  Ala  Cys  Pro  Phe  Ser  Gly  Trp
               580                      585                      590

Tyr  Met  Gly  Thr  Glu  Ile  Gly  Val  Arg  Asp  Tyr  Cys  Asp  Asn  Ser  Arg
```

|     |     |     | 595 |     |     |     | 600 |     |     |     | 605 |     |     |
| --- | --- | --- | --- | --- | --- | --- | --- | --- | --- | --- | --- | --- | --- |

Tyr Asn Ile Leu Glu Glu Val Ala Lys Lys Met Asn Leu Asp Met Arg
610                     615                     620

Lys Thr Ser Ser Leu Trp Lys Asp Gln Ala Leu Val Glu Ile Asn Ile
625                     630                     635                     640

Ala Val Leu Tyr Ser Phe Gln Ser Asp Lys Val Thr Ile Val Asp His
                        645                     650                     655

His Ser Ala Thr Glu Ser Phe Ile Lys His Met Glu Asn Glu Tyr Arg
                        660                     665                     670

Cys Arg Gly Gly Cys Pro Ala Asp Trp Val Trp Ile Val Pro Pro Met
            675                     680                     685

Ser Gly Ser Ile Thr Pro Val Phe His Gln Glu Met Leu Asn Tyr Arg
    690                     695                     700

Leu Thr Pro Ser Phe Glu Tyr Gln Pro Asp Pro Trp Asn Thr His Val
705                     710                     715                     720

Trp Lys Gly Thr Asn Gly Thr Pro Thr Lys Arg Ala Ile Gly Phe
                    725                     730                     735

Lys Lys Leu Ala Glu Ala Val Lys Phe Ser Ala Lys Leu Met Gly Gln
                740                     745                     750

Ala Met Ala Lys Arg Val Lys Ala Thr Ile Leu Tyr Ala Thr Glu Thr
            755                     760                     765

Gly Lys Ser Gln Ala Tyr Ala Lys Thr Leu Cys Glu Ile Phe Lys His
    770                     775                     780

Ala Phe Asp Ala Lys Val Met Ser Met Glu Glu Tyr Asp Ile Val His
785                     790                     795                     800

Leu Glu His Glu Thr Leu Val Leu Val Val Thr Ser Thr Phe Gly Asn
                        805                     810                     815

Gly Asp Pro Pro Glu Asn Gly Glu Lys Phe Gly Cys Ala Leu Met Glu
            820                     825                     830

Met Arg His Pro Asn Ser Val Gln Glu Glu Arg Lys Ser Tyr Lys Val
            835                     840                     845

Arg Phe Asn Ser Val Ser Ser Tyr Ser Asp Ser Gln Lys Ser Ser Gly
    850                     855                     860

Asp Gly Pro Asp Leu Arg Asp Asn Phe Glu Ser Ala Gly Pro Leu Ala
865                     870                     875                     880

Asn Val Arg Phe Ser Val Phe Gly Leu Gly Ser Arg Ala Tyr Pro His
                885                     890                     895

Phe Cys Ala Phe Gly His Ala Val Asp Thr Leu Leu Glu Glu Leu Gly
            900                     905                     910

Gly Glu Arg Ile Leu Lys Met Arg Glu Gly Asp Glu Leu Cys Gly Gln
            915                     920                     925

Glu Glu Ala Phe Arg Thr Trp Ala Lys Lys Val Phe Lys Ala Ala Cys
930                     935                     940

Asp Val Phe Cys Val Gly Asp Asp Val Asn Ile Glu Lys Ala Asn Asn
945                     950                     955                     960

Ser Leu Ile Ser Asn Asp Arg Ser Trp Lys Arg Asn Lys Phe Arg Leu
                965                     970                     975

Thr Phe Val Ala Glu Ala Pro Glu Leu Thr Gln Gly Leu Ser Asn Val
            980                     985                     990

His Lys Lys Arg Val Ser Ala Ala Arg Leu Leu Ser Arg Gln Asn Leu
    995                     1000                    1005

Gln Ser Pro Lys Ser Ser Arg Ser Thr Ile Phe Val Arg Leu His Thr
    1010                    1015                    1020

```
Asn  Gly  Ser  Gln  Glu  Leu  Gln  Tyr  Gln  Pro  Gly  Asp  His  Leu  Gly  Val
1025                1030                1035                     1040

Phe  Pro  Gly  Asn  His  Glu  Asp  Leu  Val  Asn  Ala  Leu  Ile  Glu  Arg  Leu
                    1045                1050                     1055

Glu  Asp  Ala  Pro  Pro  Val  Asn  Gln  Met  Val  Lys  Val  Glu  Leu  Glu  Glu
               1060                1065                1070

Glu  Arg  Asn  Thr  Ala  Leu  Gly  Val  Ile  Ser  Asn  Trp  Thr  Asp  Glu  Leu
               1075                1080                1085

Arg  Leu  Pro  Pro  Cys  Thr  Ile  Phe  Gln  Ala  Phe  Lys  Tyr  Tyr  Leu  Asp
               1090                1095                1100

Ile  Thr  Thr  Pro  Pro  Thr  Pro  Leu  Gln  Leu  Gln  Gln  Phe  Ala  Ser  Leu
1105                1110                1115                     1120

Ala  Thr  Ser  Glu  Lys  Glu  Lys  Gln  Arg  Leu  Leu  Val  Leu  Ser  Lys  Gly
               1125                1130                1135

Leu  Gln  Glu  Tyr  Glu  Glu  Trp  Lys  Trp  Gly  Lys  Asn  Pro  Thr  Ile  Val
               1140                1145                1150

Glu  Val  Leu  Glu  Glu  Phe  Pro  Ser  Ile  Gln  Met  Pro  Ala  Thr  Leu  Leu
               1155                1160                1165

Leu  Thr  Gln  Leu  Ser  Leu  Leu  Gln  Pro  Arg  Tyr  Tyr  Ser  Ile  Ser  Ser
               1170                1175                1180

Ser  Pro  Asp  Met  Tyr  Pro  Asp  Glu  Val  His  Leu  Thr  Val  Ala  Ile  Val
1185                1190                1195                     1200

Ser  Tyr  Arg  Thr  Arg  Asp  Gly  Glu  Gly  Pro  Ile  His  His  Gly  Val  Cys
               1205                1210                1215

Ser  Ser  Trp  Leu  Asn  Arg  Ile  Gln  Ala  Asp  Glu  Leu  Val  Pro  Cys  Phe
               1220                1225                1230

Val  Arg  Gly  Ala  Pro  Ser  Phe  His  Leu  Pro  Arg  Asn  Pro  Gln  Val  Pro
               1235                1240                1245

Cys  Ile  Leu  Val  Gly  Pro  Gly  Thr  Gly  Ile  Ala  Pro  Phe  Arg  Ser  Phe
               1250                1255                1260

Trp  Gln  Gln  Arg  Gln  Phe  Asp  Ile  Gln  His  Lys  Gly  Met  Asn  Pro  Cys
1265                1270                1275                     1280

Pro  Met  Val  Leu  Val  Phe  Gly  Cys  Arg  Gln  Ser  Lys  Ile  Asp  His  Ile
               1285                1290                1295

Tyr  Arg  Glu  Glu  Thr  Leu  Gln  Ala  Lys  Asn  Lys  Gly  Val  Phe  Arg  Glu
               1300                1305                1310

Leu  Tyr  Thr  Ala  Tyr  Ser  Arg  Glu  Pro  Asp  Lys  Pro  Lys  Lys  Tyr  Val
               1315                1320                1325

Gln  Asp  Ile  Leu  Gln  Glu  Gln  Leu  Ala  Glu  Ser  Val  Tyr  Arg  Ala  Leu
               1330                1335                1340

Lys  Glu  Gln  Gly  Gly  His  Ile  Tyr  Val  Cys  Gly  Asp  Val  Thr  Met  Ala
1345                1350                1355                     1360

Ala  Asp  Val  Leu  Lys  Ala  Ile  Gln  Arg  Ile  Met  Thr  Gln  Gln  Gly  Lys
               1365                1370                1375

Leu  Ser  Ala  Glu  Asp  Ala  Gly  Val  Phe  Ile  Ser  Arg  Met  Arg  Asp  Asp
               1380                1385                1390

Asn  Arg  Tyr  His  Glu  Asp  Ile  Phe  Gly  Val  Thr  Leu  Arg  Thr  Tyr  Glu
               1395                1400                1405

Val  Thr  Asn  Arg  Leu  Arg  Ser  Glu  Ser  Ile  Ala  Phe  Ile  Glu  Glu  Ser
               1410                1415                1420

Lys  Lys  Asp  Thr  Asp  Glu  Val  Phe  Ser  Ser
1425                1430
```

( 2 ) INFORMATION FOR SEQ ID NO:20:

( i ) SEQUENCE CHARACTERISTICS:
    ( A ) LENGTH: 4780 base pairs
    ( B ) TYPE: nucleic acid
    ( C ) STRANDEDNESS: double
    ( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
    ( C ) INDIVIDUAL ISOLATE: Human NOS-SN gene, Nakane, et al,
        FEBS Lett 316:175 (1993)

( i x ) FEATURE:
    ( A ) NAME/KEY: CDS
    ( B ) LOCATION: 431..4732

( x i ) SEQUENCE DESCRIPTION: SEQ ID NO:20:

```
GAGCGGACGG GCTCATGATG CCTCAGATCT GATCCGCATC TAACAGGCTG GCAATGAAGA      60

TACCCAGAGA ATAGTTCACA TCTATCATGC GTCACTTCTA GACACAGCCA TCAGACGCAT     120

CTCCTCCCCT TTCTGCCTGA CCTTAGGACA CGTCCCACCG CCTCTCTTGA CGTCTGCCTG     180

GTCAACCATC ACTTCCTTAG AGAATAAGGA GAGAGGCGGA TGCAGGAAAT CATGCCACCG     240

ACGGGCCACC AGCCATGAGT GGGTGACGCT GAGCTGACGT CAAAGACAGA GAGGGCTGAA     300

GCCTTGTCAG CACCTGTCAC CCCGGCTCCT GCTCTCCGTG TAGCCTGAAG CCTGGATCCT     360

CCTGGTGAAA TCATCTTGGC CTGATAGCAT TGTGAGGTCT TCAGACAGGA CCCCTCGGAA     420

GCTAGTTACC ATG GAG GAT CAC ATG TTC GGT GTT CAG CAA ATC CAG CCC        469
           Met Glu Asp His Met Phe Gly Val Gln Gln Ile Gln Pro
             1               5                    10

AAT GTC ATT TCT GTT CGT CTC TTC AAG CGC AAA GTT GGG GGC CTG GGA       517
Asn Val Ile Ser Val Arg Leu Phe Lys Arg Lys Val Gly Gly Leu Gly
     15              20                  25

TTT CTG GTG AAG GAG CGG GTC AGT AAG CCG CCC GTG ATC ATC TCT GAC       565
Phe Leu Val Lys Glu Arg Val Ser Lys Pro Pro Val Ile Ile Ser Asp
 30              35                  40                      45

CTG ATT CGT GGG GGC GCC GCA GAG CAG AGT GGC CTC ATC CAG GCC GGA       613
Leu Ile Arg Gly Gly Ala Ala Glu Gln Ser Gly Leu Ile Gln Ala Gly
             50                  55                  60

GAC ATC ATT CTT GCG GTC AAC GGC CGG CCC TTG GTG GAC CTG AGC TAT       661
Asp Ile Ile Leu Ala Val Asn Gly Arg Pro Leu Val Asp Leu Ser Tyr
             65                  70                  75

GAC AGC GCC CTG GAG GTA CTC AGA GGC ATT GCC TCT GAG ACC CAC GTG       709
Asp Ser Ala Leu Glu Val Leu Arg Gly Ile Ala Ser Glu Thr His Val
             80                  85                  90

GTC CTC ATT CTG AGG GGC CCT GAA GGT TTC ACC ACG CAC CTG GAG ACC       757
Val Leu Ile Leu Arg Gly Pro Glu Gly Phe Thr Thr His Leu Glu Thr
         95                  100                 105

ACC TTT ACA GGT GAT GGG ACC CCC AAG ACC ATC CGG GTG ACA CAG CCC       805
Thr Phe Thr Gly Asp Gly Thr Pro Lys Thr Ile Arg Val Thr Gln Pro
110         Phe Thr Gly Asp Gly 115             120                125

CTG GGT CCC CCC ACC AAA GCC GTG GAT CTG TCC CAC CAG CCA CCG GCC       853
Leu Gly Pro Pro Thr Lys Ala Val Asp Leu Ser His Gln Pro Pro Ala
                 130                 135                 140

GGC AAA GAA CAG CCC CTG GCA GTG GAT GGG GCC TCG GGT CCC GGG AAT       901
Gly Lys Glu Gln Pro Leu Ala Val Asp Gly Ala Ser Gly Pro Gly Asn
             145                 150                 155

GGG CCT CAG CAT GCC TAC GAT GAT GGG CAG GAG GCT GGC TCA CTC CCC       949
Gly Pro Gln His Ala Tyr Asp Asp Gly Gln Glu Ala Gly Ser Leu Pro
             160                 165                 170
```

| | | | | | | | | | | | | | | | | |
|---|---|---|---|---|---|---|---|---|---|---|---|---|---|---|---|---|
| CAT | GCC | AAC | GGC | TGG | CCC | CAG | GCC | CCC | AGG | CAG | GAC | CCC | GCG | AAG | AAA | 997 |
| His | Ala | Asn | Gly | Trp | Pro | Gln | Ala | Pro | Arg | Gln | Asp | Pro | Ala | Lys | Lys | |
| 175 | | | | 180 | | | | | | 185 | | | | | | |
| GCA | ACC | AGA | GTC | AGC | CTC | CAA | GGC | AGA | GGG | GAG | AAC | AAT | GAA | CTG | CTC | 1045 |
| Ala | Thr | Arg | Val | Ser | Leu | Gln | Gly | Arg | Gly | Glu | Asn | Asn | Glu | Leu | Leu | |
| 190 | | | | | 195 | | | | | 200 | | | | | 205 | |
| AAG | GAG | ATA | GAG | CCT | GTG | CTG | AGC | CTT | CTC | ACC | AGT | GGG | AGC | AGA | GGG | 1093 |
| Lys | Glu | Ile | Glu | Pro | Val | Leu | Ser | Leu | Leu | Thr | Ser | Gly | Ser | Arg | Gly | |
| | | | | 210 | | | | | 215 | | | | | 220 | | |
| GTC | AAG | GGA | GGG | GCA | CCT | GCC | AAG | GCA | GAG | ATG | AAA | GAT | ATG | GGA | ATC | 1141 |
| Val | Lys | Gly | Gly | Ala | Pro | Ala | Lys | Ala | Glu | Met | Lys | Asp | Met | Gly | Ile | |
| | | | 225 | | | | | 230 | | | | | 235 | | | |
| CAG | GTG | GAC | AGA | GAT | TTG | GAC | GGC | AAG | TCA | CAC | AAA | CCT | CTG | CCC | CTC | 1189 |
| Gln | Val | Asp | Arg | Asp | Leu | Asp | Gly | Lys | Ser | His | Lys | Pro | Leu | Pro | Leu | |
| | | 240 | | | | | 245 | | | | | 250 | | | | |
| GGC | GTG | GAG | AAC | GAC | CGA | GTC | TTC | AAT | GAC | CTA | TGG | GGG | AAG | GGC | AAT | 1237 |
| Gly | Val | Glu | Asn | Asp | Arg | Val | Phe | Asn | Asp | Leu | Trp | Gly | Lys | Gly | Asn | |
| | 255 | | | | | 260 | | | | | 265 | | | | | |
| GTG | CCT | GTC | GTC | CTC | AAC | AAC | CCA | TAT | TCA | GAG | AAG | GAG | CAG | CCC | CCC | 1285 |
| Val | Pro | Val | Val | Leu | Asn | Asn | Pro | Tyr | Ser | Glu | Lys | Glu | Gln | Pro | Pro | |
| 270 | | | | | 275 | | | | | 280 | | | | | 285 | |
| ACC | TCA | GGA | AAA | CAG | TCC | CCC | ACA | AAG | AAT | GGC | AGC | CCC | TCC | AAG | TGT | 1333 |
| Thr | Ser | Gly | Lys | Gln | Ser | Pro | Thr | Lys | Asn | Gly | Ser | Pro | Ser | Lys | Cys | |
| | | | | 290 | | | | | 295 | | | | | 300 | | |
| CCA | CGC | TTC | CTC | AAG | GTC | AAG | AAC | TGG | GAG | ACT | GAG | GTG | GTT | CTC | ACT | 1381 |
| Pro | Arg | Phe | Leu | Lys | Val | Lys | Asn | Trp | Glu | Thr | Glu | Val | Val | Leu | Thr | |
| | | | 305 | | | | | 310 | | | | | 315 | | | |
| GAC | ACC | CTC | CAC | CTT | AAG | AGC | ACA | TTG | GAA | ACG | GGA | TGC | ACT | GAG | TAC | 1429 |
| Asp | Thr | Leu | His | Leu | Lys | Ser | Thr | Leu | Glu | Thr | Gly | Cys | Thr | Glu | Tyr | |
| | | 320 | | | | | 325 | | | | | 330 | | | | |
| ATC | TGC | ATG | GGC | TCC | ATC | ATG | CAT | CCT | TCT | CAG | CAT | GCA | AGG | AGG | CCT | 1477 |
| Ile | Cys | Met | Gly | Ser | Ile | Met | His | Pro | Ser | Gln | His | Ala | Arg | Arg | Pro | |
| | 335 | | | | | 340 | | | | | 345 | | | | | |
| GAA | GAC | GTC | CGC | ACA | AAA | GGA | CAG | CTC | TTC | CCT | CTC | GCC | AAA | GAG | TTT | 1525 |
| Glu | Asp | Val | Arg | Thr | Lys | Gly | Gln | Leu | Phe | Pro | Leu | Ala | Lys | Glu | Phe | |
| 350 | | | | | 355 | | | | | 360 | | | | | 365 | |
| ATT | GAT | CAA | TAC | TAT | TCA | TCA | ATT | AAA | AGA | TTT | GGC | TCC | AAA | GCC | CAC | 1573 |
| Ile | Asp | Gln | Tyr | Tyr | Ser | Ser | Ile | Lys | Arg | Phe | Gly | Ser | Lys | Ala | His | |
| | | | | 370 | | | | | 375 | | | | | 380 | | |
| ATG | GAA | AGG | CTG | GAA | GAG | GTG | AAC | AAA | GAG | ATC | GAC | ACC | ACT | AGC | ACT | 1621 |
| Met | Glu | Arg | Leu | Glu | Glu | Val | Asn | Lys | Glu | Ile | Asp | Thr | Thr | Ser | Thr | |
| | | | 385 | | | | | 390 | | | | | 395 | | | |
| TAC | CAG | CTC | AAG | GAC | ACA | GAG | CTC | ATC | TAT | GGG | GCC | AAG | CAC | GCC | TGG | 1669 |
| Tyr | Gln | Leu | Lys | Asp | Thr | Glu | Leu | Ile | Tyr | Gly | Ala | Lys | His | Ala | Trp | |
| | | | 400 | | | | | 405 | | | | | 410 | | | |
| CGG | AAT | GCC | TCG | CGC | TGT | GTG | GGC | AGG | ATC | CAG | TGG | TCC | AAG | CTG | CAG | 1717 |
| Arg | Asn | Ala | Ser | Arg | Cys | Val | Gly | Arg | Ile | Gln | Trp | Ser | Lys | Leu | Gln | |
| | | 415 | | | | | 420 | | | | | 425 | | | | |
| GTA | TTC | GAT | GCC | CGT | GAC | TGC | ACC | ACG | GCC | CAC | GGG | ATG | TTC | AAC | TAC | 1765 |
| Val | Phe | Asp | Ala | Arg | Asp | Cys | Thr | Thr | Ala | His | Gly | Met | Phe | Asn | Tyr | |
| 430 | | | | | 435 | | | | | 440 | | | | | 445 | |
| ATC | TGT | AAC | CAT | GTC | AAG | TAT | GCC | ACC | AAC | AAA | GGG | AAC | CTC | AGG | TCT | 1813 |
| Ile | Cys | Asn | His | Val | Lys | Tyr | Ala | Thr | Asn | Lys | Gly | Asn | Leu | Arg | Ser | |
| | | | | 450 | | | | | 455 | | | | | 460 | | |
| GCC | ATC | ACC | ATA | TTC | CCC | CAG | AGG | ACA | GAC | GGC | AAG | CAC | GAC | TTC | CGA | 1861 |
| Ala | Ile | Thr | Ile | Phe | Pro | Gln | Arg | Thr | Asp | Gly | Lys | His | Asp | Phe | Arg | |
| | | | 465 | | | | | 470 | | | | | 475 | | | |
| GTC | TGG | AAC | TCC | CAG | CTC | ATC | CGC | TAC | GCT | GGC | TAC | AAG | CAC | CGT | GAC | 1909 |
| Val | Trp | Asn | Ser | Gln | Leu | Ile | Arg | Tyr | Ala | Gly | Tyr | Lys | His | Arg | Asp | |
| | | 480 | | | | | 485 | | | | | 490 | | | | |

```
GGC  TCC  ACC  CTG  GGG  GAC  CCA  GCC  AAT  GTG  CAG  TTC  ACA  GAG  ATA  TGC    1957
Gly  Ser  Thr  Leu  Gly  Asp  Pro  Ala  Asn  Val  Gln  Phe  Thr  Glu  Ile  Cys
     495                 500                      505

ATA  CAG  CAG  GGC  TGG  AAA  CCG  CCT  AGA  GGC  CGC  TTC  GAT  GTC  CTG  CCG    2005
Ile  Gln  Gln  Gly  Trp  Lys  Pro  Pro  Arg  Gly  Arg  Phe  Asp  Val  Leu  Pro
510                      515                 520                           525

CTC  CTG  CTT  CAG  GCC  AAC  GGC  AAT  GAC  CCT  GAG  CTC  TTC  CAG  ATT  CCT    2053
Leu  Leu  Leu  Gln  Ala  Asn  Gly  Asn  Asp  Pro  Glu  Leu  Phe  Gln  Ile  Pro
                    530                 535                      540

CCA  GAG  CTG  GTG  TTG  GAA  CTT  CCC  ATC  AGG  CAC  CCC  AAG  TTT  GAG  TGG    2101
Pro  Glu  Leu  Val  Leu  Glu  Leu  Pro  Ile  Arg  His  Pro  Lys  Phe  Glu  Trp
               545                 550                      555

TTC  AAG  GAC  CTG  GCG  CTG  AAG  TGG  TAC  GGC  CTC  CCC  GCC  GTG  TCC  AAC    2149
Phe  Lys  Asp  Leu  Ala  Leu  Lys  Trp  Tyr  Gly  Leu  Pro  Ala  Val  Ser  Asn
               560                 565                      570

ATG  CTC  CTA  GAG  ATT  GGC  GGC  CTG  GAG  TTC  AGC  GCC  TGT  CCC  TTC  AGT    2197
Met  Leu  Leu  Glu  Ile  Gly  Gly  Leu  Glu  Phe  Ser  Ala  Cys  Pro  Phe  Ser
          575                 580                 585

GGC  TGG  TAC  ATG  GGC  ACA  GAG  ATT  GGT  GTC  CGC  GAC  TAC  TGT  GAC  AAC    2245
Gly  Trp  Tyr  Met  Gly  Thr  Glu  Ile  Gly  Val  Arg  Asp  Tyr  Cys  Asp  Asn
590                      595                 600                           605

TCC  CGC  TAC  AAT  ATC  CTG  GAG  GAA  GTG  GCC  AAG  AAG  ATG  AAC  TTA  GAC    2293
Ser  Arg  Tyr  Asn  Ile  Leu  Glu  Glu  Val  Ala  Lys  Lys  Met  Asn  Leu  Asp
                    610                 615                      620

ATG  AGG  AAG  ACG  TCC  TCC  CTG  TGG  AAG  GAC  CAG  GCG  CTG  GTG  GAG  ATC    2341
Met  Arg  Lys  Thr  Ser  Ser  Leu  Trp  Lys  Asp  Gln  Ala  Leu  Val  Glu  Ile
               625                 630                      635

AAT  ATC  GCG  GTT  CTC  TAT  AGC  TTC  CAG  AGT  GAC  AAA  GTG  ACC  ATT  GTT    2389
Asn  Ile  Ala  Val  Leu  Tyr  Ser  Phe  Gln  Ser  Asp  Lys  Val  Thr  Ile  Val
          640                 645                      650

GAC  CAT  CAC  TCC  GCC  ACC  GAG  TCC  TTC  ATT  AAG  CAC  ATG  GAG  AAT  GAG    2437
Asp  His  His  Ser  Ala  Thr  Glu  Ser  Phe  Ile  Lys  His  Met  Glu  Asn  Glu
     655                 660                      665

TAC  CGC  TGC  CGG  GGG  GGC  TGC  CCT  GCC  GAC  TGG  GTG  TGG  ATC  GTG  CCC    2485
Tyr  Arg  Cys  Arg  Gly  Gly  Cys  Pro  Ala  Asp  Trp  Val  Trp  Ile  Val  Pro
670                      675                 680                           685

CCC  ATG  TCC  GGA  AGC  ATC  ACC  CCT  GTG  TTC  CAC  CAG  GAG  ATG  CTC  AAC    2533
Pro  Met  Ser  Gly  Ser  Ile  Thr  Pro  Val  Phe  His  Gln  Glu  Met  Leu  Asn
                    690                 695                      700

TAC  CGG  CTC  ACC  CCC  TCC  TTC  GAA  TAC  CAG  CCT  GAT  CCC  TGG  AAC  ACG    2581
Tyr  Arg  Leu  Thr  Pro  Ser  Phe  Glu  Tyr  Gln  Pro  Asp  Pro  Trp  Asn  Thr
               705                 710                      715

CAT  GTC  TGG  AAA  GGC  ACC  AAC  GGG  ACC  CCC  ACA  AAG  CGG  CGA  GCC  ATC    2629
His  Val  Trp  Lys  Gly  Thr  Asn  Gly  Thr  Pro  Thr  Lys  Arg  Arg  Ala  Ile
          720                 725                      730

GGC  TTC  AAG  AAG  CTA  GCA  GAA  GCT  GTC  AAG  TTC  TCG  GCC  AAG  CTG  ATG    2677
Gly  Phe  Lys  Lys  Leu  Ala  Glu  Ala  Val  Lys  Phe  Ser  Ala  Lys  Leu  Met
     735                 740                      745

GGG  CAG  GCT  ATG  GCC  AAG  AGG  GTG  AAA  GCG  ACC  ATC  CTC  TAT  GCC  ACA    2725
Gly  Gln  Ala  Met  Ala  Lys  Arg  Val  Lys  Ala  Thr  Ile  Leu  Tyr  Ala  Thr
750                      755                 760                           765

GAG  ACA  GGC  AAA  TCG  CAA  GCT  TAT  GCC  AAG  ACC  TTG  TGT  GAG  ATC  TTC    2773
Glu  Thr  Gly  Lys  Ser  Gln  Ala  Tyr  Ala  Lys  Thr  Leu  Cys  Glu  Ile  Phe
                    770                 775                      780

AAA  CAC  GCC  TTT  GAT  GCC  AAG  GTG  ATG  TCC  ATG  GAA  GAA  TAT  GAC  ATT    2821
Lys  His  Ala  Phe  Asp  Ala  Lys  Val  Met  Ser  Met  Glu  Glu  Tyr  Asp  Ile
               785                 790                      795

GTG  CAC  CTG  GAA  CAT  GAA  ACT  CTG  GTC  CTT  GTG  GTC  ACC  AGC  ACC  TTT    2869
Val  His  Leu  Glu  His  Glu  Thr  Leu  Val  Leu  Val  Val  Thr  Ser  Thr  Phe
          800                 805                      810
```

| | | | | | | | | | | | | | | | | |
|---|---|---|---|---|---|---|---|---|---|---|---|---|---|---|---|---|
| GGC | AAT | GGA | GAT | CCC | CCT | GAG | AAT | GGG | GAG | AAA | TTC | GGC | TGT | GCT | TTG | 2917 |
| Gly | Asn 815 | Gly | Asp | Pro | Pro | Glu | Asn 820 | Gly | Glu | Lys | Phe | Gly 825 | Cys | Ala | Leu | |
| ATG | GAA | ATG | AGG | CAC | CCC | AAC | TCT | GTG | CAG | GAA | GAA | AGG | AAG | AGC | TAC | 2965 |
| Met | Glu | Met | Arg 830 | His | Pro | Asn | Ser 835 | Val | Gln | Glu | Glu 840 | Arg | Lys | Ser | Tyr 845 | |
| AAG | GTC | CGA | TTC | AAC | AGC | GTC | TCC | TCC | TAC | TCT | GAC | TCC | CAA | AAA | TCA | 3013 |
| Lys | Val | Arg | Phe | Asn 850 | Ser | Val | Ser | Ser | Tyr 855 | Ser | Asp | Ser | Gln | Lys 860 | Ser | |
| TCA | GGC | GAT | GGG | CCC | GAC | CTC | AGA | GAC | AAC | TTT | GAG | AGT | GCT | GGA | CCC | 3061 |
| Ser | Gly | Asp | Gly 865 | Pro | Asp | Leu | Arg | Asp 870 | Asn | Phe | Glu | Ser | Ala 875 | Gly | Pro | |
| CTG | GCC | AAT | GTG | AGG | TTC | TCA | GTT | TTT | GGC | CTC | GGC | TCA | CGA | GCA | TAC | 3109 |
| Leu | Ala | Asn 880 | Val | Arg | Phe | Ser | Val 885 | Phe | Gly | Leu | Gly | Ser 890 | Arg | Ala | Tyr | |
| CCT | CAC | TTT | TGC | GCC | TTC | GGA | CAC | GCT | GTG | GAC | ACC | CTC | CTG | GAA | GAA | 3157 |
| Pro | His 895 | Phe | Cys | Ala | Phe | Gly | His 900 | Ala | Val | Asp | Thr | Leu 905 | Leu | Glu | Glu | |
| CTG | GGA | GGG | GAG | AGG | ATC | CTG | AAG | ATG | AGG | GAA | GGG | GAT | GAG | CTC | TGT | 3205 |
| Leu 910 | Gly | Gly | Glu | Arg | Ile 915 | Leu | Lys | Met | Arg | Glu 920 | Gly | Asp | Glu | Leu | Cys 925 | |
| GGG | CAG | GAA | GAG | GCT | TTC | AGG | ACC | TGG | GCC | AAG | AAG | GTC | TTC | AAG | GCA | 3253 |
| Gly | Gln | Glu | Glu | Ala 930 | Phe | Arg | Thr | Trp | Ala 935 | Lys | Lys | Val | Phe | Lys 940 | Ala | |
| GCC | TGT | GAT | GTC | TTC | TGT | GTG | GGA | GAT | GAT | GTC | AAC | ATT | GAA | AAG | GCC | 3301 |
| Ala | Cys | Asp | Val 945 | Phe | Cys | Val | Gly | Asp 950 | Asp | Val | Asn | Ile | Glu 955 | Lys | Ala | |
| AAC | AAT | TCC | CTC | ATC | AGC | AAT | GAT | CGC | AGC | TGG | AAG | AGA | AAC | AAG | TTC | 3349 |
| Asn | Asn | Ser 960 | Leu | Ile | Ser | Asn | Asp 965 | Arg | Ser | Trp | Lys | Arg 970 | Asn | Lys | Phe | |
| CGC | CTC | ACC | TTT | GTG | GCC | GAA | GCT | CCA | GAA | CTC | ACA | CAA | GGT | CTA | TCC | 3397 |
| Arg | Leu | Thr 975 | Phe | Val | Ala | Glu | Ala 980 | Pro | Glu | Leu | Thr | Gln 985 | Gly | Leu | Ser | |
| AAT | GTC | CAC | AAA | AAG | CGA | GTC | TCA | GCT | GCC | CGG | CTC | CTT | AGC | CGT | CAA | 3445 |
| Asn 990 | Val | His | Lys | Lys | Arg 995 | Val | Ser | Ala | Ala | Arg 1000 | Leu | Leu | Ser | Arg | Gln 1005 | |
| AAC | CTC | CAG | AGC | CCT | AAA | TCC | AGT | CGG | TCA | ACT | ATC | TTC | GTG | CGT | CTC | 3493 |
| Asn | Leu | Gln | Ser | Pro 1010 | Lys | Ser | Ser | Arg | Ser 1015 | Thr | Ile | Phe | Val | Arg 1020 | Leu | |
| CAC | ACC | AAC | GGG | AGC | CAG | GAG | CTG | CAG | TAC | CAG | CCT | GGG | GAC | CAC | CTG | 3541 |
| His | Thr | Asn | Gly | Ser 1025 | Gln | Glu | Leu | Gln | Tyr 1030 | Gln | Pro | Gly | Asp | His 1035 | Leu | |
| GGT | GTC | TTC | CCT | GGC | AAC | CAC | GAG | GAC | CTC | GTG | AAT | GCC | CTG | ATC | GAG | 3589 |
| Gly | Val | Phe | Pro 1040 | Gly | Asn | His | Glu | Asp 1045 | Leu | Val | Asn | Ala | Leu 1050 | Ile | Glu | |
| CGG | CTG | GAG | GAC | GCG | CCG | CCT | GTC | AAC | CAG | ATG | GTG | AAA | GTG | GAA | CTG | 3637 |
| Arg | Leu 1055 | Glu | Asp | Ala | Pro | Pro 1060 | Val | Asn | Gln | Met | Val 1065 | Lys | Val | Glu | Leu | |
| CTG | GAG | GAG | CGG | AAC | ACG | GCT | TTA | GGT | GTC | ATC | AGT | AAC | TGG | ACA | GAC | 3685 |
| Leu 1070 | Glu | Glu | Arg | Asn | Thr 1075 | Ala | Leu | Gly | Val | Ile 1080 | Ser | Asn | Trp | Thr | Asp 1085 | |
| GAG | CTC | CGC | CTC | CCG | CCC | TGC | ACC | ATC | TTC | CAG | GCC | TTC | AAG | TAC | TAC | 3733 |
| Glu | Leu | Arg | Leu | Pro 1090 | Pro | Cys | Thr | Ile | Phe 1095 | Gln | Ala | Phe | Lys | Tyr 1100 | Tyr | |
| CTG | GAC | ATC | ACC | ACG | CCA | CCA | ACG | CCT | CTG | CAG | CTG | CAG | CAG | TTT | GCC | 3781 |
| Leu | Asp | Ile | Thr | Thr 1105 | Pro | Pro | Thr | Pro | Leu 1110 | Gln | Leu | Gln | Gln | Phe 1115 | Ala | |
| TCC | CTA | GCT | ACC | AGC | GAG | AAG | GAG | AAG | CAG | CGT | CTG | CTG | GTC | CTC | AGC | 3829 |
| Ser | Leu | Ala 1120 | Thr | Ser | Glu | Lys | Glu 1125 | Lys | Gln | Arg | Leu | Leu 1130 | Val | Leu | Ser | |

| | | | | | | | | | | | | | | | | |
|---|---|---|---|---|---|---|---|---|---|---|---|---|---|---|---|---|
| AAG | GGT | TTG | CAG | GAG | TAC | GAG | GAA | TGG | AAA | TGG | GGC | AAG | AAC | CCC | ACC | 3877 |
| Lys | Gly | Leu | Gln | Glu | Tyr | Glu | Glu | Trp | Lys | Trp | Gly | Lys | Asn | Pro | Thr | |
| | | | | 1135 | | | | 1140 | | | | 1145 | | | | |
| ATC | GTG | GAG | GTG | CTG | GAG | GAG | TTC | CCA | TCT | ATC | CAG | ATG | CCG | GCC | ACC | 3925 |
| Ile | Val | Glu | Val | Leu | Glu | Glu | Phe | Pro | Ser | Ile | Gln | Met | Pro | Ala | Thr | |
| 1150 | | | | | 1155 | | | | | 1160 | | | | | 1165 | |
| CTG | CTC | CTG | ACC | CAG | CTG | TCC | CTG | CTG | CAG | CCC | CGC | TAC | TAT | TCC | ATC | 3973 |
| Leu | Leu | Leu | Thr | Gln | Leu | Ser | Leu | Leu | Gln | Pro | Arg | Tyr | Tyr | Ser | Ile | |
| | | | | 1170 | | | | | 1175 | | | | | 1180 | | |
| AGC | TCC | TCC | CCA | GAC | ATG | TAC | CCT | GAT | GAA | GTG | CAC | CTC | ACT | GTG | GCC | 4021 |
| Ser | Ser | Ser | Pro | Asp | Met | Tyr | Pro | Asp | Glu | Val | His | Leu | Thr | Val | Ala | |
| | | | 1185 | | | | 1190 | | | | | 1195 | | | | |
| ATC | GTT | TCC | TAC | CGC | ACT | CGA | GAT | GGA | GAA | GGA | CCA | ATT | CAC | CAC | GGC | 4069 |
| Ile | Val | Ser | Tyr | Arg | Thr | Arg | Asp | Gly | Glu | Gly | Pro | Ile | His | His | Gly | |
| | | 1200 | | | | | 1205 | | | | | 1210 | | | | |
| GTA | TGC | TCC | TCC | TGG | CTC | AAC | CGG | ATA | CAG | GCT | GAC | GAA | CTG | GTC | CCC | 4117 |
| Val | Cys | Ser | Ser | Trp | Leu | Asn | Arg | Ile | Gln | Ala | Asp | Glu | Leu | Val | Pro | |
| | 1215 | | | | | 1220 | | | | | 1225 | | | | | |
| TGT | TTC | GTG | AGA | GGA | GCA | CCC | AGC | TTC | CAC | CTG | CCC | CGG | AAC | CCC | CAA | 4165 |
| Cys | Phe | Val | Arg | Gly | Ala | Pro | Ser | Phe | His | Leu | Pro | Arg | Asn | Pro | Gln | |
| 1230 | | | | | 1235 | | | | | 1240 | | | | | 1245 | |
| GTC | CCC | TGC | ATC | CTC | GTT | GGA | CCA | GGC | ACC | GGC | ATT | GCC | CCT | TTC | CGA | 4213 |
| Val | Pro | Cys | Ile | Leu | Val | Gly | Pro | Gly | Thr | Gly | Ile | Ala | Pro | Phe | Arg | |
| | | | | 1250 | | | | | 1255 | | | | | 1260 | | |
| AGC | TTC | TGG | CAA | CAG | CGG | CAA | TTT | GAT | ATC | CAA | CAC | AAA | GGA | ATG | AAC | 4261 |
| Ser | Phe | Trp | Gln | Gln | Arg | Gln | Phe | Asp | Ile | Gln | His | Lys | Gly | Met | Asn | |
| | | | 1265 | | | | | 1270 | | | | | 1275 | | | |
| CCC | TGC | CCC | ATG | GTC | CTG | GTC | TTC | GGG | TGC | CGG | CAA | TCC | AAG | ATA | GAT | 4309 |
| Pro | Cys | Pro | Met | Val | Leu | Val | Phe | Gly | Cys | Arg | Gln | Ser | Lys | Ile | Asp | |
| | | 1280 | | | | | 1285 | | | | | 1290 | | | | |
| CAT | ATC | TAC | AGG | GAA | GAG | ACC | CTG | CAG | GCC | AAG | AAC | AAG | GGG | GTC | TTC | 4357 |
| His | Ile | Tyr | Arg | Glu | Glu | Thr | Leu | Gln | Ala | Lys | Asn | Lys | Gly | Val | Phe | |
| | 1295 | | | | | 1300 | | | | | 1305 | | | | | |
| AGA | GAG | CTG | TAC | ACG | GCT | TAC | TCC | CGG | GAG | CCA | GAC | AAA | CCA | AAG | AAG | 4405 |
| Arg | Glu | Leu | Tyr | Thr | Ala | Tyr | Ser | Arg | Glu | Pro | Asp | Lys | Pro | Lys | Lys | |
| 1310 | | | | | 1315 | | | | | 1320 | | | | | 1325 | |
| TAC | GTG | CAG | GAC | ATC | CTG | CAG | GAG | CAG | CTG | GCG | GAG | TCT | GTG | TAC | CGA | 4453 |
| Tyr | Val | Gln | Asp | Ile | Leu | Gln | Glu | Gln | Leu | Ala | Glu | Ser | Val | Tyr | Arg | |
| | | | | 1330 | | | | | 1335 | | | | | 1340 | | |
| GCC | CTG | AAG | GAG | CAA | GGG | GGC | CAC | ATA | TAC | GTC | TGT | GGG | GAC | GTC | ACC | 4501 |
| Ala | Leu | Lys | Glu | Gln | Gly | Gly | His | Ile | Tyr | Val | Cys | Gly | Asp | Val | Thr | |
| | | | | 1345 | | | | | 1350 | | | | | 1355 | | |
| ATG | GCT | GCT | GAT | GTC | CTC | AAA | GCC | ATC | CAG | CGC | ATC | ATG | ACC | CAG | CAG | 4549 |
| Met | Ala | Ala | Asp | Val | Leu | Lys | Ala | Ile | Gln | Arg | Ile | Met | Thr | Gln | Gln | |
| | | | 1360 | | | | | 1365 | | | | | 1370 | | | |
| GGG | AAG | CTC | TCG | GCA | GAG | GAC | GCC | GGC | GTA | TTC | ATC | AGC | CGG | ATG | AGG | 4597 |
| Gly | Lys | Leu | Ser | Ala | Glu | Asp | Ala | Gly | Val | Phe | Ile | Ser | Arg | Met | Arg | |
| | | 1375 | | | | | 1380 | | | | | 1385 | | | | |
| GAT | GAC | AAC | CGA | TAC | CAT | GAG | GAT | ATT | TTT | GGA | GTC | ACC | CTG | CGA | ACG | 4645 |
| Asp | Asp | Asn | Arg | Tyr | His | Glu | Asp | Ile | Phe | Gly | Val | Thr | Leu | Arg | Thr | |
| 1390 | | | | | 1395 | | | | | 1400 | | | | | 1405 | |
| ATC | GAA | GTG | ACC | AAC | CGC | CTT | AGA | TCT | GAG | TCC | ATT | GCC | TTC | ATT | GAA | 4693 |
| Ile | Glu | Val | Thr | Asn | Arg | Leu | Arg | Ser | Glu | Ser | Ile | Ala | Phe | Ile | Glu | |
| | | | | 1410 | | | | | 1415 | | | | | 1420 | | |
| GAG | AGC | AAA | AAA | GAC | ACC | GAT | GAG | GTT | TTC | AGC | TCC | TAACTGGACC | | | | 4739 |
| Glu | Ser | Lys | Lys | Asp | Thr | Asp | Glu | Val | Phe | Ser | Ser | | | | | |
| | | | | 1425 | | | | | 1430 | | | | | | | |

| | | | | |
|---|---|---|---|---|
| CTCTTGCCCA | GCCGGCTGCA | AGTTTGTAAG | CGCGGGACAG | A | 4780 |

(2) INFORMATION FOR SEQ ID NO:21:

(i) SEQUENCE CHARACTERISTICS:
        (A) LENGTH: 1433 amino acids
        (B) TYPE: amino acid
        (D) TOPOLOGY: linear (ii) MOLECULE TYPE: protein (xi) SEQUENCE DESCRIPTION: SEQ ID NO:21:

```
Met Glu Asp His Met Phe Gly Val Gln Gln Ile Gln Pro Asn Val Ile
 1               5                  10                  15
Ser Val Arg Leu Phe Lys Arg Lys Val Gly Gly Leu Gly Phe Leu Val
            20                  25                  30
Lys Glu Arg Val Ser Lys Pro Pro Val Ile Ile Ser Asp Leu Ile Arg
            35                  40                  45
Gly Gly Ala Ala Glu Gln Ser Gly Leu Ile Gln Ala Gly Asp Ile Ile
        50                  55                  60
Leu Ala Val Asn Gly Arg Pro Leu Val Asp Leu Ser Tyr Asp Ser Ala
 65                 70                  75                  80
Leu Glu Val Leu Arg Gly Ile Ala Ser Glu Thr His Val Val Leu Ile
                85                  90                  95
Leu Arg Gly Pro Glu Gly Phe Thr Thr His Leu Glu Thr Thr Phe Thr
            100                 105                 110
Gly Asp Gly Thr Pro Lys Thr Ile Arg Val Thr Gln Pro Leu Gly Pro
            115                 120                 125
Pro Thr Lys Ala Val Asp Leu Ser His Gln Pro Pro Ala Gly Lys Glu
        130                 135                 140
Gln Pro Leu Ala Val Asp Gly Ala Ser Gly Pro Gly Asn Gly Pro Gln
145                 150                 155                 160
His Ala Tyr Asp Asp Gly Gln Glu Ala Gly Ser Leu Pro His Ala Asn
                165                 170                 175
Gly Trp Pro Gln Ala Pro Arg Gln Asp Pro Ala Lys Lys Ala Thr Arg
            180                 185                 190
Val Ser Leu Gln Gly Arg Gly Glu Asn Asn Glu Leu Leu Lys Glu Ile
            195                 200                 205
Glu Pro Val Leu Ser Leu Leu Thr Ser Gly Ser Arg Gly Val Lys Gly
        210                 215                 220
Gly Ala Pro Ala Lys Ala Glu Met Lys Asp Met Gly Ile Gln Val Asp
225                 230                 235                 240
Arg Asp Leu Asp Gly Lys Ser His Lys Pro Leu Pro Leu Gly Val Glu
                245                 250                 255
Asn Asp Arg Val Phe Asn Asp Leu Trp Gly Lys Gly Asn Val Pro Val
            260                 265                 270
Val Leu Asn Asn Pro Tyr Ser Glu Lys Glu Gln Pro Pro Thr Ser Gly
            275                 280                 285
Lys Gln Ser Pro Thr Lys Asn Gly Ser Pro Ser Lys Cys Pro Arg Phe
        290                 295                 300
Leu Lys Val Lys Asn Trp Glu Thr Glu Val Val Leu Thr Asp Thr Leu
305                 310                 315                 320
His Leu Lys Ser Thr Leu Glu Thr Gly Cys Thr Glu Tyr Ile Cys Met
                325                 330                 335
Gly Ser Ile Met His Pro Ser Gln His Ala Arg Arg Pro Glu Asp Val
            340                 345                 350
Arg Thr Lys Gly Gln Leu Phe Pro Leu Ala Lys Glu Phe Ile Asp Gln
            355                 360                 365
```

| Tyr | Tyr | Ser | Ser | Ile | Lys | Arg | Phe | Gly | Ser | Lys | Ala | His | Met | Glu | Arg |
|---|---|---|---|---|---|---|---|---|---|---|---|---|---|---|---|
| | 370 | | | | 375 | | | | | 380 | | | | | |

Leu Glu Glu Val Asn Lys Glu Ile Asp Thr Thr Ser Thr Tyr Gln Leu
385              390              395              400

Lys Asp Thr Glu Leu Ile Tyr Gly Ala Lys His Ala Trp Arg Asn Ala
                405              410                   415

Ser Arg Cys Val Gly Arg Ile Gln Trp Ser Lys Leu Gln Val Phe Asp
              420              425              430

Ala Arg Asp Cys Thr Thr Ala His Gly Met Phe Asn Tyr Ile Cys Asn
          435              440              445

His Val Lys Tyr Ala Thr Asn Lys Gly Asn Leu Arg Ser Ala Ile Thr
    450              455              460

Ile Phe Pro Gln Arg Thr Asp Gly Lys His Asp Phe Arg Val Trp Asn
465              470              475              480

Ser Gln Leu Ile Arg Tyr Ala Gly Tyr Lys His Arg Asp Gly Ser Thr
              485              490              495

Leu Gly Asp Pro Ala Asn Val Gln Phe Thr Glu Ile Cys Ile Gln Gln
          500              505              510

Gly Trp Lys Pro Pro Arg Gly Arg Phe Asp Val Leu Pro Leu Leu Leu
        515              520              525

Gln Ala Asn Gly Asn Asp Pro Glu Leu Phe Gln Ile Pro Pro Glu Leu
    530              535              540

Val Leu Glu Leu Pro Ile Arg His Pro Lys Phe Glu Trp Phe Lys Asp
545              550              555              560

Leu Ala Leu Lys Trp Tyr Gly Leu Pro Ala Val Ser Asn Met Leu Leu
              565              570              575

Glu Ile Gly Gly Leu Glu Phe Ser Ala Cys Pro Phe Ser Gly Trp Tyr
          580              585              590

Met Gly Thr Glu Ile Gly Val Arg Asp Tyr Cys Asp Asn Ser Arg Tyr
        595              600              605

Asn Ile Leu Glu Glu Val Ala Lys Lys Met Asn Leu Asp Met Arg Lys
    610              615              620

Thr Ser Ser Leu Trp Lys Asp Gln Ala Leu Val Glu Ile Asn Ile Ala
625              630              635              640

Val Leu Tyr Ser Phe Gln Ser Asp Lys Val Thr Ile Val Asp His His
              645              650              655

Ser Ala Thr Glu Ser Phe Ile Lys His Met Glu Asn Glu Tyr Arg Cys
          660              665              670

Arg Gly Gly Cys Pro Ala Asp Trp Val Trp Ile Val Pro Pro Met Ser
        675              680              685

Gly Ser Ile Thr Pro Val Phe His Gln Glu Met Leu Asn Tyr Arg Leu
    690              695              700

Thr Pro Ser Phe Glu Tyr Gln Pro Asp Pro Trp Asn Thr His Val Trp
705              710              715              720

Lys Gly Thr Asn Gly Thr Pro Thr Lys Arg Arg Ala Ile Gly Phe Lys
              725              730              735

Lys Leu Ala Glu Ala Val Lys Phe Ser Ala Lys Leu Met Gly Gln Ala
          740              745              750

Met Ala Lys Arg Val Lys Ala Thr Ile Leu Tyr Ala Thr Glu Thr Gly
        755              760              765

Lys Ser Gln Ala Tyr Ala Lys Thr Leu Cys Glu Ile Phe Lys His Ala
    770              775              780

Phe Asp Ala Lys Val Met Ser Met Glu Glu Tyr Asp Ile Val His Leu
785              790              795              800

```
Glu His Glu Thr Leu Val Leu Val Val Thr Ser Thr Phe Gly Asn Gly
            805                     810                     815

Asp Pro Pro Glu Asn Gly Glu Lys Phe Gly Cys Ala Leu Met Glu Met
            820                     825                     830

Arg His Pro Asn Ser Val Gln Glu Arg Lys Ser Tyr Lys Val Arg
            835                     840                     845

Phe Asn Ser Val Ser Ser Tyr Ser Asp Ser Gln Lys Ser Ser Gly Asp
        850                     855                     860

Gly Pro Asp Leu Arg Asp Asn Phe Glu Ser Ala Gly Pro Leu Ala Asn
865                     870                     875                 880

Val Arg Phe Ser Val Phe Gly Leu Gly Ser Arg Ala Tyr Pro His Phe
                885                     890                     895

Cys Ala Phe Gly His Ala Val Asp Thr Leu Leu Glu Glu Leu Gly Gly
            900                     905                     910

Glu Arg Ile Leu Lys Met Arg Glu Gly Asp Glu Leu Cys Gly Gln Glu
            915                     920                     925

Glu Ala Phe Arg Thr Trp Ala Lys Lys Val Phe Lys Ala Ala Cys Asp
930                     935                     940

Val Phe Cys Val Gly Asp Asp Val Asn Ile Glu Lys Ala Asn Asn Ser
945                     950                     955                 960

Leu Ile Ser Asn Asp Arg Ser Trp Lys Arg Asn Lys Phe Arg Leu Thr
                965                     970                     975

Phe Val Ala Glu Ala Pro Glu Leu Thr Gln Gly Leu Ser Asn Val His
            980                     985                     990

Lys Lys Arg Val Ser Ala Ala Arg Leu Leu Ser Arg Gln Asn Leu Gln
            995                     1000                    1005

Ser Pro Lys Ser Ser Arg Ser Thr Ile Phe Val Arg Leu His Thr Asn
        1010                    1015                    1020

Gly Ser Gln Glu Leu Gln Tyr Gln Pro Gly Asp His Leu Gly Val Phe
1025                    1030                    1035                1040

Pro Gly Asn His Glu Asp Leu Val Asn Ala Leu Ile Glu Arg Leu Glu
                1045                    1050                    1055

Asp Ala Pro Pro Val Asn Gln Met Val Lys Val Glu Leu Leu Glu Glu
            1060                    1065                    1070

Arg Asn Thr Ala Leu Gly Val Ile Ser Asn Trp Thr Asp Glu Leu Arg
            1075                    1080                    1085

Leu Pro Pro Cys Thr Ile Phe Gln Ala Phe Lys Tyr Tyr Leu Asp Ile
        1090                    1095                    1100

Thr Thr Pro Pro Thr Pro Leu Gln Leu Gln Gln Phe Ala Ser Leu Ala
1105                    1110                    1115                1120

Thr Ser Glu Lys Glu Lys Gln Arg Leu Leu Val Leu Ser Lys Gly Leu
            1125                    1130                    1135

Gln Glu Tyr Glu Glu Trp Lys Trp Gly Lys Asn Pro Thr Ile Val Glu
            1140                    1145                    1150

Val Leu Glu Glu Phe Pro Ser Ile Gln Met Pro Ala Thr Leu Leu Leu
            1155                    1160                    1165

Thr Gln Leu Ser Leu Leu Gln Pro Arg Tyr Tyr Ser Ile Ser Ser Ser
        1170                    1175                    1180

Pro Asp Met Tyr Pro Asp Glu Val His Leu Thr Val Ala Ile Val Ser
1185                    1190                    1195                1200

Tyr Arg Thr Arg Asp Gly Glu Gly Pro Ile His His Gly Val Cys Ser
                1205                    1210                    1215

Ser Trp Leu Asn Arg Ile Gln Ala Asp Glu Leu Val Pro Cys Phe Val
```

|   |   |   | 1220 |   |   |   |   |   | 1225 |   |   |   |   | 1230 |   |   |
|---|---|---|------|---|---|---|---|---|------|---|---|---|---|------|---|---|
| Arg | Gly | Ala | Pro | Ser | Phe | His | Leu | Pro | Arg | Asn | Pro | Gln | Val | Pro | Cys |   |
|   |   |   | 1235 |   |   |   | 1240 |   |   |   |   | 1245 |   |   |   |   |

Ile Leu Val Gly Pro Gly Thr Gly Ile Ala Pro Phe Arg Ser Phe Trp
    1250              1255              1260

Gln Gln Arg Gln Phe Asp Ile Gln His Lys Gly Met Asn Pro Cys Pro
1265              1270              1275              1280

Met Val Leu Val Phe Gly Cys Arg Gln Ser Lys Ile Asp His Ile Tyr
            1285              1290              1295

Arg Glu Glu Thr Leu Gln Ala Lys Asn Lys Gly Val Phe Arg Glu Leu
            1300              1305              1310

Tyr Thr Ala Tyr Ser Arg Glu Pro Asp Lys Pro Lys Lys Tyr Val Gln
        1315              1320              1325

Asp Ile Leu Gln Glu Gln Leu Ala Glu Ser Val Tyr Arg Ala Leu Lys
        1330              1335              1340

Glu Gln Gly Gly His Ile Tyr Val Cys Gly Asp Val Thr Met Ala Ala
1345              1350              1355              1360

Asp Val Leu Lys Ala Ile Gln Arg Ile Met Thr Gln Gln Gly Lys Leu
                1365              1370              1375

Ser Ala Glu Asp Ala Gly Val Phe Ile Ser Arg Met Arg Asp Asp Asn
            1380              1385              1390

Arg Tyr His Glu Asp Ile Phe Gly Val Thr Leu Arg Thr Ile Glu Val
            1395              1400              1405

Thr Asn Arg Leu Arg Ser Glu Ser Ile Ala Phe Ile Glu Glu Ser Lys
        1410              1415              1420

Lys Asp Thr Asp Glu Val Phe Ser Ser
1425              1430

( 2 ) INFORMATION FOR SEQ ID NO:22:

( i ) SEQUENCE CHARACTERISTICS:
        ( A ) LENGTH: 256 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( C ) INDIVIDUAL ISOLATE: EPO-1 HRE element ( x i ) SEQUENCE DESCRIPTION: SEQ ID NO:22:

| GAACTGAAAC | CACCAATATG | ACTCTTGGCT | TTTCTGTTTT | CTGGGAACCT | CCAAATCCCC | 60 |
| TGGCTCTGTC | CCACTCCTGG | CAGCAGTGCA | GCAGGTCCAG | GTCCGGGAAA | TGAGGGGTGG | 120 |
| AGGGGGCTGG | GCCCTACGTG | CTGTCTCACA | CAGCCTGTCT | GACCTCTCGA | CCTACCGGCC | 180 |
| TAGGCCACAA | GCTCTGCCTA | CGCTGGTCAA | TAAGGTGTCT | CCATTCAAGG | CCTCACCGCA | 240 |
| GTAAGGCAGC | TGCCAA |   |   |   |   | 256 |

( 2 ) INFORMATION FOR SEQ ID NO:23:

( i ) SEQUENCE CHARACTERISTICS:
        ( A ) LENGTH: 42 base pairs
        ( B ) TYPE: nucleic acid
        ( C ) STRANDEDNESS: double
        ( D ) TOPOLOGY: linear (ii) MOLECULE TYPE: DNA (genomic)

(iii) HYPOTHETICAL: NO (iv) ANTI-SENSE: NO (vi) ORIGINAL SOURCE:
  (C) INDIVIDUAL ISOLATE: 42 bp EPO 3'hypoxia response
    enhancer element (Madan, et al, PNAS 90:3928, 1993)

(xi) SEQUENCE DESCRIPTION: SEQ ID NO:23:

```
GGGCCCTACG TGCTGTCTCA CACAGCCTGT CTGACCTCTC GA                          42
```

(2) INFORMATION FOR SEQ ID NO:24:

(i) SEQUENCE CHARACTERISTICS:
    (A) LENGTH: 86 base pairs
    (B) TYPE: nucleic acid
    (C) STRANDEDNESS: double
    (D) TOPOLOGY: linear (ii) MOLECULE TYPE: DNA (genomic)

(iii) HYPOTHETICAL: NO (iv) ANTI-SENSE: NO (vi) ORIGINAL SOURCE:
    (C) INDIVIDUAL ISOLATE: 86 nucleotide fragment from
      αMHC promoter (xi) SEQUENCE DESCRIPTION: SEQ ID NO:24:

```
GTCCCAGCAG ATGACTCCAA ATTTAGGCAG CAGGCACGTG AATGAGCTA TAAAGGGGCT         60
GGAGCGCTGA GAGCTGTCAG ACCGAG                                            86
```

(2) INFORMATION FOR SEQ ID NO:25:

(i) SEQUENCE CHARACTERISTICS:
    (A) LENGTH: 2423 base pairs
    (B) TYPE: nucleic acid
    (C) STRANDEDNESS: double
    (D) TOPOLOGY: unknown (ii) MOLECULE TYPE: cDNA to mRNA (iii) HYPOTHETICAL: NO (iv) ANTI-SENSE: NO (vi) ORIGINAL SOURCE:
    (C) INDIVIDUAL ISOLATE: mouse catalase gene GenBank #L25069

(ix) FEATURE:
    (A) NAME/KEY: CDS
    (B) LOCATION: 88..1671

(xi) SEQUENCE DESCRIPTION: SEQ ID NO:25:

```
ATTGCCTTCT CCGGGTGGAG ACCAGACCGC TGCGTCCGTC CCTGCTGTCT CACGTTCCGC         60

AGCTCTGCAG CTCCGCAATC CTACACC ATG TCG GAC AGT CGG GAC CCA GCC           111
                              Met Ser Asp Ser Arg Asp Pro Ala
                                1                 5

AGC GAC CAG ATG AAG CAG TGG AAG GAG CAG CGG GCC TCG CAG AGA CCT         159
Ser Asp Gln Met Lys Gln Trp Lys Glu Gln Arg Ala Ser Gln Arg Pro
     10              15                  20

GAT GTC CTG ACC ACC GGA GGC GGG AAC CCA ATA GGA GAT AAA CTT AAT         207
Asp Val Leu Thr Thr Gly Gly Gly Asn Pro Ile Gly Asp Lys Leu Asn
 25              30                  35                      40

ATC ATG ACC GCG GGG TCC CGA GGG CCC CTC CTC GTT CAG GAT GTG GTT         255
Ile Met Thr Ala Gly Ser Arg Gly Pro Leu Leu Val Gln Asp Val Val
             45                  50                  55
```

```
TTC  ACT  GAC  GAG  ATG  GCA  CAC  TTT  GAC  AGA  GAG  CGG  ATT  CCT  GAG  AGA      303
Phe  Thr  Asp  Glu  Met  Ala  His  Phe  Asp  Arg  Glu  Arg  Ile  Pro  Glu  Arg
               60                  65                       70

GTG  GTA  CAC  GCA  AAA  GGA  GCA  GGT  GCT  TTT  GGA  TAC  TTT  GAG  GTC  ACC      351
Val  Val  His  Ala  Lys  Gly  Ala  Gly  Ala  Phe  Gly  Tyr  Phe  Glu  Val  Thr
                    75                  80                       85

CAC  GAT  ATC  ACC  AGA  TAC  TCC  AAG  GGA  AAG  GTG  TTT  GAG  CAT  ATT  GGA      399
His  Asp  Ile  Thr  Arg  Tyr  Ser  Lys  Gly  Lys  Val  Phe  Glu  His  Ile  Gly
               90                  95                       100

AAG  AGG  ACC  CCT  ATT  GCC  GTT  CGG  TTC  TCC  ACA  GTC  GCT  GGA  GAG  TCA      447
Lys  Arg  Thr  Pro  Ile  Ala  Val  Arg  Phe  Ser  Thr  Val  Ala  Gly  Glu  Ser
105                      110                 115                           120

GGC  TCA  GCT  GAC  ACA  GTT  CGT  GAC  CCT  CGG  GGG  TTT  GCA  GTG  AAA  TTT      495
Gly  Ser  Ala  Asp  Thr  Val  Arg  Asp  Pro  Arg  Gly  Phe  Ala  Val  Lys  Phe
                    125                           130                     135

TAC  ACT  GAA  GAT  GGT  AAC  TGG  GAT  CTT  GTG  GGA  AAC  AAC  ACC  CCT  ATT      543
Tyr  Thr  Glu  Asp  Gly  Asn  Trp  Asp  Leu  Val  Gly  Asn  Asn  Thr  Pro  Ile
               140                      145                      150

TTC  TTC  ATC  AGG  GAT  GCC  ATA  TTG  TTT  CCA  TCC  TTT  ATC  CAT  AGC  CAG      591
Phe  Phe  Ile  Arg  Asp  Ala  Ile  Leu  Phe  Pro  Ser  Phe  Ile  His  Ser  Gln
          155                      160                      165

AAG  AGA  AAC  CCA  CAG  ACT  CAC  CTG  AAG  GAT  CCT  GAC  ATG  GTC  TGG  GAC      639
Lys  Arg  Asn  Pro  Gln  Thr  His  Leu  Lys  Asp  Pro  Asp  Met  Val  Trp  Asp
170                           175                      180

TTC  TGG  AGT  CTT  CGT  CCC  GAG  TCT  CTC  CAT  CAG  GTT  TCT  TTC  TTG  TTC      687
Phe  Trp  Ser  Leu  Arg  Pro  Glu  Ser  Leu  His  Gln  Val  Ser  Phe  Leu  Phe
185                      190                      195                     200

AGT  GAC  CGA  GGG  ATT  CCC  GAT  GGT  CAC  CGG  CAC  ATG  AAT  GGC  TAT  GGA      735
Ser  Asp  Arg  Gly  Ile  Pro  Asp  Gly  His  Arg  His  Met  Asn  Gly  Tyr  Gly
                    205                      210                     215

TCA  CAC  ACC  TTC  AAG  TTG  GTT  AAT  GCA  GAT  GGA  GAG  GCA  GTC  TAT  TGC      783
Ser  His  Thr  Phe  Lys  Leu  Val  Asn  Ala  Asp  Gly  Glu  Ala  Val  Tyr  Cys
               220                      225                     230

AAG  TTC  CAT  TAC  AAG  ACC  GAC  CAG  GGC  ATC  AAA  AAC  TTG  CCT  GTT  GGA      831
Lys  Phe  His  Tyr  Lys  Thr  Asp  Gln  Gly  Ile  Lys  Asn  Leu  Pro  Val  Gly
          235                      240                     245

GAG  GCA  GGA  AGG  CTT  GCT  CAG  GAA  GAT  CCG  GAT  TAT  GGC  CTC  CGA  GAT      879
Glu  Ala  Gly  Arg  Leu  Ala  Gln  Glu  Asp  Pro  Asp  Tyr  Gly  Leu  Arg  Asp
250                      255                      260

CTT  TTC  AAT  GCC  ATC  GCC  AAT  GGC  AAT  TAC  CCG  TCC  TGG  ACG  TTT  TAC      927
Leu  Phe  Asn  Ala  Ile  Ala  Asn  Gly  Asn  Tyr  Pro  Ser  Trp  Thr  Phe  Tyr
265                      270                      275                     280

ATC  CAG  GTC  ATG  ACT  TTT  AAG  GAG  GCA  GAA  ACT  TTC  CCA  TTT  AAT  CCA      975
Ile  Gln  Val  Met  Thr  Phe  Lys  Glu  Ala  Glu  Thr  Phe  Pro  Phe  Asn  Pro
                    285                      290                     295

TTT  GAT  CTG  ACC  AAG  GTT  TGG  CCT  CAC  AAG  GAC  TAC  CCT  CTT  ATA  CCA      1023
Phe  Asp  Leu  Thr  Lys  Val  Trp  Pro  His  Lys  Asp  Tyr  Pro  Leu  Ile  Pro
               300                      305                     310

GTT  GGC  AAA  GTG  GTT  TTA  AAC  AAA  AAT  CCA  GTT  AAT  TAC  TTT  GCT  GAA      1071
Val  Gly  Lys  Val  Val  Leu  Asn  Lys  Asn  Pro  Val  Asn  Tyr  Phe  Ala  Glu
          315                      320                     325

GTT  GAA  CAG  ATG  GCT  TTT  GAC  CCA  AGC  AAT  ATG  CCC  CCT  GGC  ATC  GAG      1119
Val  Glu  Gln  Met  Ala  Phe  Asp  Pro  Ser  Asn  Met  Pro  Pro  Gly  Ile  Glu
330                      335                      340

CCC  AGC  CCT  GAC  AAA  AAG  CTT  CAG  GGC  CGC  CTT  TTT  GCC  TAC  CCG  GAC      1167
Pro  Ser  Pro  Asp  Lys  Lys  Leu  Gln  Gly  Arg  Leu  Phe  Ala  Tyr  Pro  Asp
345                      350                      355                     360

ACT  CAC  CGC  CAC  CGC  CTG  GGA  CCC  AAC  TAT  CTG  CAG  ATA  CCT  GTG  AAC      1215
Thr  His  Arg  His  Arg  Leu  Gly  Pro  Asn  Tyr  Leu  Gln  Ile  Pro  Val  Asn
               365                      370                     375
```

| | | | | | | | | | | | | | | | |
|---|---|---|---|---|---|---|---|---|---|---|---|---|---|---|---|
| TGT | CCC | TAC | CGC | GCT | CGA | GTG | GCC | AAC | TAC | CAG | CGT | GAT | GGC | CCC | ATG | 1263 |
| Cys | Pro | Tyr | Arg | Ala | Arg | Val | Ala | Asn | Tyr | Gln | Arg | Asp | Gly | Pro | Met |  |
|  |  | 380 |  |  |  |  | 385 |  |  |  |  |  | 390 |  |  |  |
| TGC | ATG | CAT | GAC | AAC | CAG | GGT | GGT | GCC | CCC | AAC | TAT | TAC | CCC | AAC | AGC | 1311 |
| Cys | Met | His | Asp | Asn | Gln | Gly | Gly | Ala | Pro | Asn | Tyr | Tyr | Pro | Asn | Ser |  |
|  |  | 395 |  |  |  |  | 400 |  |  |  |  |  | 405 |  |  |  |
| TTC | AGC | GCA | CCA | GAG | CAG | CAG | CGC | TCA | GCC | CTG | GAG | CAC | AGC | GTC | CAG | 1359 |
| Phe | Ser | Ala | Pro | Glu | Gln | Gln | Arg | Ser | Ala | Leu | Glu | His | Ser | Val | Gln |  |
|  | 410 |  |  |  |  | 415 |  |  |  |  | 420 |  |  |  |  |  |
| TGC | GCT | GTA | GAT | GTG | AAA | CGC | TTC | AAC | AGT | GCT | AAT | GAA | GAC | AAT | GTC | 1407 |
| Cys | Ala | Val | Asp | Val | Lys | Arg | Phe | Asn | Ser | Ala | Asn | Glu | Asp | Asn | Val |  |
| 425 |  |  |  |  | 430 |  |  |  |  | 435 |  |  |  |  | 440 |  |
| ACT | CAG | GTG | CGG | ACA | TTC | TAC | ACA | AAG | GTG | TTG | AAT | GAG | GAG | GAG | AGG | 1455 |
| Thr | Gln | Val | Arg | Thr | Phe | Tyr | Thr | Lys | Val | Leu | Asn | Glu | Glu | Glu | Arg |  |
|  |  |  |  | 445 |  |  |  |  | 450 |  |  |  |  | 455 |  |  |
| AAA | CGC | CTG | TGT | GAG | AAC | ATT | GCC | GGC | CAC | CTG | AAG | GAC | GCT | CAG | CTT | 1503 |
| Lys | Arg | Leu | Cys | Glu | Asn | Ile | Ala | Gly | His | Leu | Lys | Asp | Ala | Gln | Leu |  |
|  |  |  | 460 |  |  |  |  | 465 |  |  |  |  | 470 |  |  |  |
| TTC | ATT | CAG | AAG | AAA | GCG | GTC | AAG | AAT | TTC | ACT | GAC | GTC | CAC | CCT | GAC | 1551 |
| Phe | Ile | Gln | Lys | Lys | Ala | Val | Lys | Asn | Phe | Thr | Asp | Val | His | Pro | Asp |  |
|  |  | 475 |  |  |  |  | 480 |  |  |  |  | 485 |  |  |  |  |
| TAT | GGG | GCC | CGC | ATC | CAG | GCT | CTT | CTG | GAC | AAG | TAC | AAC | GCT | GAG | AAG | 1599 |
| Tyr | Gly | Ala | Arg | Ile | Gln | Ala | Leu | Leu | Asp | Lys | Tyr | Asn | Ala | Glu | Lys |  |
|  | 490 |  |  |  |  | 495 |  |  |  |  | 500 |  |  |  |  |  |
| CCT | AAG | AAC | GCA | ATT | CAC | ACC | TAC | ACG | CAG | GCC | GGC | TCT | CAC | ATG | GCT | 1647 |
| Pro | Lys | Asn | Ala | Ile | His | Thr | Tyr | Thr | Gln | Ala | Gly | Ser | His | Met | Ala |  |
| 505 |  |  |  |  | 510 |  |  |  |  | 515 |  |  |  |  | 520 |  |
| GCG | AAG | GGA | AAA | GCT | AAC | CTG | TAACTCCGGT | GCTCAGCCTC | CGCTGAGGAG |  |  |  |  |  |  | 1698 |
| Ala | Lys | Gly | Lys | Ala | Asn | Leu |  |  |  |  |  |  |  |  |  |  |
|  |  |  |  | 525 |  |  |  |  |  |  |  |  |  |  |  |  |

| | | | | |
|---|---|---|---|---|
| ACCTCTCGTG | AAGCCGAGCC | TGAGGATCAC | CTGTAATCAA | CGCTGGATGG | ATTCTCCCCC | 1758 |
| GCCGGAGCGC | AGACTCACGC | TGATGACTTT | AAAACGATAA | TCCGGGCTTC | TAGAGTGAAT | 1818 |
| GATAACCATG | CTTTTGATGC | CGTTTCCTGA | AGGGAAATGA | AAGGTTAGGG | CTTAGCAATC | 1878 |
| ATTTAACAGA | AACATGGATC | TAATAGGACT | TCTGTTTGGA | TTATTCATTT | AAATGACTAC | 1938 |
| ATTTAAAATG | ATTACAAGAA | AGGTGTTCTA | GCCAGAAACA | TGACTTGATT | AGACAAGATA | 1998 |
| AAAATCTTGG | CGAGAATAGT | GTATTCTCCT | ATTACCTCAT | GGTCTGGTAT | ATATACAATA | 2058 |
| CAACACACAT | ACCACACACA | CACACACATG | CAATACACAC | ACTACACACA | CATACACACA | 2118 |
| CTCACACACA | CTCATACACA | CACATGAAGA | GATGATAAAG | ATGGCCCACT | CAGAATTTTT | 2178 |
| TTTTTATTTT | TCTAAGGTCC | TTATAAGCAA | AACCATACTT | GCATCATGTC | TTCCAAAAGT | 2238 |
| AACTTTAGCA | CTGTTGAAAC | TTAATGTTTA | TTCCTGTGCT | GTGCGGTGCT | GTGCTGTGCT | 2298 |
| GTGCTGTGCA | GCTAATCAGA | TTCTTGTTTT | TTCCCACTTG | GATTATGTTG | ATGCTAATAC | 2358 |
| GCAGTGATTT | CACATAGGAT | GATTTGTACT | TGCTTACATT | TTTACAATAA | AATGATCTAC | 2418 |
| ATGGA | | | | | | 2423 |

( 2 ) INFORMATION FOR SEQ ID NO:26:

( i ) SEQUENCE CHARACTERISTICS:
        ( A ) LENGTH: 527 amino acids
        ( B ) TYPE: amino acid
        ( D ) TOPOLOGY: linear ( i i ) MOLECULE TYPE: protein ( x i ) SEQUENCE DESCRIPTION: SEQ ID NO:26:

Met    Ser    Asp    Ser    Arg    Asp    Pro    Ala    Ser    Asp    Gln    Met    Lys    Gln    Trp    Lys

|     |     |     |     |     |     |     |     |     |     |     |     |     |     |     |
| --- | --- | --- | --- | --- | --- | --- | --- | --- | --- | --- | --- | --- | --- | --- |
| 1 |  |  |  | 5 |  |  |  |  | 10 |  |  |  |  | 15 |

Glu Gln Arg Ala Ser Gln Arg Pro Asp Val Leu Thr Thr Gly Gly Gly
                    20                      25                          30

Asn Pro Ile Gly Asp Lys Leu Asn Ile Met Thr Ala Gly Ser Arg Gly
            35                      40                      45

Pro Leu Leu Val Gln Asp Val Val Phe Thr Asp Glu Met Ala His Phe
        50                      55                      60

Asp Arg Glu Arg Ile Pro Glu Arg Val Val His Ala Lys Gly Ala Gly
65                          70                      75                      80

Ala Phe Gly Tyr Phe Glu Val Thr His Asp Ile Thr Arg Tyr Ser Lys
                    85                      90                      95

Gly Lys Val Phe Glu His Ile Gly Lys Arg Thr Pro Ile Ala Val Arg
                100                     105                     110

Phe Ser Thr Val Ala Gly Glu Ser Gly Ser Ala Asp Thr Val Arg Asp
            115                     120                     125

Pro Arg Gly Phe Ala Val Lys Phe Tyr Thr Glu Asp Gly Asn Trp Asp
        130                     135                     140

Leu Val Gly Asn Asn Thr Pro Ile Phe Phe Ile Arg Asp Ala Ile Leu
145                     150                     155                     160

Phe Pro Ser Phe Ile His Ser Gln Lys Arg Asn Pro Gln Thr His Leu
                165                     170                     175

Lys Asp Pro Asp Met Val Trp Asp Phe Trp Ser Leu Arg Pro Glu Ser
            180                     185                     190

Leu His Gln Val Ser Phe Leu Phe Ser Asp Arg Gly Ile Pro Asp Gly
        195                     200                     205

His Arg His Met Asn Gly Tyr Gly Ser His Thr Phe Lys Leu Val Asn
    210                     215                     220

Ala Asp Gly Glu Ala Val Tyr Cys Lys Phe His Tyr Lys Thr Asp Gln
225                     230                     235                     240

Gly Ile Lys Asn Leu Pro Val Gly Glu Ala Gly Arg Leu Ala Gln Glu
                245                     250                     255

Asp Pro Asp Tyr Gly Leu Arg Asp Leu Phe Asn Ala Ile Ala Asn Gly
            260                     265                     270

Asn Tyr Pro Ser Trp Thr Phe Tyr Ile Gln Val Met Thr Phe Lys Glu
        275                     280                     285

Ala Glu Thr Phe Pro Phe Asn Pro Phe Asp Leu Thr Lys Val Trp Pro
    290                     295                     300

His Lys Asp Tyr Pro Leu Ile Pro Val Gly Lys Val Val Leu Asn Lys
305                     310                     315                     320

Asn Pro Val Asn Tyr Phe Ala Glu Val Glu Gln Met Ala Phe Asp Pro
                325                     330                     335

Ser Asn Met Pro Pro Gly Ile Glu Pro Ser Pro Asp Lys Lys Leu Gln
            340                     345                     350

Gly Arg Leu Phe Ala Tyr Pro Asp Thr His Arg His Arg Leu Gly Pro
        355                     360                     365

Asn Tyr Leu Gln Ile Pro Val Asn Cys Pro Tyr Arg Ala Arg Val Ala
    370                     375                     380

Asn Tyr Gln Arg Asp Gly Pro Met Cys Met His Asp Asn Gln Gly Gly
385                     390                     395                     400

Ala Pro Asn Tyr Tyr Pro Asn Ser Phe Ser Ala Pro Glu Gln Gln Arg
                405                     410                     415

Ser Ala Leu Glu His Ser Val Gln Cys Ala Val Asp Val Lys Arg Phe
            420                     425                     430

| Asn | Ser | Ala | Asn | Glu | Asp | Asn | Val | Thr | Gln | Val | Arg | Thr | Phe | Tyr | Thr |
|-----|-----|-----|-----|-----|-----|-----|-----|-----|-----|-----|-----|-----|-----|-----|-----|
|     |     | 435 |     |     |     | 440 |     |     |     |     |     | 445 |     |     |     |

| Lys | Val | Leu | Asn | Glu | Glu | Glu | Arg | Lys | Arg | Leu | Cys | Glu | Asn | Ile | Ala |
|-----|-----|-----|-----|-----|-----|-----|-----|-----|-----|-----|-----|-----|-----|-----|-----|
|     | 450 |     |     |     |     | 455 |     |     |     |     | 460 |     |     |     |     |

| Gly | His | Leu | Lys | Asp | Ala | Gln | Leu | Phe | Ile | Gln | Lys | Lys | Ala | Val | Lys |
|-----|-----|-----|-----|-----|-----|-----|-----|-----|-----|-----|-----|-----|-----|-----|-----|
| 465 |     |     |     | 470 |     |     |     |     | 475 |     |     |     |     |     | 480 |

| Asn | Phe | Thr | Asp | Val | His | Pro | Asp | Tyr | Gly | Ala | Arg | Ile | Gln | Ala | Leu |
|-----|-----|-----|-----|-----|-----|-----|-----|-----|-----|-----|-----|-----|-----|-----|-----|
|     |     |     |     | 485 |     |     |     |     | 490 |     |     |     |     | 495 |     |

| Leu | Asp | Lys | Tyr | Asn | Ala | Glu | Lys | Pro | Lys | Asn | Ala | Ile | His | Thr | Tyr |
|-----|-----|-----|-----|-----|-----|-----|-----|-----|-----|-----|-----|-----|-----|-----|-----|
|     |     |     | 500 |     |     |     |     | 505 |     |     |     |     | 510 |     |     |

| Thr | Gln | Ala | Gly | Ser | His | Met | Ala | Ala | Lys | Gly | Lys | Ala | Asn | Leu |
|-----|-----|-----|-----|-----|-----|-----|-----|-----|-----|-----|-----|-----|-----|-----|
|     |     | 515 |     |     |     |     | 520 |     |     |     |     | 525 |     |     |

( 2 ) INFORMATION FOR SEQ ID NO:27:

( i ) SEQUENCE CHARACTERISTICS:
        ( A ) LENGTH: 969 base pairs
        ( B ) TYPE: nucleic acid
        ( C ) STRANDEDNESS: double
        ( D ) TOPOLOGY: unknown ( i i ) MOLECULE TYPE: cDNA to mRNA ( i i i ) HYPOTHETICAL: NO ( i v ) ANTI-SENSE: NO ( v i ) ORIGINAL SOURCE:
        ( C ) INDIVIDUAL ISOLATE: human manganese superoxide dismutase
        EMBL #X59445

( i x ) FEATURE:
        ( A ) NAME/KEY: CDS
        ( B ) LOCATION: 61..729

( x i ) SEQUENCE DESCRIPTION: SEQ ID NO:27:

| TGGCTTCGGC | AGCGGCTTCA | GCAGATCGGC | GGCATCAGCG | GTAGCACCAG | CACTAGCAGC | 60 |
|---|---|---|---|---|---|---|

| ATG | TTG | AGC | CGG | GCA | GTG | TGC | GGC | ACC | AGC | AGG | CAG | CTG | GCT | CCG | GCT | 108 |
|-----|-----|-----|-----|-----|-----|-----|-----|-----|-----|-----|-----|-----|-----|-----|-----|-----|
| Met | Leu | Ser | Arg | Ala | Val | Cys | Gly | Thr | Ser | Arg | Gln | Leu | Ala | Pro | Ala |  |
| 1 |  |  |  | 5 |  |  |  |  | 10 |  |  |  |  | 15 |  |  |

| TTG | GGG | TAT | CTG | GGC | TCC | AGG | CAG | AAG | CAC | AGC | CTC | CCC | GAC | CTG | CCC | 156 |
|-----|-----|-----|-----|-----|-----|-----|-----|-----|-----|-----|-----|-----|-----|-----|-----|-----|
| Leu | Gly | Tyr | Leu | Gly | Ser | Arg | Gln | Lys | His | Ser | Leu | Pro | Asp | Leu | Pro |  |
|  |  |  | 20 |  |  |  |  | 25 |  |  |  |  | 30 |  |  |  |

| TAC | GAC | TAC | GGC | GCC | CTG | GAA | CCT | CAC | ATC | AAC | GCG | CAG | ATC | ATG | CAG | 204 |
|-----|-----|-----|-----|-----|-----|-----|-----|-----|-----|-----|-----|-----|-----|-----|-----|-----|
| Tyr | Asp | Tyr | Gly | Ala | Leu | Glu | Pro | His | Ile | Asn | Ala | Gln | Ile | Met | Gln |  |
|  |  |  | 35 |  |  |  |  | 40 |  |  |  |  | 45 |  |  |  |

| CTG | CAC | CAC | AGC | AAG | CAC | CAC | GCG | GCC | TAC | GTG | AAC | AAC | CTG | AAC | GTC | 252 |
|-----|-----|-----|-----|-----|-----|-----|-----|-----|-----|-----|-----|-----|-----|-----|-----|-----|
| Leu | His | His | Ser | Lys | His | His | Ala | Ala | Tyr | Val | Asn | Asn | Leu | Asn | Val |  |
|  |  | 50 |  |  |  |  | 55 |  |  |  |  | 60 |  |  |  |  |

| AAC | GAG | GAG | AAG | TAC | CAG | GAG | GCG | TTG | GCC | AAG | GGA | GAT | GTT | ACA | GCC | 300 |
|-----|-----|-----|-----|-----|-----|-----|-----|-----|-----|-----|-----|-----|-----|-----|-----|-----|
| Asn | Glu | Glu | Lys | Tyr | Gln | Glu | Ala | Leu | Ala | Lys | Gly | Asp | Val | Thr | Ala |  |
| 65 |  |  |  |  | 70 |  |  |  |  | 75 |  |  |  |  | 80 |  |

| CAG | ATA | GCT | CTT | CAG | CCT | GCA | CTG | AAG | TTC | AAT | GGT | GGT | GGT | CAT | ATC | 348 |
|-----|-----|-----|-----|-----|-----|-----|-----|-----|-----|-----|-----|-----|-----|-----|-----|-----|
| Gln | Ile | Ala | Leu | Gln | Pro | Ala | Leu | Lys | Phe | Asn | Gly | Gly | Gly | His | Ile |  |
|  |  |  |  | 85 |  |  |  |  | 90 |  |  |  |  | 95 |  |  |

| AAT | CAT | AGC | ATT | TTC | TGG | ACA | AAC | CTC | AGC | CCT | AAC | GGT | GGT | GGA | GAA | 396 |
|-----|-----|-----|-----|-----|-----|-----|-----|-----|-----|-----|-----|-----|-----|-----|-----|-----|
| Asn | His | Ser | Ile | Phe | Trp | Thr | Asn | Leu | Ser | Pro | Asn | Gly | Gly | Gly | Glu |  |
|  |  |  | 100 |  |  |  |  | 105 |  |  |  |  | 110 |  |  |  |

| CCC | AAA | GGG | GAG | TTG | CTG | GAA | GCC | ATC | AAA | CGT | GAC | TTT | GGT | TCC | TTT | 444 |
|-----|-----|-----|-----|-----|-----|-----|-----|-----|-----|-----|-----|-----|-----|-----|-----|-----|
| Pro | Lys | Gly | Glu | Leu | Leu | Glu | Ala | Ile | Lys | Arg | Asp | Phe | Gly | Ser | Phe |  |
|  |  | 115 |  |  |  |  | 120 |  |  |  |  | 125 |  |  |  |  |

| GAC | AAG | TTT | AAG | GAG | AAG | CTG | ACG | GCT | GCA | TCT | GTT | GGT | GTC | CAA | GGC | 492 |
|-----|-----|-----|-----|-----|-----|-----|-----|-----|-----|-----|-----|-----|-----|-----|-----|-----|
| Asp | Lys | Phe | Lys | Glu | Lys | Leu | Thr | Ala | Ala | Ser | Val | Gly | Val | Gln | Gly |  |
|  | 130 |  |  |  |  | 135 |  |  |  |  | 140 |  |  |  |  |  |

| | | | | | | | | | | | | | | | | |
|---|---|---|---|---|---|---|---|---|---|---|---|---|---|---|---|---|
| TCA | GGT | TGG | GGT | TGG | CTT | GGT | TTC | AAT | AAG | GAA | CGG | GGA | CAC | TTA | CAA | 540 |
| Ser | Gly | Trp | Gly | Trp | Leu | Gly | Phe | Asn | Lys | Glu | Arg | Gly | His | Leu | Gln | |
| 145 | | | | | 150 | | | | | 155 | | | | | 160 | |
| ATT | GCT | GCT | TGT | CCA | AAT | CAG | GAT | CCA | CTG | CAA | GGA | ACA | ACA | GGC | CTT | 588 |
| Ile | Ala | Ala | Cys | Pro | Asn | Gln | Asp | Pro | Leu | Gln | Gly | Thr | Thr | Gly | Leu | |
| | | | | 165 | | | | | 170 | | | | | 175 | | |
| ATT | CCA | CTG | CTG | GGG | ATT | GAT | GTG | TGG | GAG | CAC | GCT | TAC | TAC | CTT | CAG | 636 |
| Ile | Pro | Leu | Leu | Gly | Ile | Asp | Val | Trp | Glu | His | Ala | Tyr | Tyr | Leu | Gln | |
| | | | 180 | | | | | 185 | | | | | 190 | | | |
| TAT | AAA | AAT | GTC | AGG | CCT | GAT | TAT | CTA | AAA | GCT | ATT | TGG | AAT | GTA | ATC | 684 |
| Tyr | Lys | Asn | Val | Arg | Pro | Asp | Tyr | Leu | Lys | Ala | Ile | Trp | Asn | Val | Ile | |
| | | 195 | | | | | 200 | | | | | 205 | | | | |
| AAC | TGG | GAG | AAT | GTA | ACT | GAA | AGA | TAC | ATG | GCT | TGC | AAA | AAG | TAAACCACGA | | 736 |
| Asn | Trp | Glu | Asn | Val | Thr | Glu | Arg | Tyr | Met | Ala | Cys | Lys | Lys | | | |
| 210 | | | | | 215 | | | | | 220 | | | | | | |

| | | | | |
|---|---|---|---|---|
| TCGTTATGCT | GAGTATGTTA | AGCTCTTTAT | GACTGTTTTT | GTAGTGGTAT | AGAGTACTGC | 796 |
| AGAATACAGT | AAGCTGCTCT | ATTGTAGCAT | TTCTTGATGT | TGCTTAGTCA | CTTATTTCAT | 856 |
| AAACAACTTA | ATGTTCTGAA | TAATTTCTTA | CTAAACATTT | TGTTATTGGG | CAAGTGATTG | 916 |
| AAAATAGTAA | ATGCTTTGTG | TGATTGAAAA | AAAAAAAAAA | AAAAAAAAA | AAA | 969 |

( 2 ) INFORMATION FOR SEQ ID NO:28:

( i ) SEQUENCE CHARACTERISTICS:
        ( A ) LENGTH: 222 amino acids
        ( B ) TYPE: amino acid
        ( D ) TOPOLOGY: linear ( i i ) MOLECULE TYPE: protein ( x i ) SEQUENCE DESCRIPTION: SEQ ID NO:28:

| | | | | | | | | | | | | | | |
|---|---|---|---|---|---|---|---|---|---|---|---|---|---|---|
| Met | Leu | Ser | Arg | Ala | Val | Cys | Gly | Thr | Ser | Arg | Gln | Leu | Ala | Pro | Ala |
| 1 | | | | 5 | | | | | 10 | | | | | 15 | |
| Leu | Gly | Tyr | Leu | Gly | Ser | Arg | Gln | Lys | His | Ser | Leu | Pro | Asp | Leu | Pro |
| | | | 20 | | | | | 25 | | | | | 30 | | |
| Tyr | Asp | Tyr | Gly | Ala | Leu | Glu | Pro | His | Ile | Asn | Ala | Gln | Ile | Met | Gln |
| | | 35 | | | | | 40 | | | | | 45 | | | |
| Leu | His | His | Ser | Lys | His | His | Ala | Ala | Tyr | Val | Asn | Asn | Leu | Asn | Val |
| | 50 | | | | | 55 | | | | | 60 | | | | |
| Asn | Glu | Glu | Lys | Tyr | Gln | Glu | Ala | Leu | Ala | Lys | Gly | Asp | Val | Thr | Ala |
| 65 | | | | | 70 | | | | | 75 | | | | | 80 |
| Gln | Ile | Ala | Leu | Gln | Pro | Ala | Leu | Lys | Phe | Asn | Gly | Gly | Gly | His | Ile |
| | | | | 85 | | | | | 90 | | | | | 95 | |
| Asn | His | Ser | Ile | Phe | Trp | Thr | Asn | Leu | Ser | Pro | Asn | Gly | Gly | Gly | Glu |
| | | | 100 | | | | | 105 | | | | | 110 | | |
| Pro | Lys | Gly | Glu | Leu | Leu | Glu | Ala | Ile | Lys | Arg | Asp | Phe | Gly | Ser | Phe |
| | | 115 | | | | | 120 | | | | | 125 | | | |
| Asp | Lys | Phe | Lys | Glu | Lys | Leu | Thr | Ala | Ala | Ser | Val | Gly | Val | Gln | Gly |
| | 130 | | | | | 135 | | | | | 140 | | | | |
| Ser | Gly | Trp | Gly | Trp | Leu | Gly | Phe | Asn | Lys | Glu | Arg | Gly | His | Leu | Gln |
| 145 | | | | | 150 | | | | | 155 | | | | | 160 |
| Ile | Ala | Ala | Cys | Pro | Asn | Gln | Asp | Pro | Leu | Gln | Gly | Thr | Thr | Gly | Leu |
| | | | | 165 | | | | | 170 | | | | | 175 | |
| Ile | Pro | Leu | Leu | Gly | Ile | Asp | Val | Trp | Glu | His | Ala | Tyr | Tyr | Leu | Gln |
| | | | 180 | | | | | 185 | | | | | 190 | | |
| Tyr | Lys | Asn | Val | Arg | Pro | Asp | Tyr | Leu | Lys | Ala | Ile | Trp | Asn | Val | Ile |
| | | 195 | | | | | 200 | | | | | 205 | | | |

Asn Trp Glu Asn Val Thr Glu Arg Tyr Met Ala Cys Lys Lys
     210                 215                 220

( 2 ) INFORMATION FOR SEQ ID NO:29:

( i ) SEQUENCE CHARACTERISTICS:
        ( A ) LENGTH: 691 base pairs
        ( B ) TYPE: nucleic acid
        ( C ) STRANDEDNESS: double
        ( D ) TOPOLOGY: unknown ( i i ) MOLECULE TYPE: DNA (genomic)

( i i i ) HYPOTHETICAL: NO ( i v ) ANTI-SENSE: NO ( v i ) ORIGINAL SOURCE:
        ( C ) INDIVIDUAL ISOLATE: human enolase gene (EMBL #X56832)
        fragment containinig nucleotides -628 to +63

( i x ) FEATURE:
        ( A ) NAME/KEY: CDS
        ( B ) LOCATION: 629..691

( x i ) SEQUENCE DESCRIPTION: SEQ ID NO:29:

```
CCTGGGGGTG  GAGGTAGTAA  AGGGTGAGCA  TGGTATTGGC  TTGGAGGAAG  TGGGGGACAT        60

TTCTGCTTTT  TTTCCTCCTG  GGACTGGAGA  TGCTTGAAAA  AGCTGGGGGA  AGGGCGGCT        120

GGAGCAAGCA  GATGGGACAA  ACTCTGGGAA  CACCGAAGGA  TCTAGGGAAA  GGAGGCTGTG       180

AGGAGGGCAG  CAGGGATGGA  TAGAAAAGGG  CAGCTAGAGC  TGGAACCTGA  TAGGGAATTG       240

GGGGCCCAAG  GAGATTTCGG  AGCAGGAAAA  TGAGAACCAG  AAAGGATTTG  AAGGCCACCA       300

GCCATGGAGA  ACAGACTGCT  TGACCAGAGG  GGTGGAAGGA  GAAGGCCTAA  GTGGAGGCTT       360

GGGGAGGTG   GGGGCTTGGT  GAGCGGTGGC  ATCCCAGGAG  CTATAGATAA  GAGGCCCCTG       420

GATTCTTAGG  ATGGAGGGT   GGAATAAGAG  CTGTTCTGAG  TGGGGGAGGG  GGCTGCGCCT       480

GCCTCTTTGG  TCTGTGACCT  TTTTGTAGGG  TATTTTTAGC  TCCAGCACCT  GCCTTCTTGG       540

AGTGGGGAAG  AATCTTAAAG  GGCAAGGGAT  TTCTGGTTCC  TTAAGAGATC  AACTGTCTAC       600

ACTCACTCAC  ACCTCCTGTC  CTGCAGCC ATG GCC ATG CAG AAA ATC TTT GCC            652
                                Met Ala Met Gln Lys Ile Phe Ala
                                 1               5

CGG GAA ATC TTG GAC TCC AGG GGC AAC CCC ACG GTG GAG                         691
Arg Glu Ile Leu Asp Ser Arg Gly Asn Pro Thr Val Glu
     10                  15                  20
```

( 2 ) INFORMATION FOR SEQ ID NO:30:

( i ) SEQUENCE CHARACTERISTICS:
        ( A ) LENGTH: 21 amino acids
        ( B ) TYPE: amino acid
        ( D ) TOPOLOGY: linear ( i i ) MOLECULE TYPE: protein ( x i ) SEQUENCE DESCRIPTION: SEQ ID NO:30:

Met Ala Met Gln Lys Ile Phe Ala Arg Glu Ile Leu Asp Ser Arg Gly
 1               5                  10                  15

Asn Pro Thr Val Glu
             20

( 2 ) INFORMATION FOR SEQ ID NO:31:

( i ) SEQUENCE CHARACTERISTICS:
        ( A ) LENGTH: 17 base pairs
        ( B ) TYPE: nucleic acid ( C ) STRANDEDNESS: double
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: PKM/ENO3 consensus sequence ( x i ) SEQUENCE DESCRIPTION: SEQ ID NO:31:

GAGAGGCGGG CTNNCTG                                                                                                      1 7